(12) United States Patent
Meutermans et al.

(10) Patent No.: US 7,291,623 B2
(45) Date of Patent: Nov. 6, 2007

(54) COMPOUNDS THAT INTERACT WITH KINASES

(75) Inventors: Wim Meutermans, Toowong (AU); Karl Schafer, Carindale (AU); Michael L. West, Hemmant (AU); Craig Muldoon, Coburg (AU); Fiona Foley, Greenslopes (AU); Natalie Bouloc, Carshalton (GB); Gerald Tometzki, Manly West (AU)

(73) Assignee: Alchemia Limited, Eight Mile Plains, Queensland (AU)

( * ) Notice: Subject to any disclaimer, the term of this patent is extended or adjusted under 35 U.S.C. 154(b) by 181 days.

(21) Appl. No.: 10/526,388

(22) PCT Filed: Sep. 5, 2003

(86) PCT No.: PCT/AU03/01146

§ 371 (c)(1),
(2), (4) Date: Jun. 2, 2005

(87) PCT Pub. No.: WO2004/022572

PCT Pub. Date: Mar. 18, 2004

(65) Prior Publication Data

US 2005/0209176 A1    Sep. 22, 2005

(30) Foreign Application Priority Data

Sep. 6, 2002   (AU) .............................. 2002951247

(51) Int. Cl.
*A61K 31/52* (2006.01)
*A61K 31/417* (2006.01)
*A61K 31/4166* (2006.01)
*A61K 31/4184* (2006.01)
*C07D 257/04* (2006.01)
*C07D 473/32* (2006.01)

(52) U.S. Cl. ........................... 514/263.21; 514/263.23; 514/381; 514/382; 544/277; 548/252; 548/253

(58) Field of Classification Search ................ 548/253; 544/277; 514/263.21, 382
See application file for complete search history.

(56) References Cited

FOREIGN PATENT DOCUMENTS

| EP | 1 106 609 | 6/2001 |
|---|---|---|
| WO | WO96/40705 | 12/1996 |
| WO | WO99/41266 | 8/1999 |
| WO | WO 01/32653 | 5/2001 |

OTHER PUBLICATIONS

Garner et al., Journal of Organic Chemistry, vol. 55(12), pp. 3772-3787 (1990).*
Kasnar, "Synthesis of 'Reversed' and 'Double Headed' Nucleosides," Nucleosides & Nucleotides, vol. 14, Issue 3-5, pp. 341-344 (1995).*
Walcazk et al., "Synthesis of reversed azole nucleosides under the Mitsunobu reaction conditions," Polish J. of Chemistry 70(7), pp. 867-871 (1996).*

\* cited by examiner

*Primary Examiner*—Rebecca Anderson
*Assistant Examiner*—Andrew B. Freistein
(74) *Attorney, Agent, or Firm*—Nixon & Vanderhye P.C.

(57) ABSTRACT

A method of inhibiting or effecting the activity of protein kinase activity which comprises contacting a protein kinase with a compound of formula (I) being a derivative of a furanose or pyranose form of a monosaccharide, or a pharmaceutically acceptable salt thereof.

25 Claims, No Drawings

COMPOUNDS THAT INTERACT WITH KINASES

FIELD OF THE INVENTION

The invention is directed to classes of biologically active compounds that interact in a pharmaceutically significant manner with protein kinases, and particularly to provide compounds suitable for the treatment of disorders mediated by protein kinase activity. The invention is also directed to treatment of the above mentioned disorders. The invention is also directed to the preparation of novel compounds per se.

BACKGROUND OF THE INVENTION

The drug discovery landscape has been transformed by the genomics revolution. Advances in the understanding of biomolecular pathways and the roles they play in disease is generating vast numbers of targets for therapeutic intervention. Protein kinases now represent an extensive and important class of therapeutic targets.

Kinases are key components in almost all signal transduction pathways, modulating extracellular and intracellular signalling processes that mediate events such as cell growth and differentiation, metabolism and apoptosis. Kinases do this by catalysing the transfer of a phosphate group from ATP to protein substrates. The pivotal role of kinases is emphasized by the fact that kinases represent the third most populous domain in the proteome.

Kinases have been implicated in many diseases. Twenty percent of oncogenes code for tyrosine kinases. Kinases play pivotal roles in many leukemias, tumours and other proliferative disorders. Other states involving kinases include inflammatory disorders such as psoriasis, cardiovascular diseases such as restenosis, viral induced diseases such as Kaposi's sarcoma, circulatory diseases such as atherosclerosis and fibroproliferative diseases. Specific kinases are often implicated in particular disease states and therefore present themselves as potential targets for therapeutic intervention.

The kinase family includes serine/threonine kinases and tyrosine kinases, with the amino acid referring to the particular residue on a protein substrate that is phosphorylated. The tyrosine kinases can be further divided into receptor tyrosine kinases and non-receptor tyrosine kinases.

Considering the rate of generation and nature of the targets currently being deconvoluted by biologists, there is a need for the development of drug candidates, designed in a rational manner to purposely interact with selected targets, such as the kinases.

From a drug discovery perspective, carbohydrate pyranose and furanose rings and their derivatives are well suited as templates. Each sugar represents a three-dimensional scaffold to which a variety of substituents can be attached, usually via a scaffold hydroxyl group, although occasionally a scaffold carboxyl or amino group may be present for substitution. By varying the substituents, their relative position on the sugar scaffold, and the type of sugar to which the substituents are coupled, numerous highly diverse structures are obtainable. An important feature to note with carbohydrates, is that molecular diversity is achieved not only in the type of substituents, but also in the three dimensional presentation. The different stereoisomers of carbohydrates that occur naturally, offer the inherent structural advantage of providing alternative presentation of substituents. We have developed a system that allows the chemical synthesis of highly structurally and functionally diverse derivatised carbohydrate and tetrahydropyran structures, of both natural and unnatural origin. The diversity accessible is particularly augmented by the juxtaposition of both structural and functional aspects of the molecules.

A number of kinase inhibitors have appeared in the scientific literature to date. Many have entered human clinical trials and in two cases, Gleevac and Iressa, approval for the treatment of various tumours has been granted (Cohen, P., Nature Tev. Drug Discovery, 1, 309-316, 2002). The specificity of published kinase inhibitors varies widely and it is apparent from the study of Gleevac that specificity for a single kinase is not a prerequisite for the inhibitor becoming a useful drug, indeed the inhibition of more than one kinase may be an advantage for therapeutic intervention. Despite some promiscuity in the target kinase being acceptable, it is generally considered desirable to have good selectivity for the target kinase(s) over more general "housekeeping" kinases. Thus selectivity and inhibitor potency must be assessed on a case by case basis.

The level of inhibition in cell based assays also shows considerable variation from approximately 0.1 micromolar to over 100 micromolar as exemplified by the following table (a more detailed study can be found in: Davies et. al., Biochem. J., 351, 95-105, 2000; and Bain et. al., Biochem. J., 371, 199-204, 2003). It is frequently the case that the most potent inhibitor is not the most suitable inhibitor for therapeutic purposes.

| Inhibitor concentration | Top 5 kinases inhibited kinase and residual activity | | | | |
|---|---|---|---|---|---|
| ML-9 | MSK-1 | ROCK-II | SmMLCK | S6K1 | CDK2 |
| 100 µM | 14% | 23% | 25% | 27% | 38% |
| LY 294002 | PI3K | CK2 | PHK | GSK3β | SGK |
| 50 µM | 13% | 18% | 44% | 53% | 72% |
| HA1077 | ROCK-II | PRK2 | MSK1 | S6K1 | PKA |
| 20 µM | 7% | 15% | 19% | 32% | 35% |
| PP2 | LCK | CDK2 | CK1 | SAPK2a | MKK1 |
| 10 µM | 1% | 3% | 6% | 21% | 55% |
| Ro-31-8220 | MAPKAPK1b | MSK1 | PKCα | GSK3β | S6K1 |
| 1 µM | 2% | 2% | 3% | 5% | 6% |

MSK-1 = mitogen and stress activated protein kinase 1;
ROCK-II = Rho associated coiled coil forming protein kinase II;
SmMLCK = smooth myosin light chain kinase;
S6K1 = p70 S6 kinase;
CDK2 = cyclin dependant kinase 2;
PI3K = phosphoinositide 3 kinase;
CK2 = casein kinase 2;
PHK = phosphorylase kinase;
GSK3β = glycogen synthetase kinase 3β;
SGK = serum and glucocortin induced kinase;
PRK2 = PKC related kinase 2;
PKA = protein kinase A;
LCK = T cell specific kinase;
CK1 = casien kinase 1;
SAPK2a = p38 kinase;
MKK1 = mitogen activated protein kinase 1;
MAPKAP-K1b = mitogen activated protein kinase activated protein kinase 1b;
PKCα = protein kinase C alpha.

It will be clearly understood that, if a prior art publication is referred to herein, this reference does not constitute an admission that the publication forms part of the common general knowledge in the art in Australia or in any other country.

SUMMARY OF THE INVENTION

Using the axioms of this drug discovery methodology, we synthesised several novel classes of chemotypes in an effort to develop drug candidates against kinase targets.

Kinases selected examples from the three different classes; serine/threonin kinase, tyrosine receptor kinase and tyrosine non-receptor kinase have been explored to determine the generality of the current invention. Compounds were tested within the industry standard concentration range described above and have revealed potent and selective inhibitors against each selected kinase target.

It is a general object of the invention to provide compounds suitable for the treatment of disorders mediated by protein kinase activity and in the treatment of the above mentioned disorders.

It is an optional object of the invention to provide a pharmaceutical formulation comprising at least one compound as described herein or a pharmaceutically acceptable salt thereof, together with one or more pharmaceutically acceptable carriers, diluents or excipients.

It is a further optional object of the invention to provide a method of treatment of a human or animal subject suffering from a disorder mediated by aberrant protein kinase activity which method comprises administering to the human or animal subject an effective amount of a compound as described herein or a pharmaceutically acceptable salt thereof.

It is a further object of the invention to prepare novel compounds per se.

In one form, the invention comprises method of inhibiting or effecting protein kinase activity which comprises contacting a protein kinase with a compound of formula I being a derivative of a furanose or pyranose form of a monosaccharide, or a pharmaceutically acceptable derivative thereof

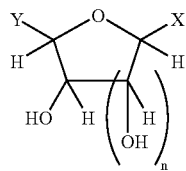

formula I

Wherein;

n is 1 or 2,

X is selected from the group consisting of: OR1, an unsubstituted 5 or 6 membered heterocyclic moiety, a substituted 5 or 6 membered heterocyclic moiety, an unsubstituted 9 or 10 membered heterobicyclic moiety and a substituted 9 or 10 membered heterobicyclic moiety, R1 is selected from the group consisting of C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, Y is selected from the group consisting of: an unsubstituted 5 or 6 membered heterocyclic moiety; a substituted 5 or 6 membered heterocyclic moiety, an unsubstituted 9 or 10 membered heterobicyclic moiety and a substituted 9 or 10 membered heterobicyclic moiety; an amino acid, a dipeptide, and

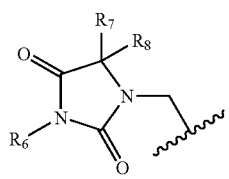

A

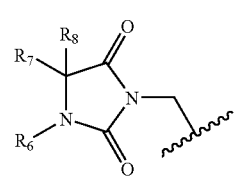

B

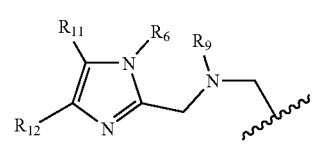

C

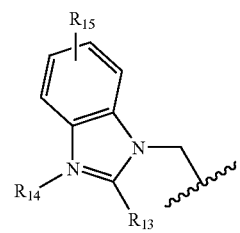

D

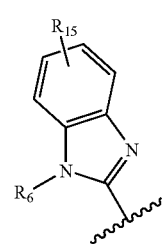

E

-continued

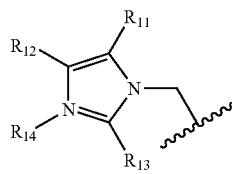

F

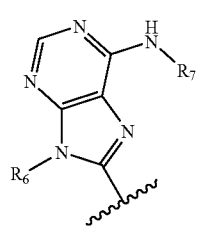

G

R6 is selected from the group consisting of H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl or C3 to C14 heteroarylalkyl, with the proviso that R6, R7 and R8 are not all H, R9 is selected from H, or —(CO)—R6, R7, R8, R11, R12, R14, are independently selected from the group consisting of: H, C1 to C7 alkyl, C1 to C7 alkenyl, C1 to C7 alkynyl, C1 to C7 acyl, C1 to C7 heteroalkyl, C6 to C14 aryl, C6 to C14 arylacyl, C6 to C14 heteroaryl, C6 to C14 heteroarylacyl, C6 to C14 arylalkyl and C6 to C14 heteroarylalkyl, R13 is selected from the group consisting of: unsubstituted phenyl unsubstituted benzyl, substituted phenyl, substituted benzyl, H, C1 to C7 alkyl, C1 to C7 alkenyl, C1 to C7 alkynyl, C1 to C7 acyl, C1 to C7 heteroalkyl, C6 to C14 aryl, C6 to C14 arylacyl, C6 to C14 heteroaryl, C6 to C14 heteroarylacyl, C6 to C14 arylalkyl or C6 to C14 heteroarylalkyl, —S—R6 and —O—R6, R15 is absent or is at least one substituent on the aromatic ring which are independently selected from the group consisting of: OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, alkyl, aminoaryl, aminoheteroaryl, thioalkyl, thioaryl and thioheteroaryl.

R1 may be substituted, cyclic or acyclic, branched and/or linear.

R7 and R8 may combine to form a cyclic structure.

R6 and one of R7 or R8 may combine to form a cyclic structure.

R11 and R12 may combine to form a cyclic structure,

X may be selected from: OR1,

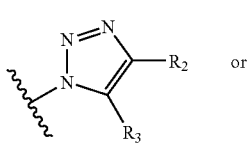 or 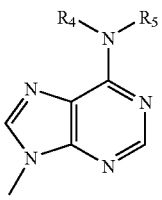

R1 and R3 are independently selected from the group consisting of: C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, R4 is selected from the group consisting of: H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, R5 is selected from the group consisting of: H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl or C3 to C14 heteroarylalkyl, C1 to C7 acyl, C6 to C14 arylacyl, and C3 to C14 heteroarylacyl, R2 is selected from the group consisting of: —(C=O)—R3, —(C=O)—OR4, and —(C=O)—NH—R4, Y is selected from:

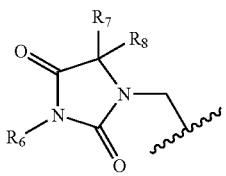

A

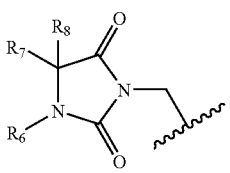

B

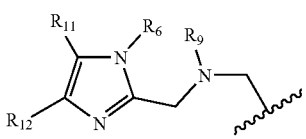

C

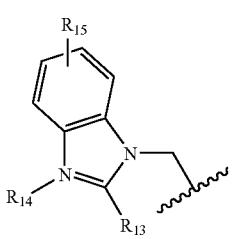

D

-continued

E
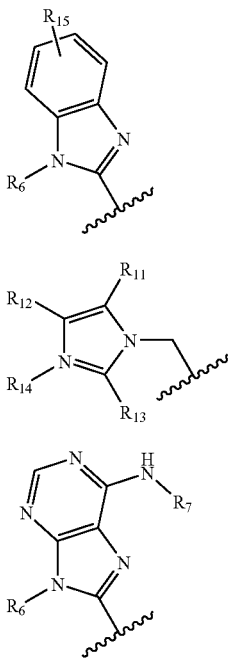

F

G

At least one of R1-R14 may be substituted and these substituents and the substituents on the substituted 5 or 6 membered heterocyclic moiety and the substituted 9 or 10 membered heterobicyclic moiety may be selected from the group consisting of: OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, alkyl aminoheteroaryl, thioalkyl, thioaryl or thioheteroaryl, which may optionally be further substituted.

X may comprise

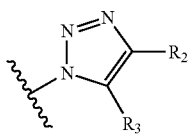

X may comprise

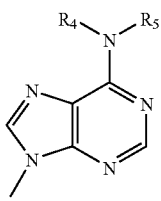

X may comprise —OR1.
Y may comprise A as described above.
Y may comprise B as described above.
Y may comprise C as described above.
Y may comprise D as described above.
Y may comprise E as described above.
Y may describe F as described above.
Y may comprise G as described above.
The protein kinase may comprise a serine or threonine kinase.
The protein kinase may comprise a tyrosine kinase.
The protein kinase may comprise one or more of the isoforms of protein kinase C.
The protein kinase may comprise Tie-2, also known as TEK, HPK-6, TIE-2 VMCM, VMCM1.
The protein kinase may comprise c-Kit also known as SCFR, CD117, PBT.
The protein kinase may comprise VEGF-R2/KDR also known as VEGFR2, VEGFR-2, VEGFR, Hs.KDR, Hs.12337, FLK1, FLK-1.
The protein kinase may comprise EGF-R also known as ERBB1, ERBB, EGFRvIII.
The protein kinase may comprise Abl also known as c-ab1, c-ABL, JTK7, p150, ABL1.
The protein kinase may comprise MET also known as HGFR, C-MET, RCCP2.
The protein kinase may comprise, CDK2 also known as p34CDK2, p33CDK2, p33CDK2.
The protein kinase may comprise PDGF also known as PDGFR1, PDGFR, PDGF-R-beta, JTK12, CD140B, PDGFRB.
The protein kinase may comprise kinase, FGFR-1 also known as N-SAM, LOC51033, FLT2, FLJ14326, CEK, C-FGR, BFGFR, H5, H4, H3, H2, FLG.
The protein kinase may comprise P38 MAP Kinase also known as p38alpha p38ALPHA, SAPK2a, SAPK2A, PRKM15, PRKM14, Mxi2, MXI2, Exip, EXIP, CSPB1, CSBP2, CSBP1, p38, RK, P38, MAPK14.
In another form, the invention comprises a compound of formula I which is a derivative of a furanose form of a monosaccharide of general formula I, formula I
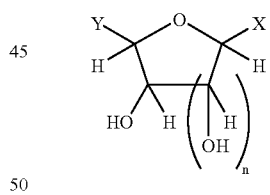

Wherein;
n is 1,
X is selected from: OR1,

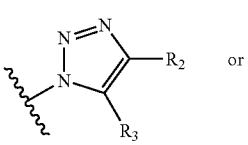 or 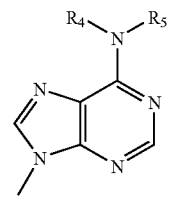

R1 and R3 are independently selected from the group consisting of: C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, R4 is selected from the group consisting of: H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, R5 is selected from the group consisting of: H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl or C3 to C14 heteroarylalkyl, C1 to C7 acyl, C6 to C14 arylacyl, and C3 to C14 heteroarylacyl, R2 is selected from —(C═O)—R3, —(C═O)—OR4, —(C═O)—NH—R4, Y is selected from the group consisting of:

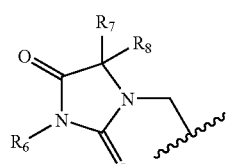
A

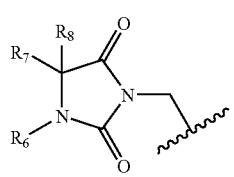
B

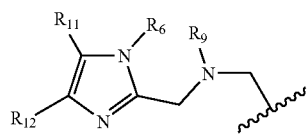
C

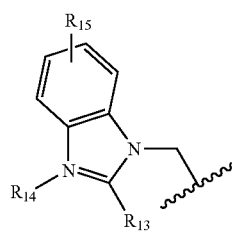
D

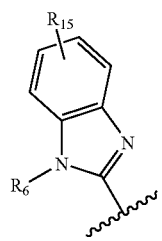
E

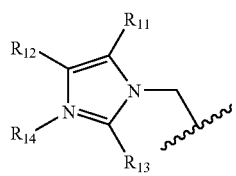
F

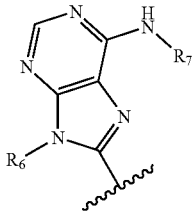
G

R6 is selected from the group consisting of H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, with the proviso that R6, R7 and R8 are not all H, R9 is selected from H, or —(CO)—R6, R7, R8, R1, R12, R14, are independently selected from the group consisting of H, C1 to C7 alkyl, C1 to C7 alkenyl, C1 to C7 alkynyl, C1 to C7 acyl, C1 to C7 heteroalkyl, C6 to C14 aryl, C6 to C14 arylacyl, C6 to C14 heteroaryl, C6 to C14 heteroarylacyl, C6 to C14 arylalkyl or C6 to C14 heteroarylalkyl, R13 is selected from the group consisting of: unsubstituted phenyl, unsubstituted benzyl, substituted phenyl, substituted benzyl, H, C1 to C7 alkyl, C1 to C7 alkenyl, C1 to C7 alkynyl, C1 to C7 acyl, C1 to C7 heteroalkyl, C6 to C14 aryl, C6 to C14 arylacyl, C6 to C14 heteroaryl, C6 to C14 heteroarylacyl, C6 to C14 arylalkyl or C6 to C14 heteroarylalkyl, —S—R6 or —O—R6, R15 is absent or is at least one substituent on the aromatic ring which is independently selected from the group consisting of: OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, alkyl, aminoaryl, aminoheteroaryl, thioalkyl, thioaryl or thioheteroaryl.

R7 and R8 may combine to form a cyclic structure.

R6 and one of R7 or R8 may combine to form a cyclic structure.

R11 and R12 may combine to form a cyclic structure.

R1, R2, R3, R4 and R5 are optionally substituted, cyclic or acyclic, branched and/or linear.

R2 and R3 may combine to form a ring structure.

R4 and R5 may combine to form a ring structure.

At least one of R1 to R5 may be substituted with a substituent selected from the group, OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, alkyl, aminoaryl, aminoheteroaryl, thioalkyl, thioaryl or thioheteroaryl, which may optionally be further substituted, X may be

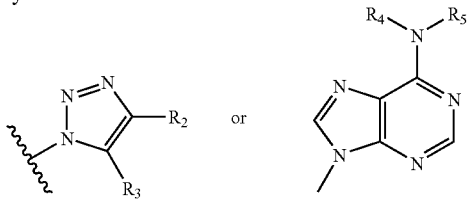

or OR1.

Y may comprise A as described above.
Y may comprise B as described above.
Y may comprise C as described above.
Y may comprise D as described above.
Y may comprise E as described above.
Y may comprise F as described above.
Y may comprise G as described above.

The compounds of the invention may be mixed with a pharmaceutical acceptable carrier, adjuvant, or vehicle which may comprise a-toxic carrier, adjuvant, or vehicle that may be administered to a patient, together with a compound of this invention, and which does not destroy the pharmacological activity thereof.

The pharmaceutical derivative may comprise a salt, ester, salt of an ester or other derivative of a compound of this invention which, upon administration to a recipient, is capable of providing, either directly or indirectly, a compound of this invention, although no limitation is meant thereby.

Compounds of the invention may be administered orally such as by means of a tabled, powder, liquid, emulsion, dispersion and the like; by inhalation; topically such as by means of a cream, ointment, salve etc; and as a suppository, although no limitation is meant thereby.

BEST MODE
General Methods

General Method 1—Amide bond formation: To a solution of an acid in DMF (0.3 ml, 0.35 M, 1.0 equiv.) at room temperature was added a solution of HBTU in DMF (0.3 ml, 0.42 M, 1.2 equiv.) followed by DIPEA (2.5 equiv.). After 10 min., a solution of the desired amine in DMF (0.3 ml, 0.37 M, 1.05 equiv.) was added. The resulting solution was stirred at room temperature for 2.5 h, then diluted with DCM (8 ml) and washed with 10% citric acid (2×5 ml), saturated NaHCO$_3$ (2×5 ml), brine (5 ml) and water (5 ml). The solvent was removed in vacuo.

General Method 2—Ester Hydrolysis: A solution of the ester (0.1 mmoles) in THF (0.5 ml) was treated with a solution of lithium hydroxide in water (0.5 ml, 0.45 M, 2.1 equiv.). The resulting mixture was stirred at room temperature overnight, then evaporated to dryness under reduced pressure to provide the corresponding carboxylic acid as the lithium salt. The residue is redissolved in either ethyl acetate or dichloromethane and washed with a small quantity of 10% citric acid solution, followed by drying of the organic layer and removal of the solvents in vacuo to yield the desired carboxylic acid. In cognate experiments sodium hydroxide or potassium hydroxide has been substituted for lithium hydroxide to for the corresponding sodium or potassium salts in comparable yields. Methanol and dioxane have been substituted for THF as the reaction solvent with comparable results.

General Method 3a—Removal of acid labile protecting groups (Isopropylidene and BOC)—solution phase: The compound was dissolved in acetonitrile and treated with 90/10 trifluoroacetic acid-water (2 ml) and monitored by t.l.c for reaction completeness. Reaction times vary considerably from 15 minutes at RT to 6 hours at RT. When complete, the mixture was concentrated under reduced pressure and co-evaporating from acetonitrile. The crude products were resuspended in water-acetonitrile and lyophilised then purificatied by reverse phase C-18 HPLC using a solvent gradient of water/acetonitrile to afford the desired product as white solids. In cognate experiments, 50/50 trifluoroacetic acid—water has been used with similar efficiency.

General Method 3b—Removal of acid labile protecting groups (isopropylidene and BOC) and cleavage from resin—solid phase: The resin bound compound (approx. 200 mg of resin) was washed with DCM (2×2 mL) then treated with TFA/DCM 1:1 (1 mL) for 15 mins. The resin was filtered and washed with acetonitrile (1 ml) (filtrates collected). This procedure was repeated for a second cycle. The filtrates were evaporated under a stream of nitrogen. The residue was redissolved in water (1 ml) and agitated for 3 h. After this time, the solution was lyophilised to afford the crude products which were purified as described above.

General Method 4—removal of an Fmoc protecting group: The Fmoc protected compound on resin (12 g of resin, 0.7 mmol/g, 8.4 mmol) was washed with DMF (2×120 ml), then treated with 20% piperidine in DMF (120 ml) and shaken at r.t. for 30 min. The resin was drained and washed with DMF (2×120 ml). The reaction was repeated and the resin was drained, washed with DMF (2×120 ml), DCM (2×120 ml), MeOH (2×120 ml) and ether (2×120 ml), and dried in vacuo for 2 h.

General Method 5—coupling of fluoro-nitro-benzoic acid: Resin bound substrate was washed under N$_2$ with dry DCM (1×80 ml, 1×60 ml). To a solution of 4-fluoro-3-nitrobenzoic acid (9.3 g, FW 185.09, 50.2 mmol, 6 equiv.) in dry DCM (60 ml) and dry DMF (9 ml) at r.t. and under N$_2$ was added 1,3-diisopropylcarbodiimide (DIC, 3.9 ml, d 0.806, FW 126.20, 24.9 mmol, 3 equiv.). The solution was stirred for 10 min., then added to the resin followed by 4-(dimethylamino)pyridine (DMAP, 102 mg, FW 122.17, 0.83 mmol, 0.1 equiv.). The resin was then shaken at r.t. for 3 h, drained, washed with DMF (4×120 ml), DCM (3×120 ml) and ether (2×120 ml), and dried in vacuo overnight. The coupling procedure may be repeated in the event of a positive ninhydrin test.

General Method 6—nucleophillic aromatic displacement: Resin bound 3-nitro-4-fluoro-benzoate XI (200 mg, 0.14 mmol) was washed under N$_2$ with dry DMF (2 ml) or dry DMSO (2 ml), then treated with a solution of the nucleophile (0.42 mmol, 3 equiv.) and diisopropylamine (DIPEA, 0.146 ml, d 0.742, FW, 129.25, 0.84 mmol, 6 equiv.) in dry DMF (2 ml) or dry DMSO (2 ml) and shaken at r.t. o/n. The resin was drained and washed with DMF (3×2 25 ml) and DCM (3×2 ml). In the case of DMSO as solvent, the reaction was warmed to 60° C. The nucleophile may be any suitable primary or secondary aliphatic or aromatic amine, or a thiol. In an alternative experiment, the nucleophile was bound to the solid support and treated with an excess of ortho-fluoro-nitrobenzyl derivatives under similar conditions.

General Method 7—reduction of an aromatic nitro group: The resin bound substrate (0.14 mmol) was washed with DMF (2×2 ml) and then suspended in DMF (0.7 ml) to which was added a solution of SnCl$_2$.2H$_2$O in DMF (0.7 ml, 2 M, 1.40 mmol, 10 equiv.). The resin was shaken at r.t. o/n, then washed with DMF (5×2 ml), DCM (3×2 ml) and MeOH (5×2 ml).

General Method 8 preparation and reaction of an acid chloride: Resin bound substrate (0.14 mmol) was washed with DCM (2×2 ml) and then under N$_2$ with dry DCM (2×2 ml). A suspension of the of sugar-acid building blocks (0.42 mmol, 3 equiv.) in dry DCM (2 ml) was treated with triphosgene (42 mg, FW 296.75, 0.14 mmol, 1 equiv.) followed by collidine (0.159 ml, d 0.917, FW 121.18, 1.20 mmol, 8.6 equiv.). An effervescence was observed and a solution formed. After 1 min., this solution was added to the resin bound substrate and the resin was shaken at r.t. for 3 h. The resin was drained and washed with DCM (5×2 ml) and MeOH (3×2 ml).

General Method 9 cleavage of adenosine N-benzoyl group: The adenosine-containing products were treated with saturated ammonia in methanol (4 ml) at rt. o/n. The solvent was removed in vacuo and the product was again treated with sat $NH_3$ in MeOH at r.t. o/n. The solvent was removed in vacuo and compounds purified as described above. In an alternative procedure, 1M hydrazine hydrate in DMF was substituted for methanolic ammonia. The latter procedure is particularly useful for benzoate removal on solid support.

General Method 10—benzimidazole synthesis: Resin bound substrate (approx. 200 mg, 0.14 mmol) was treated with a solution of an aldehyde (5.0 equivalents) in N-methylpyrrolidine (NMP)(4 ml) and heated to 45-50° C. overnight. The resins were subsequently washed with DMF (3×4 mL), DCM (3×4 mL), MeOH (3×4 mL), ether (3×4 mL) and dried in vacuo overnight.

General Method 11—Cesium carboxylate coupling: The cesium salt of the Boc protected amino acid is made by dissolving the amino acid in methanol (5 ml/mmol) and water (0.5 ml/mmol) and adding an aqueous solution of 20% $Cs_2CO_3$ until pH 7 is reached. The solvent is removed in vacuo and the material is freeze-dried overnight to give a white powder. The resin is treated with the cesium salt (5 eq) in dry DMF (4 ml/g of resin) and stirred at 50° C. for 24 hours. The resin is drained and washed with DMF, DMF/$H_2O$ (1:1; ×3), MeOH/$H_2O$ (1:1; ×3) and MeOH (×3) and then dried in vacuo.

General Method 12—Reductive amination: 6 eq of aldehyde is dissolved in TMOF/THF (1:1; 2 ml) and added to the resin (200 mg) and shaken at room temperature for 3-4 hours. The resin is drained and a solution of $NaCNBH_3$ (2 eq) in THF/MeOH/AcOH (9:1:0.1; 2 ml) is added to the resin and shaken overnight at mom temperature. The resin is then drained and washed with THF/MeOH (1:3; ×3, DMF/MeOH (1:3; ×3), DCM/MeOH (1:3; ×3) and DCM.

General Method 13—Urea formation: In a gloved box, the resin is swelled in 10% DIPEA/DCM, a solution of triphosgene (2 eq in 1.2 ml of dry DCM) was added to the resin in two batches and shaken for 1 hour. The resin is washed with dry DCM (1 ml×2) and a solution of the amine (1.1 eq) and DIPEA (2.2 eq) in 1.5 ml of dry DCM was added and shaken for 30 minutes. The resin is drained and washed with DMF (×3), DCM (×3) and MeOH (×3) and dried.

General Method 14 base catalysed ring closure: The resin was treated with a solution of MeOH/$NEt_3$ (9:1; 2 ml) and heated to 60° C. overnight. The resin is drained (collecting the filtrate) and washed with MeOH, (1 ml), DCM (1 ml), MeOH (1 ml) and DCM (1 ml). The filtrates are combined and the solvent removed in vacuo. The process is then repeated.

General Method 15—Thiourea formation: Resin bound substrate was washed under $N_2$ with dry THF (3×30 mL) then thiocarbonyl diimidazole (2.49 g, 14 mmol) in dry THF (70 mL, conc=0.2M) was added and the resin was shaken at rt for 12 h. The resin was filtered, washed with THF (3×30 mL), DMF (2×30 mL), DCM (2×30 ml), DCM/MeOH (30 mL), MeOH (30 mL) and dried in vacuo.

General Method 16—S alkylation of an isothiourea: The reactions were performed in Bodhan Miniblocks. The resin bound thiourea compound resin(200 mg) was washed under $N_2$ with dry DMF (2×2 mL). Alkyl halide $R^1X$ (0.7 mmol) in dry DMF (1 mL) was added followed by DIPEA (1.4 mmol) in dry DMF (1 mL). The resin was shaken at rt for 12 h, then washed with DMF (3×2 mL), DCM (3×2 mL), DCM/MeOH 1:1 (2×2 mL), MeOH (2×2 mL).

General Method 17—bromoacetylation: To bromoacetic acid (7.76 g) in dry DCM (40 mL) was added slowly DIC (4.4 mL) at 0° C. The solution was stirred at 0° C. for 30 mins. The solution was syringed out leaving the precipitated urea.

Resin bound substrate was washed under $N_2$ with dry DMF then swollen in dry DMF (1 mL). The bromoacetic anhydride solution in dry DCM (1 ml) was added and the resin was shaken at rt for 1 hrs. The resin was filtered, washed with dry DMF (3×3 mL) under $N_2$ (glove box) and dry DCM (2×3 mL). Excess DCM was drained applying positive pressure of $N_2$. The resin was carried through the next step immediately.

General Method 18—N-alkylation: Bromoacetylated resin produced by general method 17 is added to a sugar amine building block (5 eq) in DMF (1 mL). The resin wasshaken at rt for 16 h then filtered, washed with DMF, DCM, DCM/MeOH and dried in vacuo.

General Method 19—Dichloro-Nitropyrimidine addition: The resin was swelled in NMP and a solution of 4,6-Dichloro-5-nitropyrimidine (5 eq) and DIPEA (10 eq) in NMP (1 ml/100 mg resin) was added and shaken at room temperature overnight (solution turned deep orange-red). The resin was drained under nitrogen and washed with dry DMF and dry DCM until filtrate is colourless and dried in vacuo.

General Method 20—Nitro reduction: The resin was swelled in DCM (1.5 ml/100 mg) and a solution of $K_2CO_3$ (10 eq) and $Na_2S_2O_4$ (8 eq) in $H_2O$ (0.75 ml/100 mg) was added. Viologen (0.4 eq) was then added turning the solution deep blue. The resin was then shaken vigourously for 72 hours. The resin was then drained and washed with an aqueous solution of 1% AcOH, THF, DMF and DCM and dried in vacuo.

General Method 21—Aldehyde cyclisation: A solution of the aldehyde (5 eq) in NMP with 1% AcOH (800 µl/100 mg resin) was added to the dry resin in a test tube. The tube was sealed but allowed to vent with a needle in the top. The resin was heated at 100° C. overnight. The resin was filtered and washed with DMF, DCM and MeOH and dried in vacuo.

General Method 22—Acid Chloride Acylation:

Resin bound substrate was washed under $N_2$ with dry DCM then swollen in DIPEA (20 eq)/DCM (1 mL). A solution of acid chloride (10 eq) in DCM (1 ml) was added and the resin was shaken at rt for 24 h. The resin was washed with DMF, DMF/MeOH, DCM, DCM/MeOH, MeOH and dried in vacuo.

General Method 23—Reaction with the isocyanates and the resin cleavage: The resin was taken up in DCE and cooled to 0° C. followed by isocyanate (4 eq) addition. After 30 minutes, 10% TFA/DCM was added followed by shaking for 1 hour at room temperature. The resin was filtered and washed with DCM. The filtrate was concentrated under reduced pressure to afford the crude residue.

General Method 24—Biological Assays:

Compounds were tested in vitro as follows.

Recombinant protein kinases, which were expressed as fusion proteins in SF9 insect cells or E. coli, were used for all in vitro assays. The purity and identity of each kinase was checked by SDS-PAGE/silver staining and by western blot analysis with specific antibodies.

All kinase assays except for p38a (see below) were performed in 96-well micro-titre plates. The assay components included assay buffer, ATP, test compound, enzyme and substrate.

The assay for all enzymes (except for the PKC see below contained 60 mM HEPES-NaOH, pH 7.5, 3 mM $MgCl_2$, 3 mM $MnCl_2$, 3 µM Na-orthovanadate, 1 mM DTT, 0.1 µM [$\gamma$-$^{33}$P]-ATP (approx. 5×10$^5$ cpm per well).

The assay for the PKCs contained 60 mM HEPES-NaOH, pH 7.5, 1 mM EDTA, 1.25 mM EGTA, 5 mM $MgCl_2$, 1.32 mM $CaCl_2$, 5 μg/ml Phosphatidylserine, 1 μg/ml 1.2 Dioleyl-glycerol, 1.2 mM DTT, 50 μg/ml $PEG_{20000}$, 0.1 μM $[\gamma\text{-}^{33}P]$-ATP (approx. $5\times10^5$ cpm per well).

Table below details the amounts of enzyme and substrate that were used per well:

| # | Kinase | Screenpool # | Enzyme (ng/50 μl) | Substrate | Substrate (ng/50 μl) |
|---|--------|--------------|-------------------|-----------|----------------------|
| 1 | KIT | 1 | 50 | Poly(Glu, Tyr)$_{4:1}$ | 125 |
| 2 | EGF-R | 4 | 50 | Poly(Glu, Tyr)$_{4:1}$ | 125 |
| 3 | TIE2 | 3 | 100 | Poly(Glu, Tyr)$_{4:1}$ | 125 |
| 4 | PDGF-Ralpha | 3 | 100 | Poly(Glu, Tyr)$_{4:1}$ | 500 |
| 5 | FGF-R1 | 1 | 75 | Poly(Glu, Tyr)$_{4:1}$ | 500 |
| 6 | CDK2/CycA | 2 | 10 | Histone H1 | 250 |
| 7 | MET | 7 | 100 | Poly(Glu, Tyr)$_{4:1}$ | 125 |
| 8 | VEGF-R2 | 2 | 50 | Poly(Glu, Tyr)$_{4:1}$ | 125 |
| 9 | ABL | 1 | 10 | Poly(Ala, Glu, Lys, Tyr)$_{6:2:5:1}$ | 250 |
| 10 | PKC-beta1 | 1 | 13 | Histone H1 | 500 |

The reaction cocktails were incubated at 30° C. for 80 minutes. The reaction was stopped with 50 μl of 2% (v/v) $H_3PO_4$, plates were aspirated and washed twice with 200 μl of $H_2O$ or 0.9% (w/v) NaCl. Incorporation of $^{33}P_i$ was determined with a microplate scintillation counter.

The mitogen-activated protein kinase p38a assays were done in a proprietary microassay NanoCarrier™ 2080 format. In these assays phosphorylation was detected by a phospho-substrate specific monoclonal antibody in an indirect competition assay. The degree of binding of the antibody to the phospho-substrate was measured by fluorescence polarization using 2D-FIDA anisotrophy. In these experiments the final concentration of the enzyme was 1.6 nM and the substrate was 2 μM.

All data is presented as residual activity, which is the activity of the enzyme in the presence of the stipulated concentration of inhibitor or compound. 100% activity is the maximum activity of the enzyme in the absence of any inhibitor or compouound.

In all experiments the Z' value was calculated according to Zhang et al (J-H Zhang, T. D. Y Chung, K. R. Oldenburg (1999) Journal of Biomolecular Screening 4:67-73) using the standard deviations and mean values of the positive and negative controls.

$$Z'=1-(3*Stdev_{neg}+3*Stdev_{pos})/(Mean_{pos}-Mean_{neg})$$

Only data where the Z' value was >0.5 was used.

EXAMPLE 1

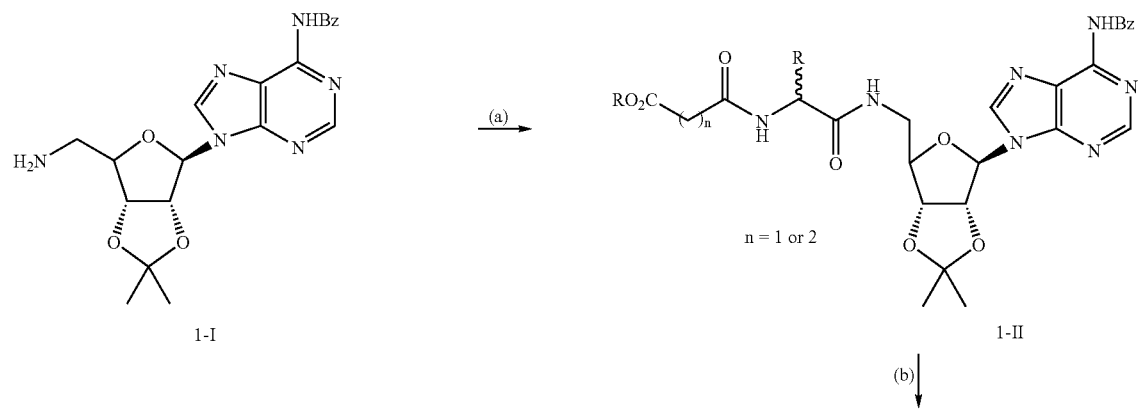

-continued

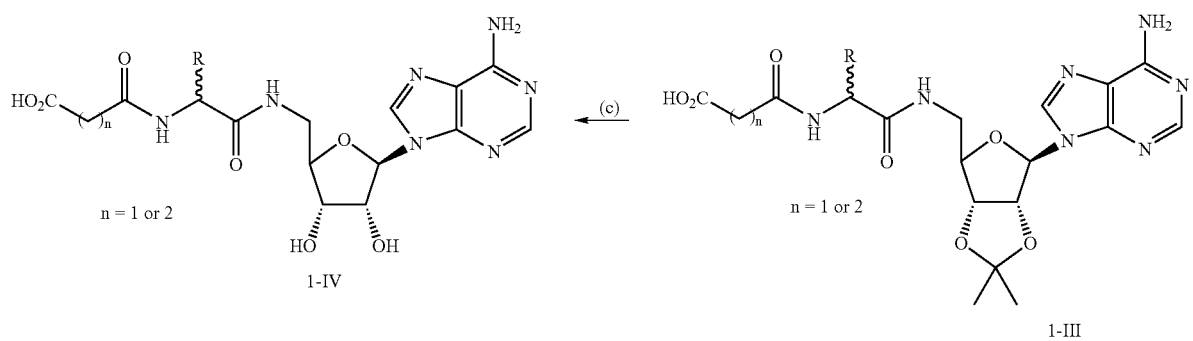

n = 1 or 2
1-IV n = 1 or 2
1-III (1-a) Genereal Method 1, (1-b) General Method 2, (1-c) General Method 3.

Analysis of Some Typical Example Compounds

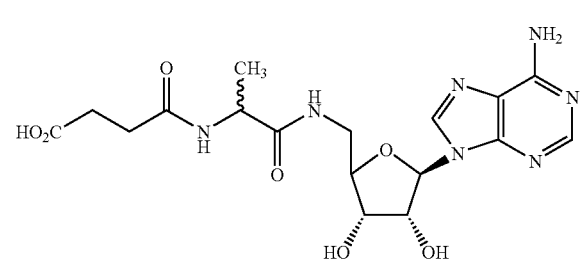

4

Isomer A: proton (400 MHz: DMSO) 2.38 (dt, J 5.0, 6H, CH₂CH₂), 2.65 (d, J=15.0 Hz, 1H, CH₃), 3.85-3.95 (m, 2H, H2 or H3 or H4), 4.05 (dd, J 3.0, 8.0 Hz, 1H, H5a), 4.10 (dd, J 3.0, 8.0 Hz, 1H, H5b), 4.30 (m, 1H, CH), 4.65 (dd, J 5.0, 5.0 Hz, 1H, H2 or H3 or H4), 5.87 (d, J=4.0 Hz, 1H, H1), 8.30 (s, 1H, ArH), 8.45 (s, 1H, ArH).

Isomer B: proton (400 MHz: DMSO) 2.42 (dt, J 5.0, 6H, CH₂CH₂), 2.75 (d, J=15.0 Hz, 1H, CH₃), 3.85-3.95 (m, 2H, H2 or H3 or H4), 4.05 (dd, J 3.0, 8.0 Hz, 1H, H5a), 4.10 (dd, J 3.0, 8.0 Hz, 1H, H5b), 4.30 (m, 1H, CH), 4.65 (dd, J 5.0, 5.0 Hz, 1H, H2 or H3 or H4), 5.92 (d, J=4.0 Hz, 1H, H1), 8.35 (s, 1H, ArH), 8.50 (s, 1H, ArH).

EXAMPLE 2

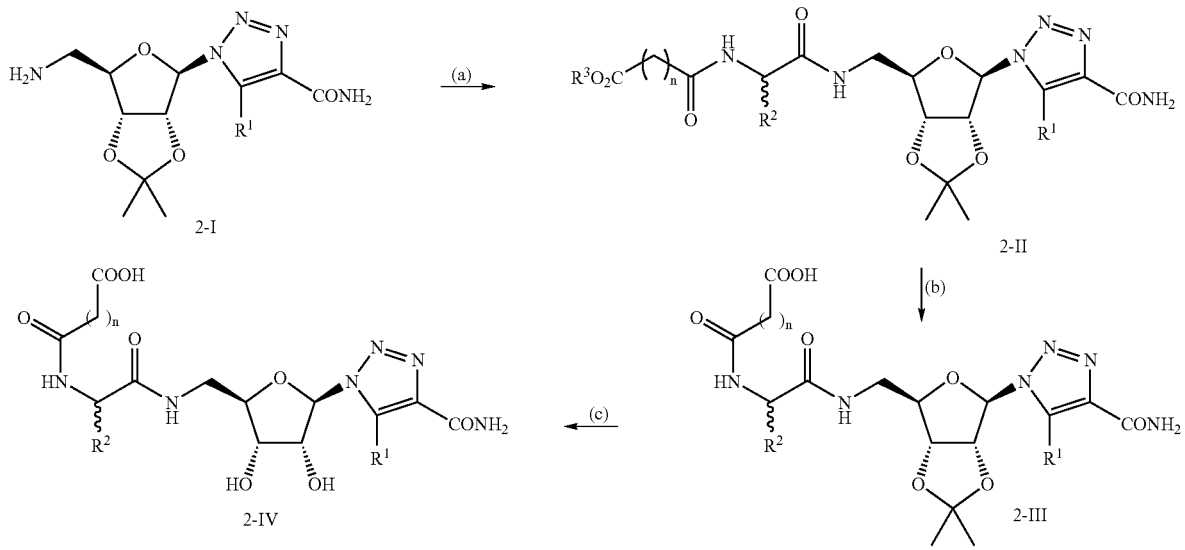

R¹ = phenyl, R¹ = propyl
(2-a) Genereal Method 1, (2-b) General Method 2, (2-c) General Method 3.

Analysis of Some Typical Example Compounds

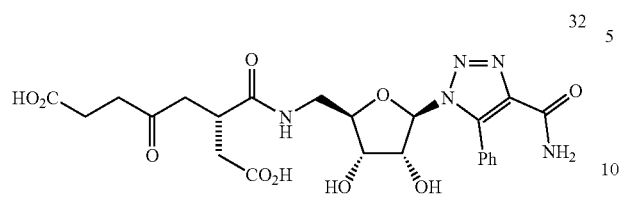
32 proton (400 MHz: D$_2$O) 2.36-2.55 (m, 5H, alkyl H), 2.57-2.76 (m, 1H, alkyl H), 3.31-3.48 (m, 2H, H5), 3.98-4.07 (m, 1H, H4), 4.45-4.56 (m, 2H, H3, NCHCO), 4.69-4.75 (m, 2H, H2), 5.57 (d, J=2.4 Hz, 1H, H1), 7.32-7.40 (m, 2H, PhH), 7.41-7.53 (m, 3H, PhH).

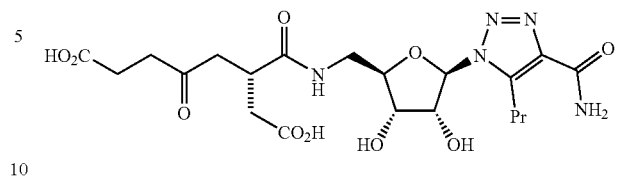
33 proton (400 MHz: D$_2$O) 0.77 (t, J 7.4 Hz, 3H, CH$_2$CH$_3$), 1.42-1.56 (m, 2H, CH$_2$CH$_3$), 2.37-2.53 (m, 5H, alkyl H), 2.58 (dd, J 15.4, 5.4 Hz, 1H, alkyl H), 2.89 (t, J 7.6 Hz, 2H, ArCH$_2$), 3.30-3.46 (m, 2H, H5), 4.07-4.15 (m, 1H, H4), 4.42-4.53 (m, 2H, H3, NCHCO), 4.70-4.75 (m, 2H, H2), 5.87 (d, J 2.8 Hz, 1H, H1).

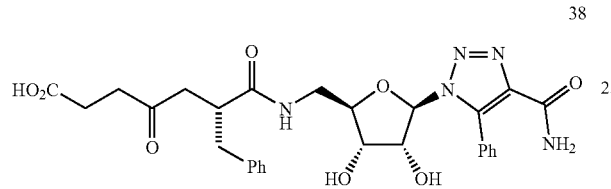
38 proton (400 MHz: D$_2$O) 2.26-2.40 (m, 4H, alkyl H), 2.73 (dd, J 14.0, 8.0 Hz, 1H, CHaPh), 2.88 (dd, J 14.0, 6.2 Hz,1H, CHbPh), 3.30 (dd, J 14.6, 4.6 Hz, 1H, H5a), 3.42 (dd, J 14.6, 3.8 Hz, 1H, H5b), 3.96-4.02 (m, 1H, H4), 4.26 (t, J 5.8 Hz, 1H, H3), 4.36 (t, J 7.4 Hz, 1H, NCHCO), 5.52 (d, J 2.8 Hz, 1H, H1), 7.02-7.20 (m, 5H, PhH), 7.35 (d, J 6.4 Hz, 2H, PhH), 7.42-7.54 (m, 3H, PhH).

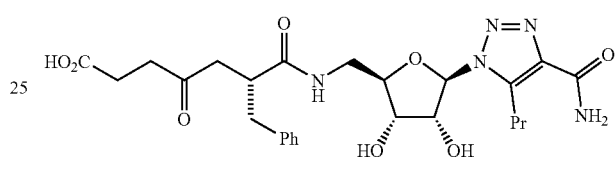
37 proton (400 MHz: D$_2$O) 0.78 (t, J 7.2 Hz, 3H, CH$_2$CH$_3$), 1.38-1.46 (m, 2H, CH$_2$CH$_3$), 2.34 (bs, 4H, alkyl H), 2.70 (t, J 10.2 Hz, 1H, ArCH$_a$), 2.74-2.96 (m, 3H, ArCH$_b$, CH$_2$Ph), 3.25-3.45 (m, 2H, H5), 4.02-4.12 (m, 1H, H4), 4.18-4.25 (m, 2H, H3), 4.29-4.38 (m, 1H, NCHCO), 5.83 (bs, 1H, H1), 6.99-7.20 (m, 5H, PhH).

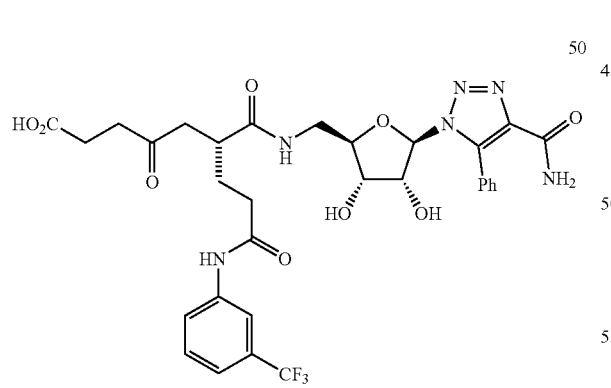
50 proton (400 MHz: D$_2$O) 1.76-1.87 (m, 1H, alkyl H), 1.96-2.08 (m, 1H, alkyl H), 2.30-2.41 (m, 6H, alkyl H), 3.43 (d, J 4.4 Hz, 2H, H5), 4.06 (q, J 5.2 Hz, 1H, H4), 4.26 (dd, J 9.0, 5.2 Hz, 1H, H3), 4.40 (t, J 5.6 Hz, 1H, NCHCO), 4.69-4.74 (m, 1H, H2), 5.54 (d, J 3.2 Hz, 1H, H1), 7.2.8-7.48 (m, 8H, PhH), 7.65 (s, 1H, PhH).

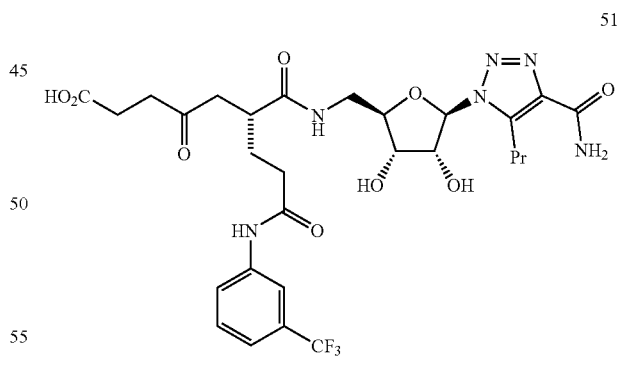
51 proton (400 MHz: D$_2$O) 0.73 (t, J 7.4 Hz, 3H, CH$_2$CH$_3$), 1.36-1.50 (m, 2H, CH$_2$CH$_3$), 1.73-1.85 (m, 1H, alkyl H), 1.88-2.03 (m, 1H, alkyl H), 2.28-2.45 (m, 6H, alkyl H), 2.84 (q, J 7.5 Hz, 2H, ArCH$_2$), 3.42 (d, J 4.4 Hz, 2H, H5), 4.10-4.20 (m, 2H, H3, H4), 4.38 (t, J 5.4 Hz, 1H, NCHCO), 5.84 (d, J 2.8 Hz, 1H, H1), 7.34-7.52 (m, 3H, ArH), 7.65 (s, 1H, ArH).

Some Typical Peptide Arms IIa-IIr Used in Step a of Examples 1 and 2
IIa
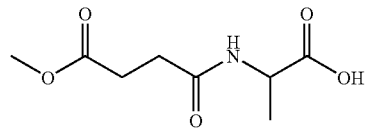
IIb
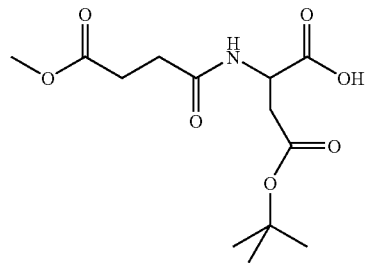
IIc
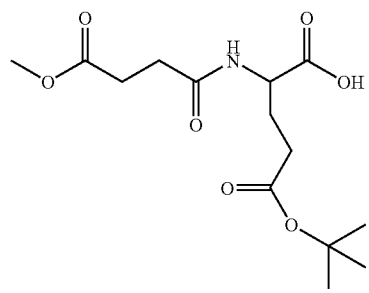
IId
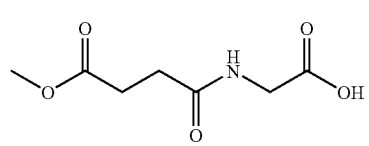
-continued
IIe
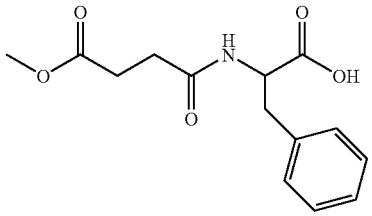
IIf
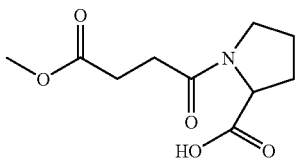
IIg
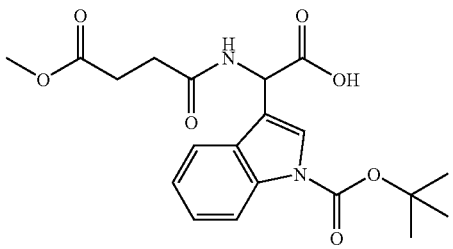
IIh
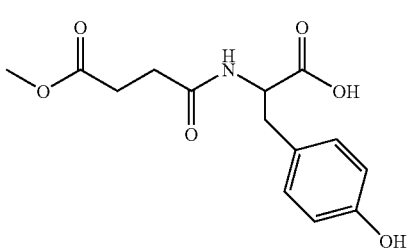

EXAMPLE 3
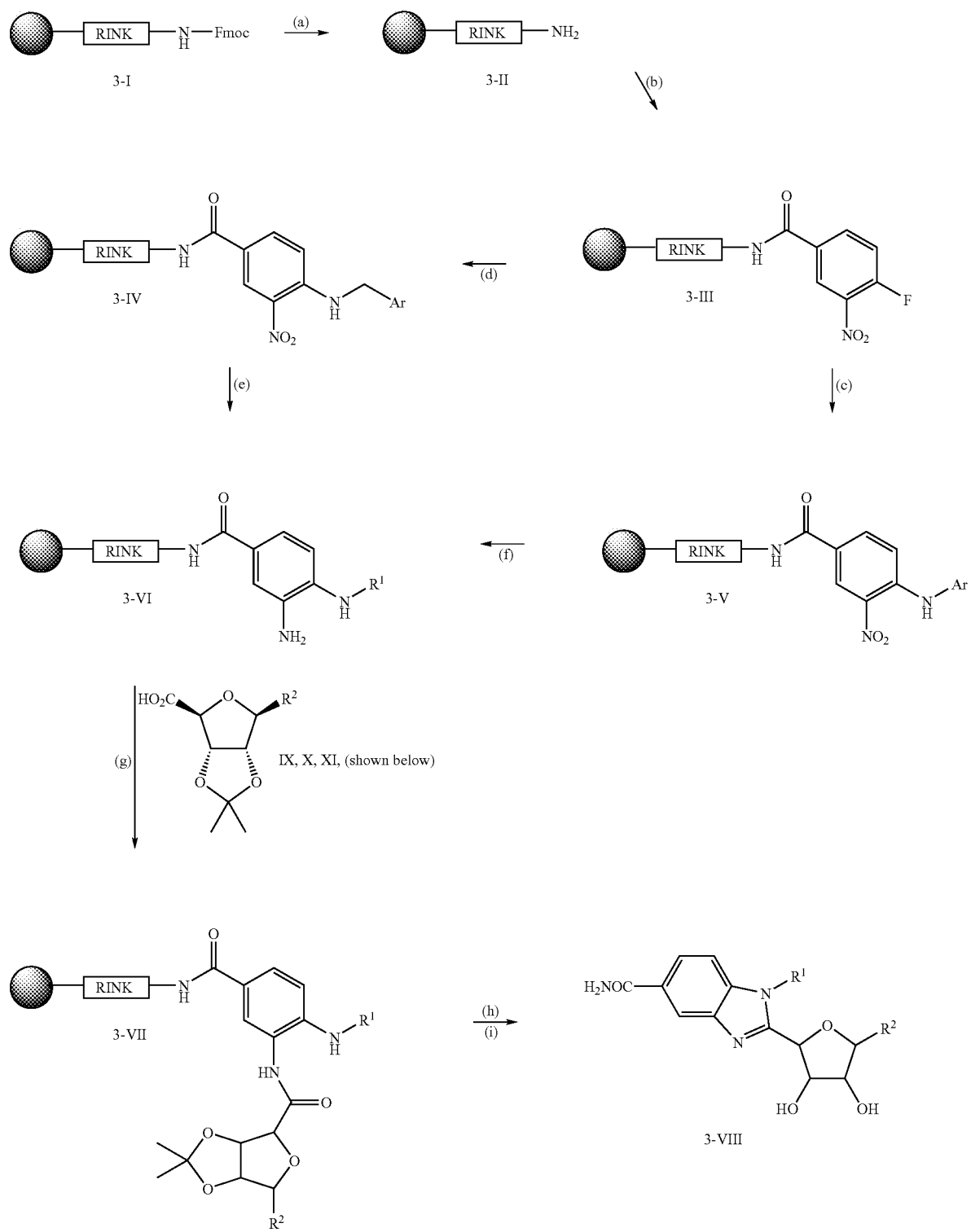
(3-a) General Method 4, (3-B) General Method 5, (3-c) General Method 6 (using reagents ArNH$_2$ and DMSO), (3-d) General Method 6 (using reagents ArCH$_2$NH$_2$ and DMF as solvent), (3-e) General Method 7, (3-f) General Method 7, (3-g) General Method 8, (3-h) General Method 3b, effects ring closure, deprotection and cleavage from resin, (3-i) General Method 9, only required for adenine containing compounds.

Blocks IX, X and XI
EXAMPLE 4
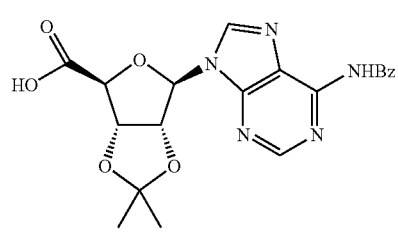
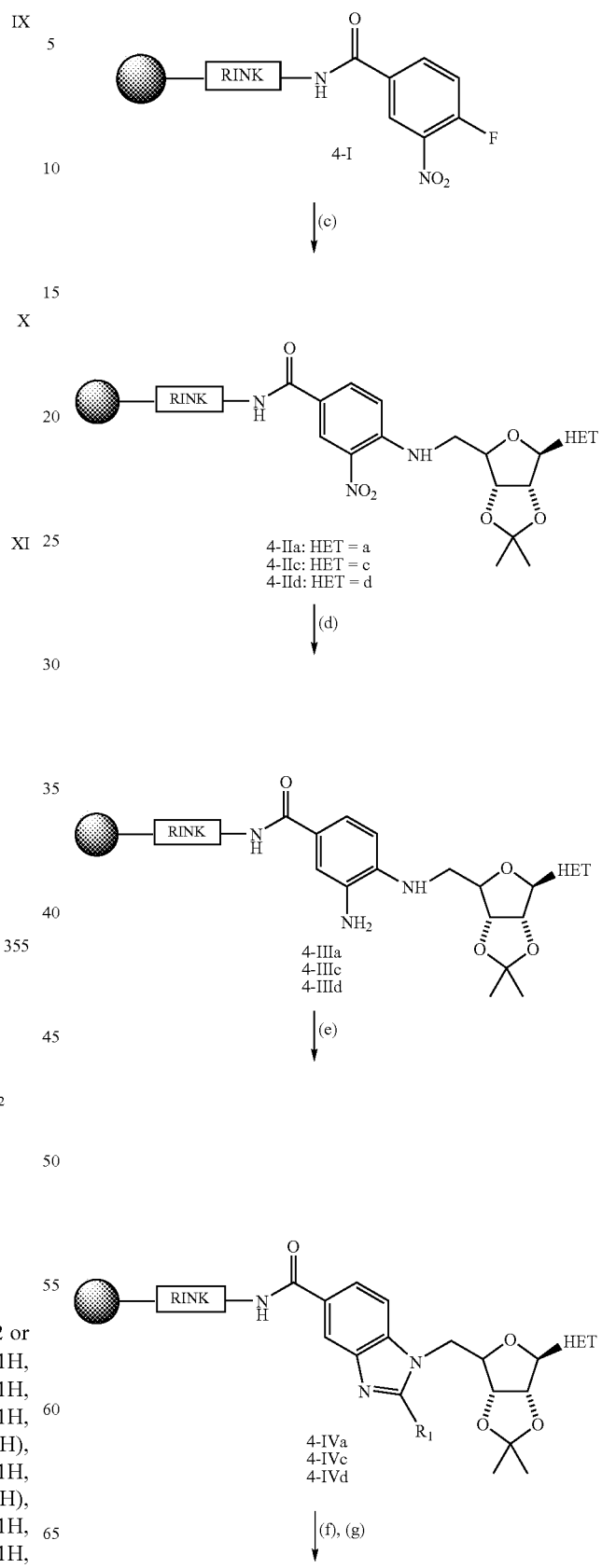
Analysis of a Typical Example Compound
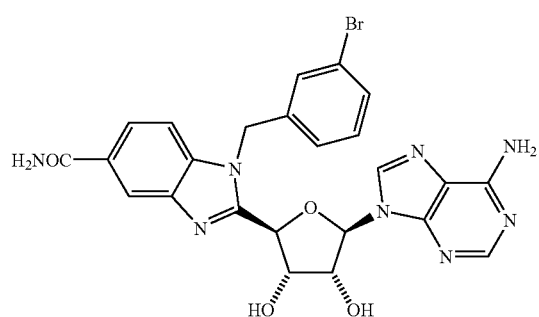
proton (400 MHz: $d_6$ DMSO) 4.92 (q, J 4.4 Hz, 1H, H2 or H3), 4.98 (q, J 5.1 Hz, 1H, H2 or H3), 5.33 (d, J 4.0 Hz, 1H, H4), 5.54 (d, J 16.8 Hz, 1H, CHaPh), 5.62 (d, J 17.2 Hz, 1H, CH$_b$Ph), 5.77 (d, J 5.3 Hz, 1H, OH), 5.80 (d, J 5.4 Hz, 1H, OH), 6.10 (d, J 5.3 Hz, 1H, H1), 6.96 (d, J 7.9 Hz, 1H, PhH), 7.09 (t, J 7.8 Hz, 1H, PhH), 7.24 (bs, 2H, NH$_2$), 7.27 (bs, 1H, PhH), 7.29 (s, 1H, CONH$_a$), 7.36 (d, J 8.9 Hz, 1H, PhH), 7.47 (d, J 8.3 Hz, 1H, ArH), 7.78 (dd, J 8.5, 1.6 Hz, 1H, ArH), 7.98 (bs, 2H, ArH, CONH$_b$), 8.31 (d, J 1.2 Hz, 1H, ArH), 8.37 (s, 1H, ArH).

-continued

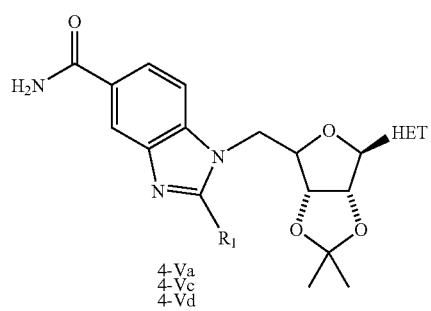

4-Va
4-Vc
4-Vd (4-c) General Method 6 using a sugar amine, (4-d) General Method 7, (4-e) General Method 10, (4-f) General Method 3B, (4-g) General Method 9, only required for adenine containing compounds.

Exemplary Aldehydes Used in Step 4-e

Benzaldehyde, 3-Bromobenzaldehyde, m-Tolualdehyde, 2-Methoxybenzaldehyde, p-Tolualdehyde, 4-Dimethylaminobenzaldehyde, 4-Cyanobenzaldehyde, 1,2,3,6-tetrahydrobenzaldehyde, Indole-3-carboxaldehyde, 2-naphthaldehyde, 3-methyl thiophene-2-carboxaldehyde, cyclohexane carboxaldehyde, pyrrole-2-carboxaldedhyde, phenyl acetaldehyde, 4-(2-pyridyl)benzaldehyde, α,α,α-trifluoro-o-tolualdehyde, 2,5-dimethylbenzaldeyde, 3,5-difluorobenzaldehyde, 2-fluorobenzaldehyde, 4-fluoro-3-(trifluoromethyl)benzaldehyde.

EXAMPLE 5

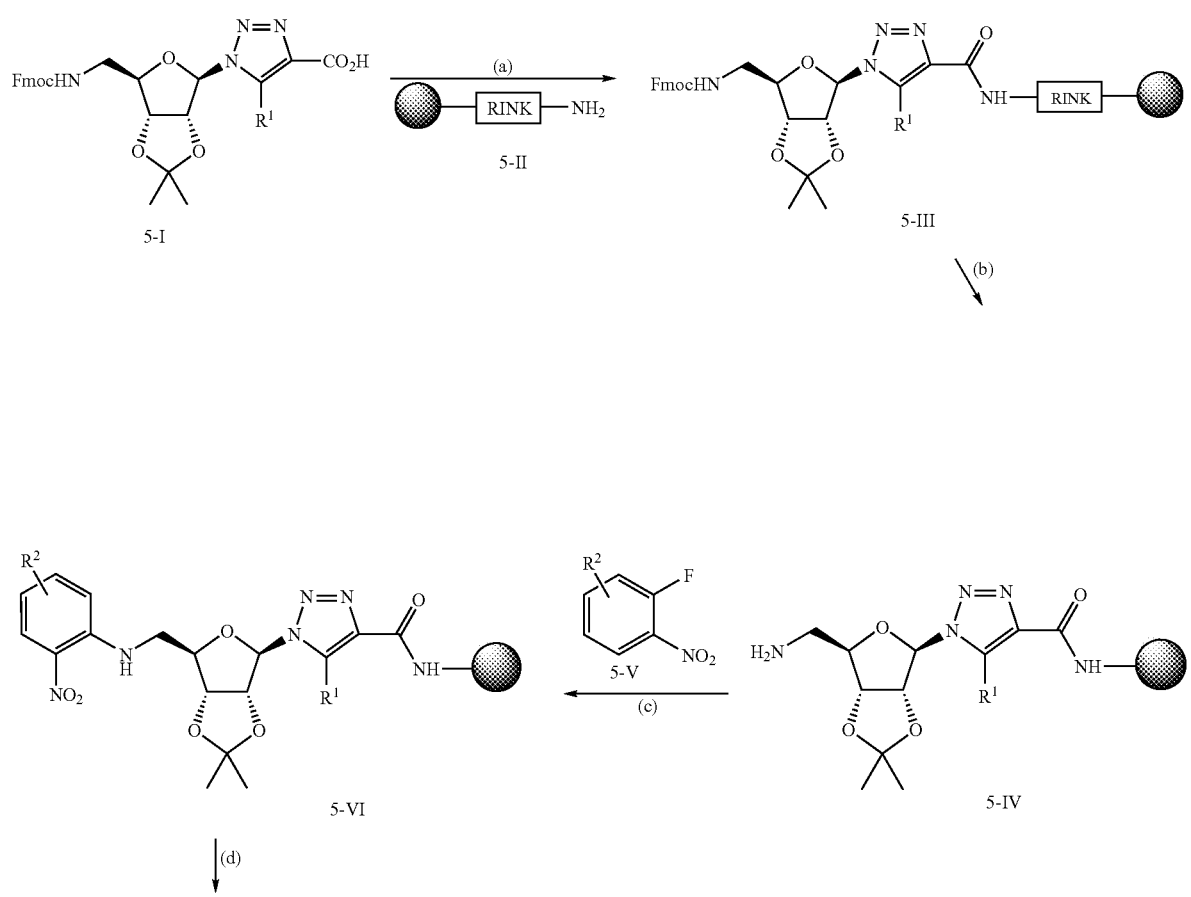

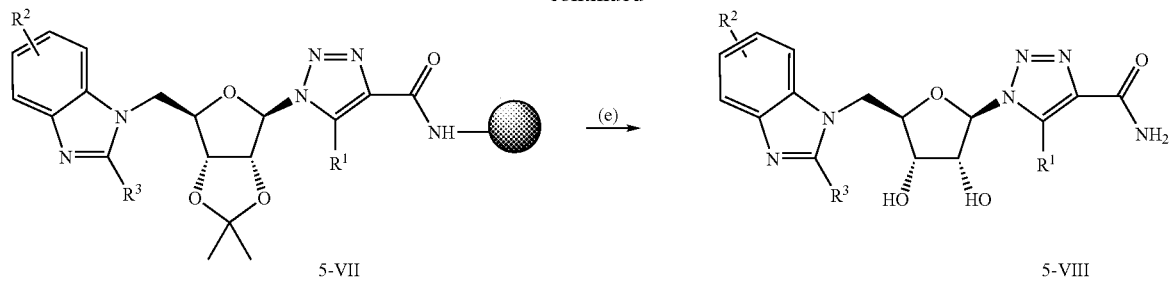

5-VII (5-a) General Method 1, (5-b) General Method 4, (5-c) General Method 6, (5-d) General Method 7, (5-e) General Method 3B

5-VIII

Analysis of Some Typical Example Compounds

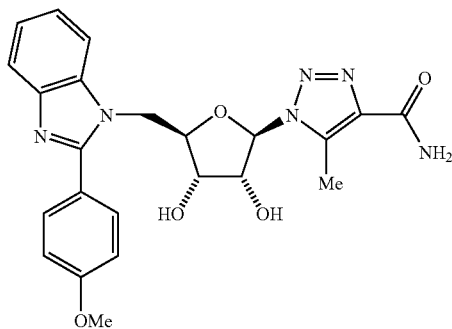

proton (400 MHz: $d_6$ DMSO) 2.41 (s, 3H, CH$_3$), 3.83 (s, 3H, OCH$_3$), 4.34-4.53 (m, 4H, H2, H3, H4, H5a), 4.75 (d, J 13.2 Hz, 1H, H5b), 5.80 (s, 1H, H1), 6.97 (d, J 8.8 Hz, 2H, ArH), 7.39-7.47 (m, 2H, ArH), 7.51 (bs, $_1$H, NHa), 7.57-7.67 (m, 3H, ArH), 7.69-7.75 (m, 1H, ArH), 7.79 (bs, 1H, NHb).

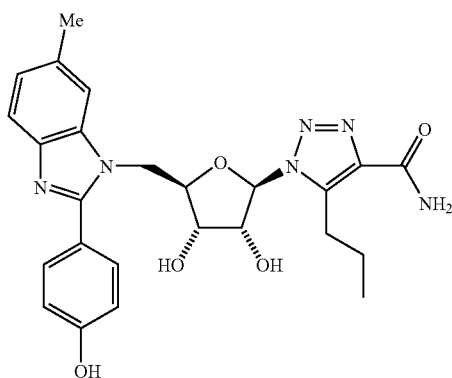

proton (400 MHz: $d_6$ DMSO) 0.77 (t, J 7.4 Hz, 3H, CH$_2$CH$_3$), 1.40 (q, J 7.1 Hz, 2H, CH$_2$CH$_3$), 2.37 (s, 3H, ArCH$_3$), 2.84-2.98 (m, 2H, ArCH$_2$), 4.38-4.52 (m, 4H, H2, H3, H4, H5a), 4.70 (bd, J 14.4 Hz, 1H, H5b), 5.80 (s, 1H, H1), 6.85 (d, J 8.0 Hz, 2H, ArH), 7.27 (bs, 2H, NHa, ArH), 7.48-7.60 (m, 4H, ArH), 7.78 (bs, 1H, NHb).

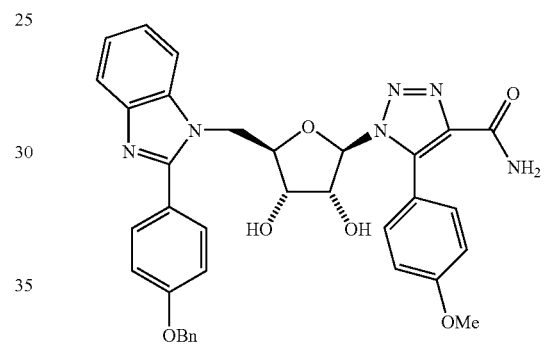

proton (400 MHz: $d_6$ DMSO) 3.77 (s, 3H, OCH$_3$), 4.35-4.46 (m, 3H, H2, H3, H4), 4.57 (bdd, J 14.8, 6.4 Hz, 1H, H5a), 4.84 (bd, J 14.8 Hz, 1H, H5b), 5.05 (d, J 11.6 Hz, 1H, OCHa), 5.11 (d, J 11.6 Hz, 1H, OCHb), 5.34 (s, 1H, H1), 6.96-7.04 (m, 4H, ArH), 7.20 (d, J 8.8 Hz, 2H, ArH), 7.30-7.46 (m, 7H, ArH), 7.54 (bs, 1H, NHa), 7.60 (d, J 8.8 Hz, 2H, ArH), 7.63-7.68 (m, 1H, ArH), 7.71-7.78 (m, 1H, ArH), 7.90 (bs, 1H, NHb).

EXAMPLE 6

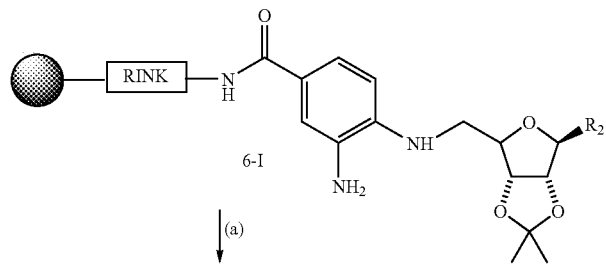

6-I (a)

-continued
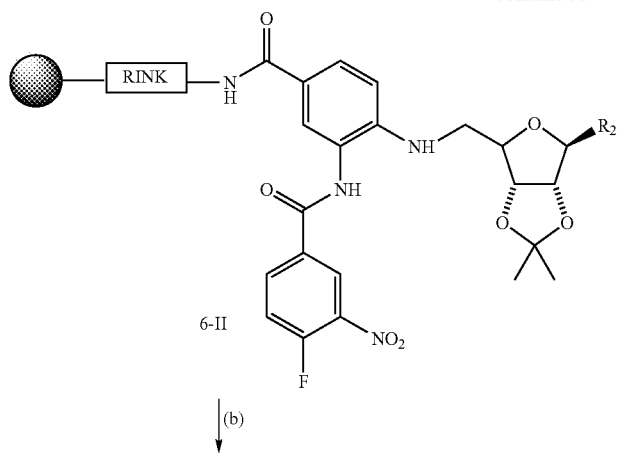
6-II
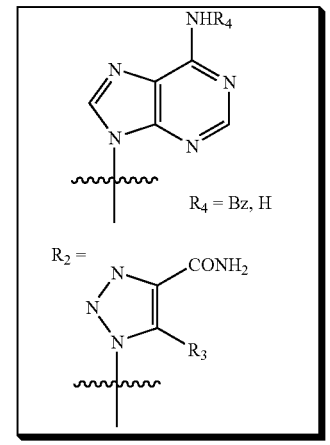
R₄ = Bz, H
R₂ =
(b)
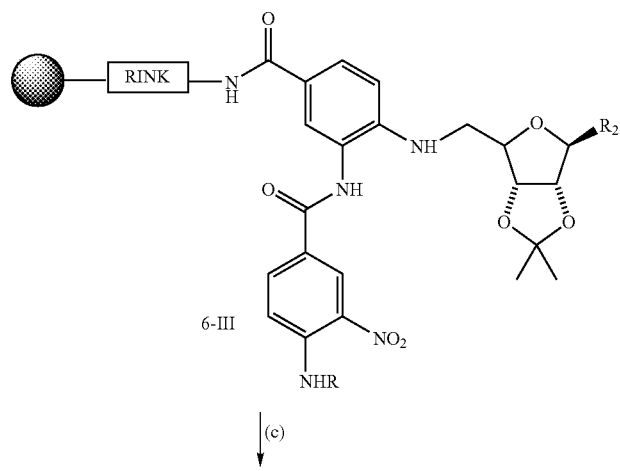
6-III
(c)
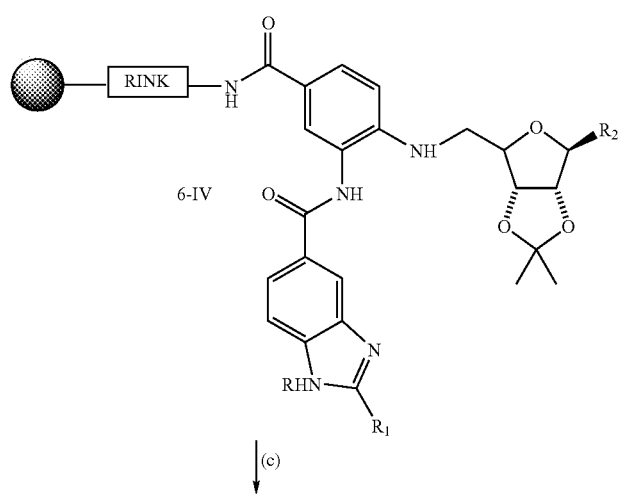
6-IV
(c)

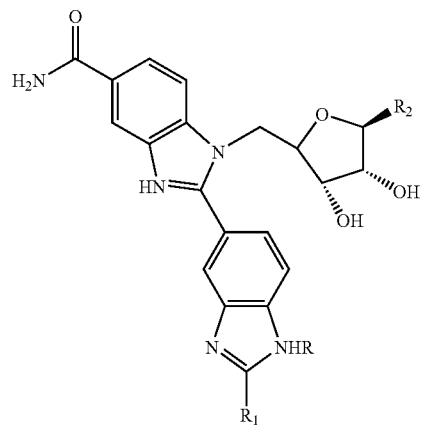
Conditions: (a) general method 5 (b) general method 6; (c) general method 7, general method 10; (d) general method 9 for adenosine containing compounds only, general method 3b.
EXAMPLE 7
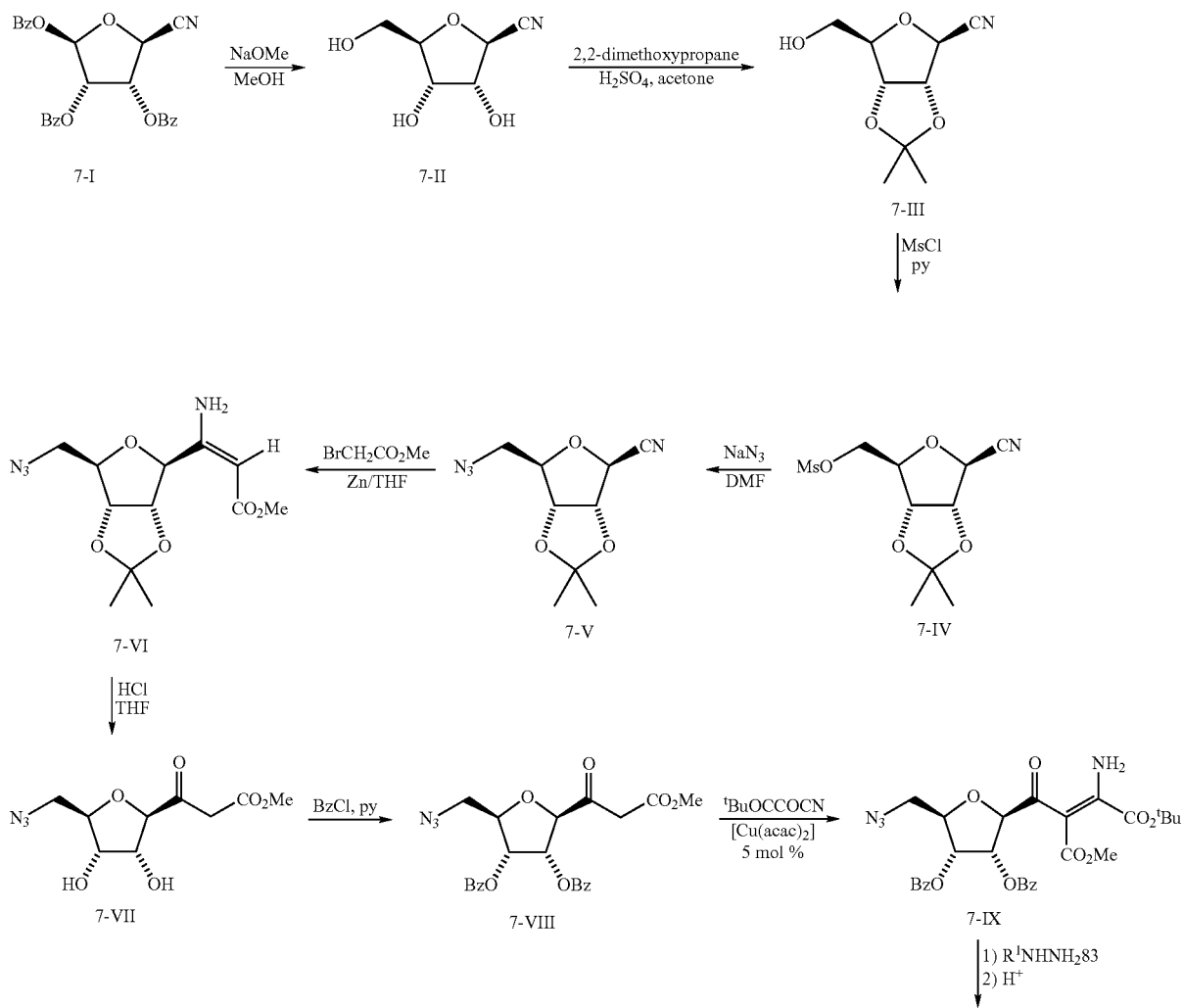

-continued
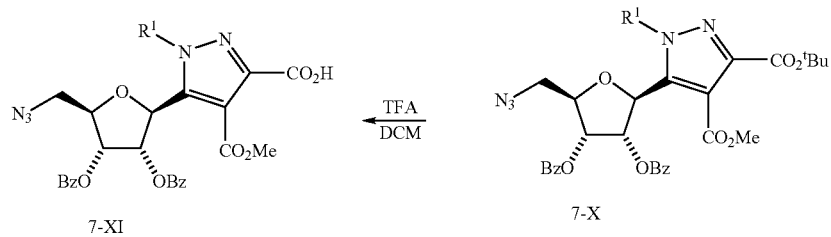
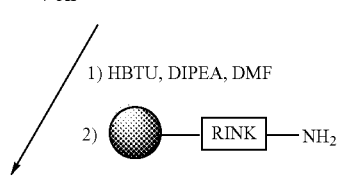
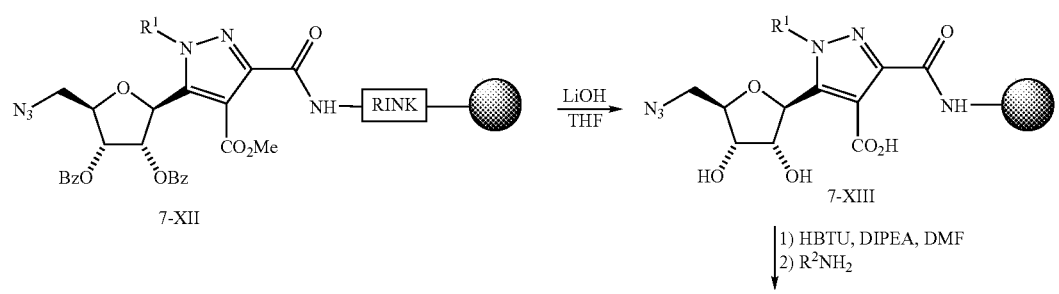
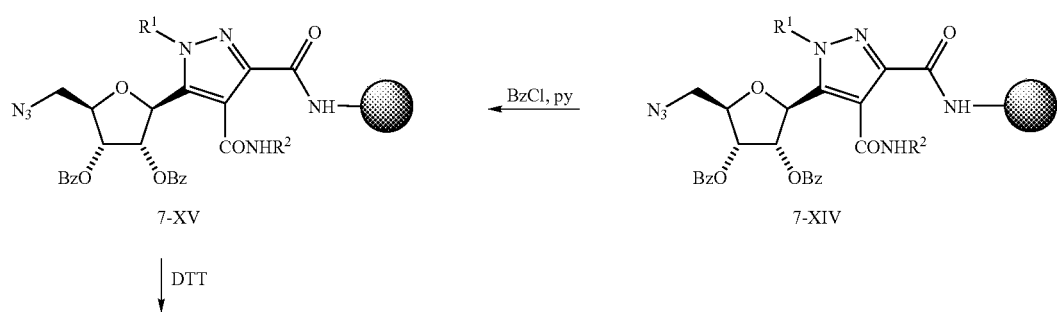
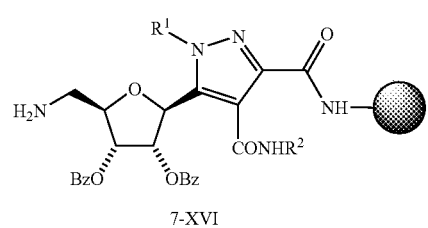

EXAMPLE 8
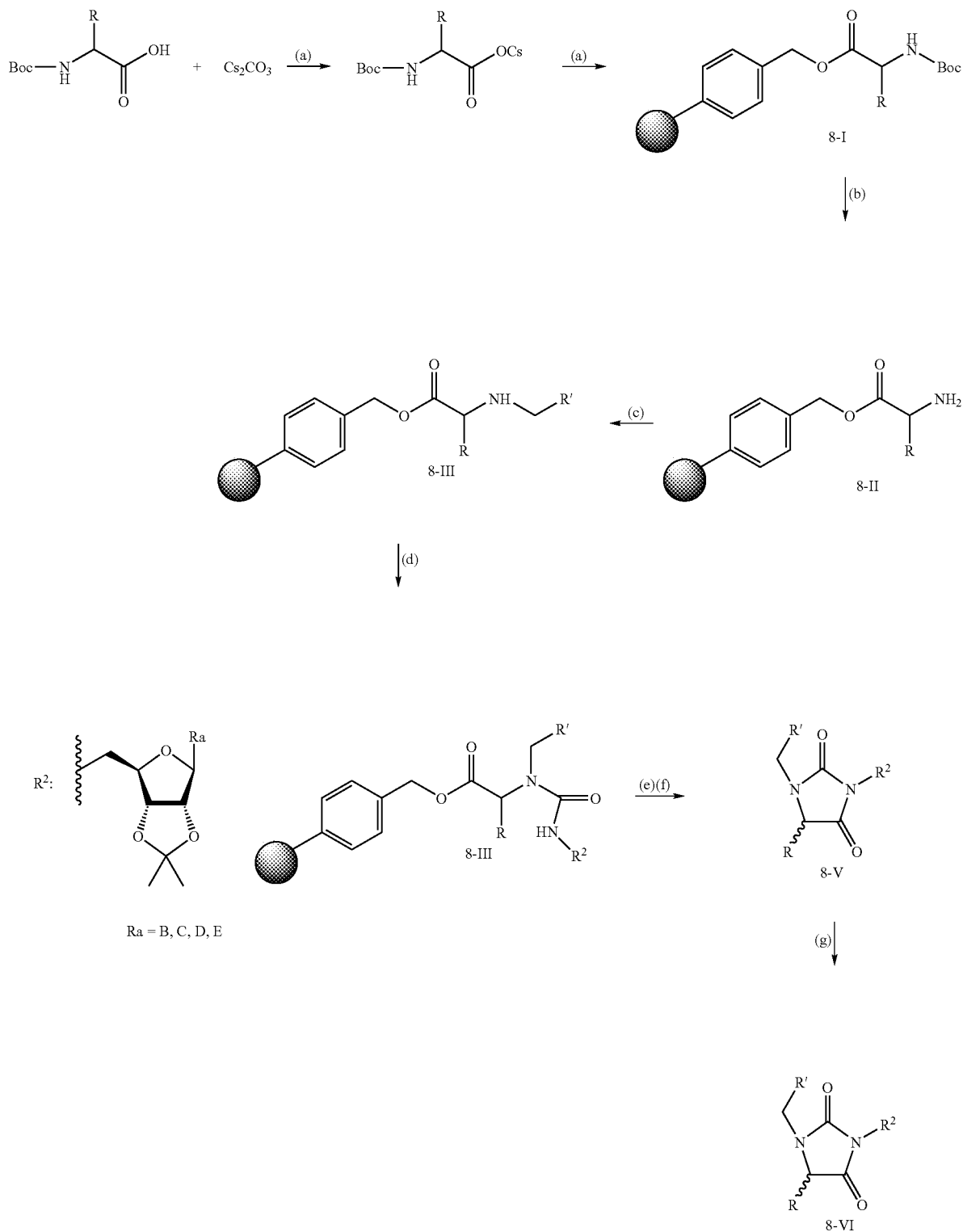
(8-a) General Method 11, (8-b) General Method 3b, (8-c) General Method 12
(8-d) General Method 13, (8-e) General Method 14, (8-f) General Method 3a,
(8-g) General Method 9 for adenosine containing compounds.

Analysis of Some Typical Example Compounds

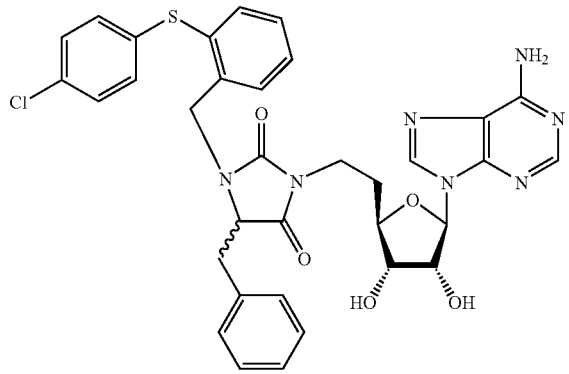

220

Isomer 1:
proton NMR (400 MHz, d$_6$-DMSO): δ: 8.46 (s, 1H, H-6); 8.26 (d, 1H, H-8); 7.93 (s, 2H, NH$_2$); 7.37-7.31 (m, 6 h); 7.15-7.08 (m, 5H); 6.92 (d, 1H, J=6 Hz); 5.86 (d, 1H, J=5.6 Hz, H-1); 4.70-4.64 (m, 2H, containing H-2 and H$_{β1ald}$); 4.39 (d, 1H, J=16 Hz, H$_{βald}$); 4.20 (t, 1H, J=4.8 Hz, H$_α$); 4.04-3.96 (m, 2H, containing H-3, H-5A); 3.59 (d, 1H, J=6.8 Hz, H-4); 2.97 (m, 2H, containing H$_{β1}$, H$_{β2}$).

Isomer 2:
proton NMR (400 MHz, d$_6$-DMSO): δ: 8.42 (s, 1H, H-6); 8.22 (d, 1H, H8); 7.75 (s, 2H, NH$_2$); 7.38-7.30 (m, 6h); 7.17-7.11 (m, 5H); 6.98-6.96 (m, 1H, J=6 Hz); 5.82 (d, 1H, J=5.6 Hz, H-1); 4.72-4.64 (m, 2H, containing H-2 and H$_{β1ald}$); 4.40 (d, 1H, J=16.4 Hz, H$_{β2ald}$); 4.21 (t, 1H, J=4.4 Hz, H$_α$); 4.08 (t, 1H, J=4.4 Hz, H-3); 3.97 (q, 1H, J=6.4, 10.4 Hz, H-5A); 3.65 (dd, 1H, J=6.4, 14.4 Hz, H-4); 3.54 (dd, 1H, J=7.6, 14.4, H-5A); 2.98 (d, 2H, J=4.8 Hz containing H$_{β1}$, H$_{β2}$).

221

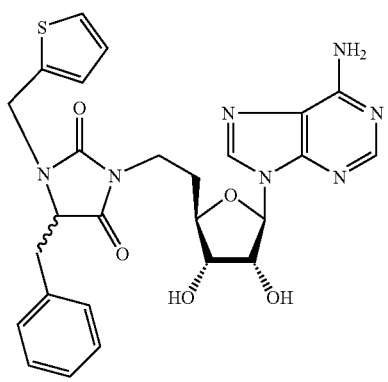

Isomer 1:
proton NMR (400 MHz, d$_6$-DMSO): δ: 8.48 (s, 1H, H-6); 8.27 (s, 1H, H-8); 7.45 (d, 1H, J=4.4 Hz); 7.40 (d, 1H, J=4.8 Hz); 7.24-7.09 (m, 4H); 7.05-7.02 (m, 1H); 6.97-6.91 (m, 2H); 5.84 (d, 1H, J=6.4 Hz, H-1); 4.86 (d, 1H, J=16 Hz, H$_{β1ald}$); 4.66-4.63 (m, 1H, H-2); 4.45 (d, 1H, J=16 Hz, H$_{β2ald}$); 4.21 (t, 1H, J=4.4 Hz, H$_α$); 4.03 (t, 1H, J=3.6 Hz, H-3); 3.98-3.92 (m, 1H, H-5A); 3.19 (q, 1H, J=5.2, 9.2 Hz H$_{β1}$); 3.05-3.01 (m, 1H, H$_{β2}$).

Isomer 2:
proton NMR (400 MHz, d$_6$-DMSO): δ: 8.47 (s, 1H, H-6); 8.26 (s, 1H, H-8); 7.44 (d, 1H, J=4 Hz); 7.41 (d, 1H, J=4.8 Hz); 7.24-7.09 (m, 4H); 7.05-7.02 (m, 1H); 6.97-6.91 (m, 2H); 5.82 (d, 1H, J=6.4 Hz, H-1); 4.88 (d, 1H, J=16 Hz, H$_{β1ald}$); 4.66-4.63 (m, 1H, H-2); 4.45 (d, 1H, J=16 Hz, H$_{β2ald}$); 4.22 (t, 1H, J=4.4 Hz, H$_α$); 4.06 (t, 1H, J=4 Hz, H-3); 3.98-3.92 (m, 1H, H-5A); 3.22 (q, 1H, J=5.2, 9.2 Hz H$_{β1}$); 3.05-3.01 (m, 1H, H$_{β2}$).

202

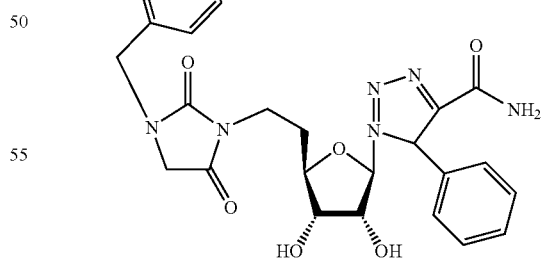

proton NMR (400 MHz, d$_6$-DMSO): δ: 8.37 (s, 1H, H-6); 8.12 (s, 1H, H-8); 7.63 (t, 4H, J=8.4 Hz); 7.46 (t, 2H, J=7.6 Hz); 7.36-7.27 (m, 5H); 5.87 (d, 1H, J=5.6 Hz, H-1); 5.53 (d, 1H, J=6.4 Hz); 5.35 (d, 1H, J=4.8), 4.78 (q, 1H, J=5.2, 10.4 Hz); 4.51 (s, 2H), 4.17-4.08 (m, 2H); 3.92 (s, 2H); 3.82-3.77 (m, 1H); 3.70-3.64 (m, 1H).

proton NMR (400 MHz, d$_6$-DMSO): δ: 7.78 (s, 1H); 7.42 (s, 1H); 7.08 (d, 1H, J=4 Hz); 6.88 (d, 1H, J=3.6 Hz); 5.77 (d, 1H, J=2.8 Hz); 4.62-4.60 (m, 1H); 4.54 (s, 2H); 4.39 (t, 1H J=5.2 Hz); 4.16 (q, 1H, J=6, 11.6 Hz); 3.85 (d, 2H, J=5.2 Hz); 3.62-3.57 (m, 1H); 3.53-3.48 (m, 1H); 3.02-2.90 (m, 3H); 1.54-1.48 (m, 2H); 0.86-0.83 (m, 3H).

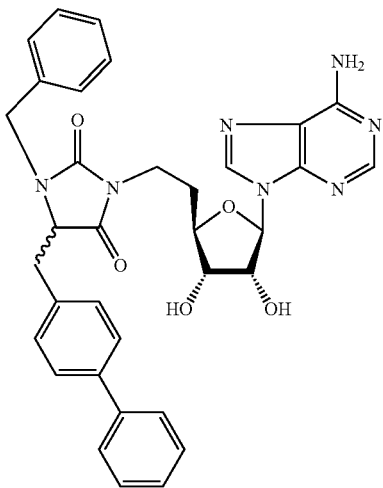

Isomer 1:
proton NMR (400 MHz, d₆-DMSO): δ: 8.40 (s, 1H); 8.18 (s, 1H); 7.62 (s, 2H); 7.56 (d, 2H, J=7.6 Hz); 7.44 (t, 2H, J=3.6 Hz); 7.37 (t, 3H, J=8.4 Hz); 7.27-7.25 (m, 3H); 7.20-7.18 (m, 2H); 7.08 (d, 2H, J=8 Hz); 5.87 (d, 1H, J=5.6 Hz); 4.76 (d, 1H, J=15.6 Hz); 4.67 (t, 1H, J=5.6 Hz); 4.30 (d, 1H, J=15.6 Hz); 4.23 (t, 1H, J=4.4 Hz); 4.04-4.00 (m, 2H); 3.70-3.59 (m, 2H); 3.18-3.04 (m, 2H).

Isomer 2:
proton NMR (400 MHz, d₆-DMSO): δ: 8.39 (s, 1H); 8.20 (s, 1H); 7.81 (s, 2H); 7.61 (d, 2H, J=7.2 Hz); 7.52 (d, 2H, J=8 Hz); 7.45 (t, 3H, J=7.2 Hz); 7.35-7.26 (m, 5H); 7.21 (dd, 4H, J=6.8, 15.6); 5.83 (d, 1H, J=6 Hz); 4.78 (d, 1H, J=15.6 Hz); 4.69 (t, 1H, J=5.2 Hz); 4.30 (d, 1H, J=15.6 Hz); 4.25 (t, 1H, J=4.4 Hz); 4.11 (t, 1H, J=4.4 Hz); 4.02-3.98 (m, 2H); 3.21-3.06 (m, 2H); 3.18-3.04 (m, 2H).

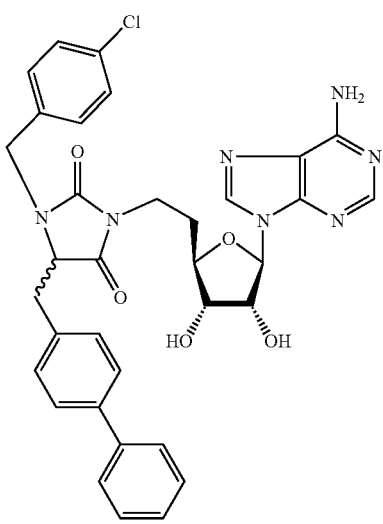

Isomer 1
proton NMR (400 MHz, d₆-DMSO): δ: 8.46 (s, 1H); 8.25 (s, 1H); 7.63 (d, 4H, J=7.2 Hz); 7.52 (t, 2H, J=7.6 Hz); 7.44-7.36 (m, 5H); 7.28 (d, 2H, J=8.4 Hz); 7.16 (d, 2H, J=8.4 Hz); 5.95 (d, 1H, J=5.6 Hz); 4.79-4.73 (m, 2H); 4.40-4.33 (m, 2H); 4.13-4.07 (m, 2H); 3.78-3.70 (m, 2H); 3.26-3.11 (m, 2H).

Isomer 2
proton NMR (400 MHz, d₆-DMSO): δ: 8.26 (s, 1H); 8.07 (s, 1H); 7.55 (d, 2H, J=7.4 Hz); 7.45 (d, 2H, J=8.4 Hz); 7.39 (t, 5H, J=7.6 Hz); 7.30 (d, 2H, J=8 Hz); 7.17 (d, 2H, J=8.4 Hz); 7.11 (d, 2H, J=8.4 Hz); 5.77 (d, 1H, J=5.6 Hz); 5.50 (s, 1H); 5.26 (s, 1H); 4.67-4.63 (m, 2H); 4.25-4.22 (m, 2H); 4.06 (t, 1H, J=8 Hz); 3.95 (q, 1H, J=6.8, 10.4 Hz); 3.67-3.48 (m, 2H); 3.18-2.99 (m, 2H).

EXAMPLE 9

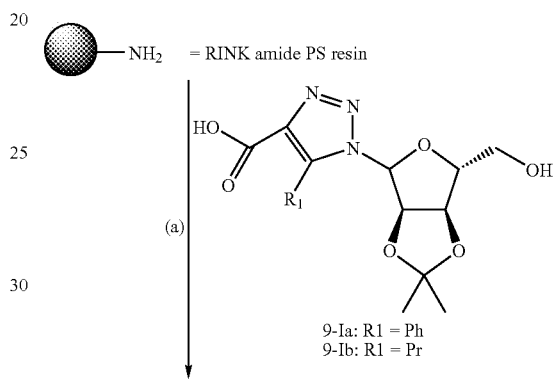

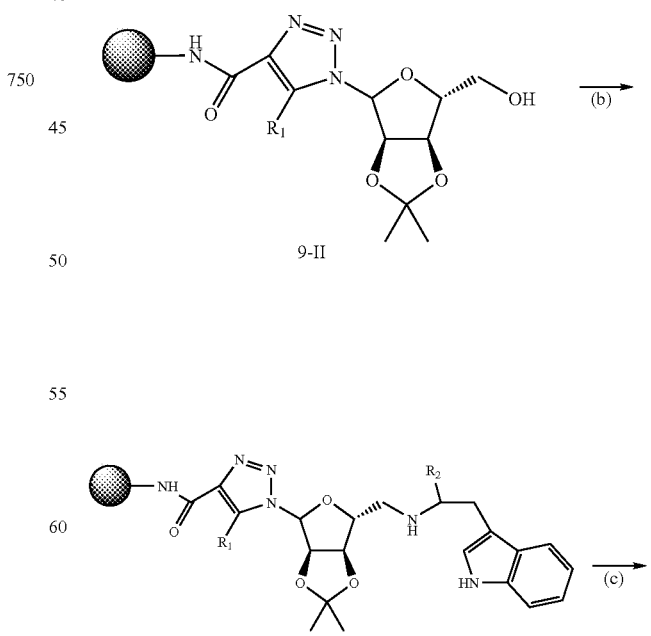

-continued

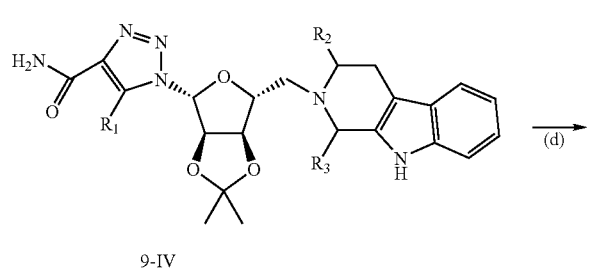

9-IV

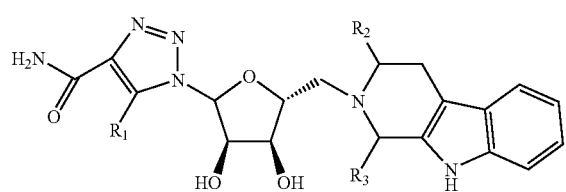

9-V

Conditions: (a) general method 1; (b) (i) MsCl, DCM, (ii) Tryptamine derivative, DMF (c) R₃CHO, 25% TFA/DCM, rt; (d) general method 3b.

EXAMPLE 10

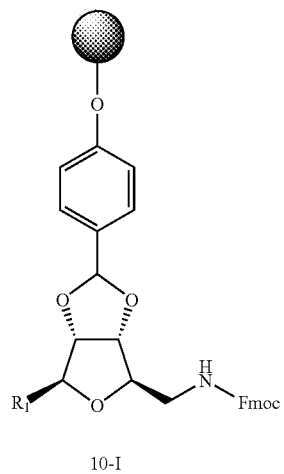

10-I

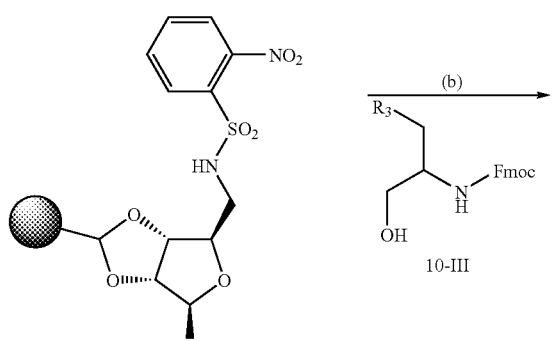

10-II

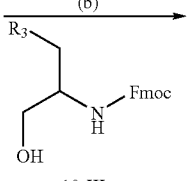

10-III

-continued

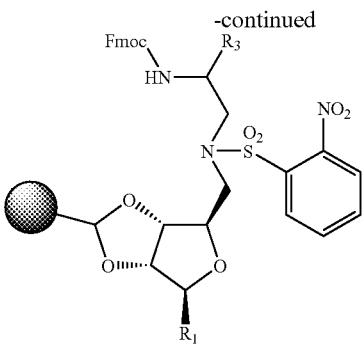

10-IV

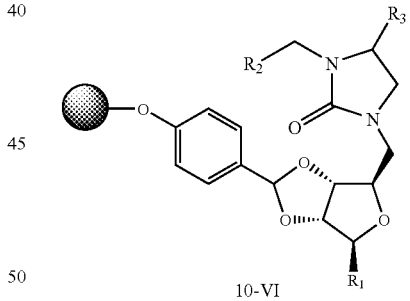

10-V

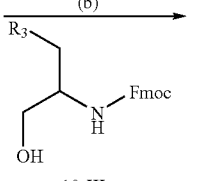

10-VI

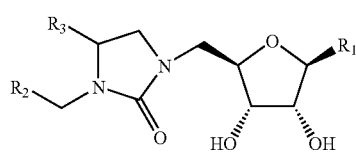

10-VII

Conditions: (a)(i) general method 4, (ii) o-nitrobenzenesulfonyl chloride, DCM DIPEA, 3 hours, RT; (b) PPh₃, aminoalcohol, DEAD, 24 hr; (c)(i) general method 4, (ii) general method 12; (d)(i) Na⁺PhS⁻, DMF, 12 hours, RT (ii) general method 13 where the amine is intramolecular, (e) general method 3b.

EXAMPLE 11
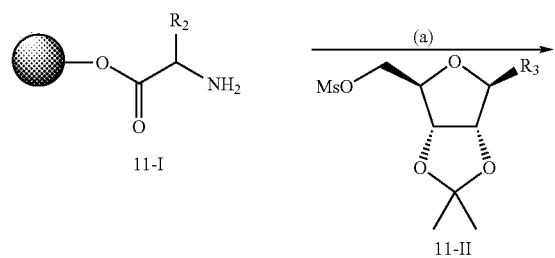
11-I    11-II
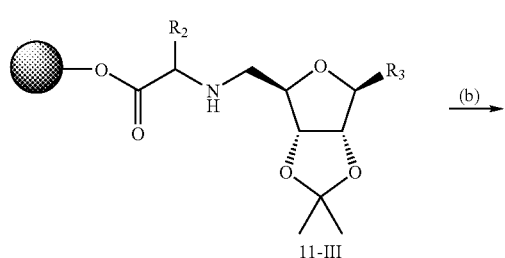
11-III
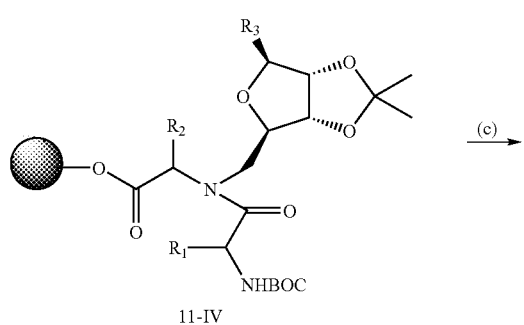
11-IV
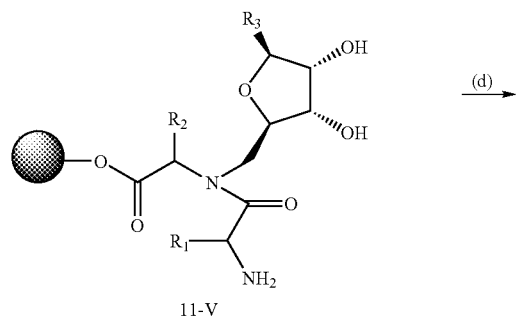
11-V
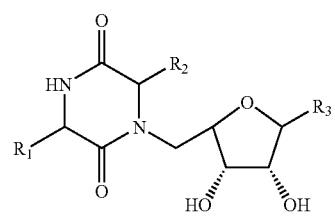
11-VI
Conditions: (a) DMF, DIPEA; (b) general method 1; (c) general method 3b; (d) reflux in toluene.
EXAMPLE 12
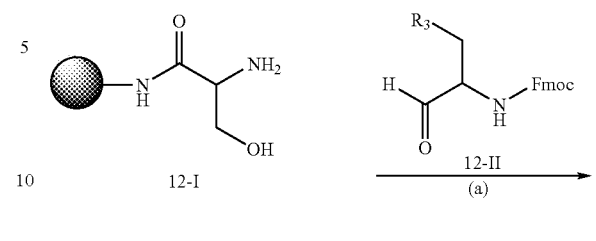
12-I    12-II
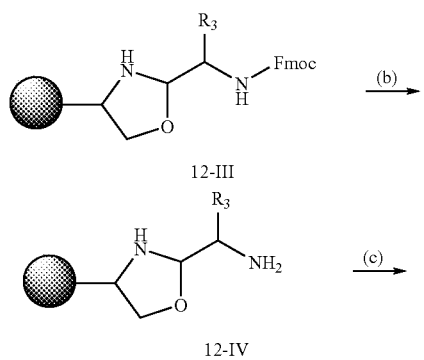
12-III
12-IV
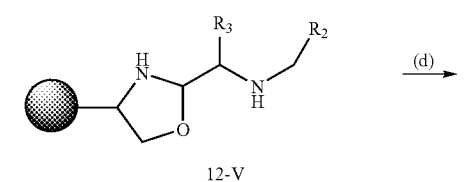
12-V
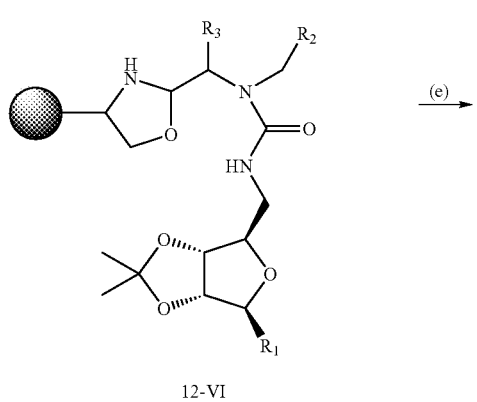
12-VI
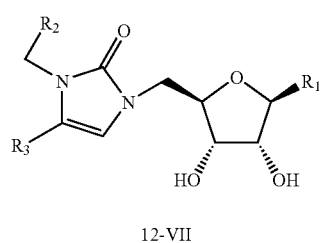
12-VII
Conditions: (a) aldehyde, TMOF/THF; (b) general method 4; (c) general method 12; (d) (i) Na$^+$PhS$^-$, DMF, (ii) general method 13 where the second amine is intramolecular; (e) general method 3b

EXAMPLE 13
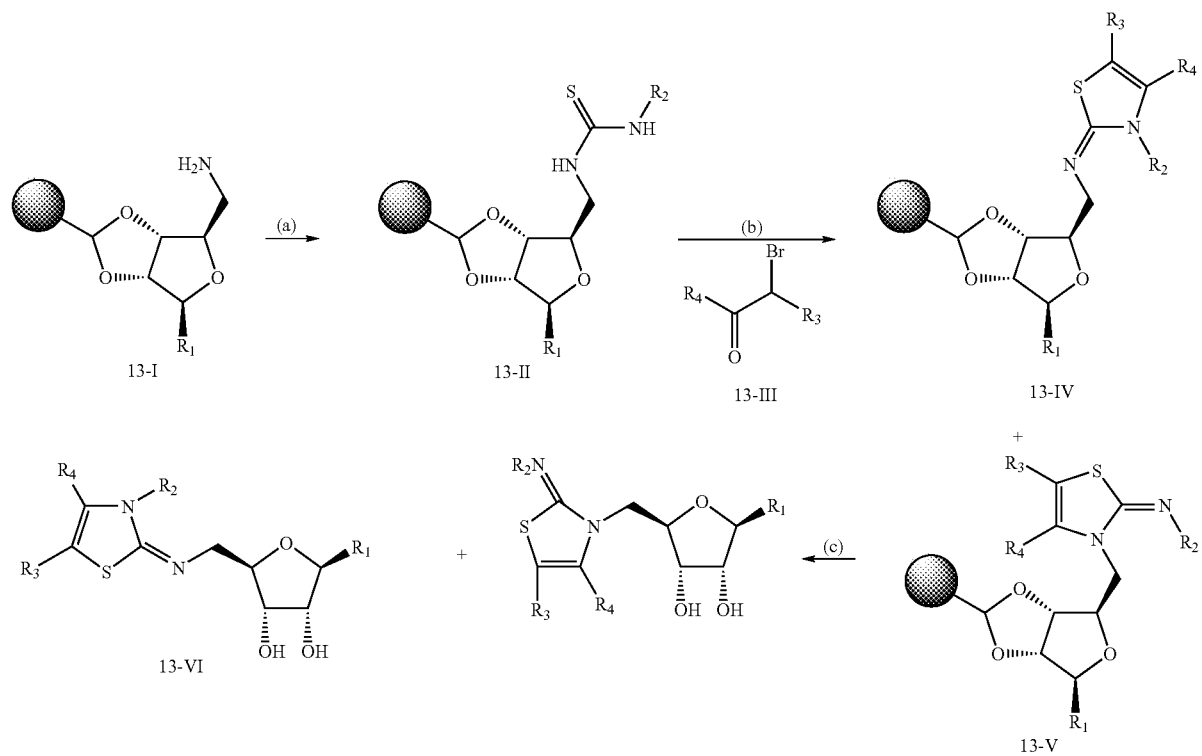
Conditions: (a) R2-Isothiocyanate, DCM; (b) Bromoketone, DMF; (c) general method 3b
EXAMPLE 14
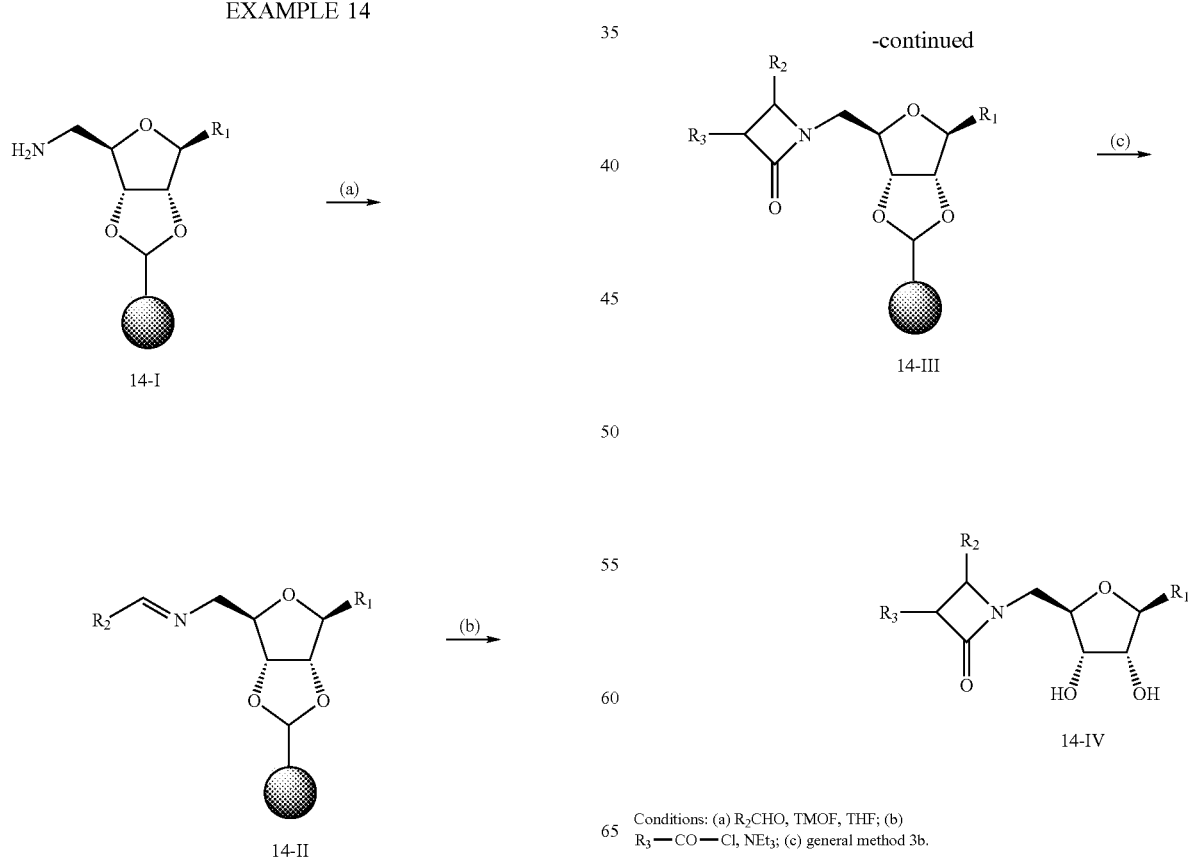
Conditions: (a) $R_2CHO$, TMOF, THF; (b) $R_3$—CO—Cl, $NEt_3$; (c) general method 3b.

EXAMPLE 15
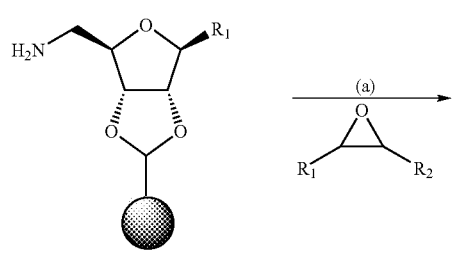
15-I
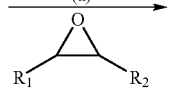
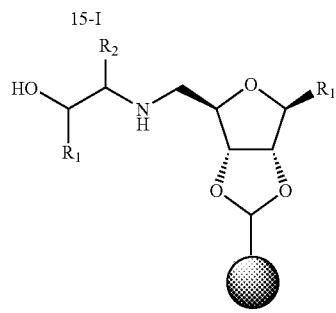
15-II
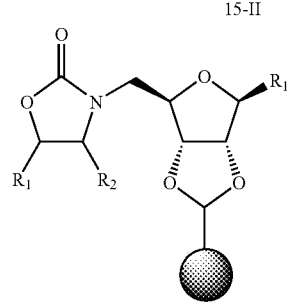
15-III
15-IV
Conditions: (a) Epoxide, DIEA, DMF; (b) CDI, DCM; (c) general method 3b.
EXAMPLE 16
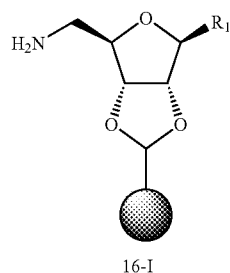
16-I
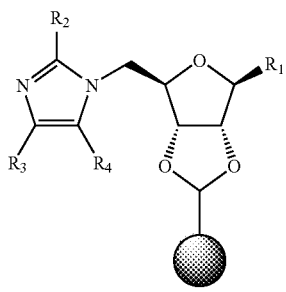
16-II
16-III
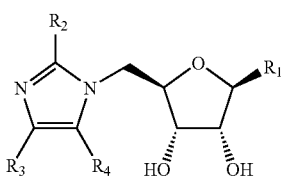
eg:                                    Etc
Conditions: (a) $R_3$—CO—CO—$R_4$, $NH_4OAc$, $R_2$—CHO; (b) general method 3b
EXAMPLE 17
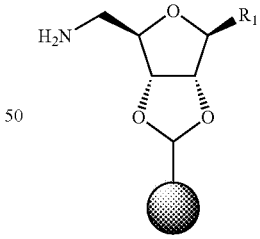
17-I
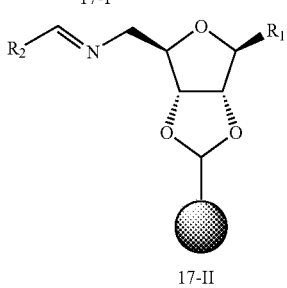 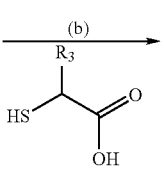
17-II                                    17-III

51

-continued

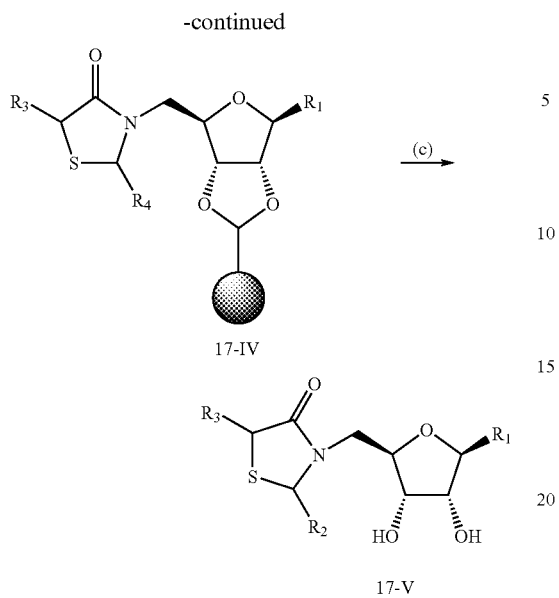

17-IV

17-V

Conditions: (a) R$_2$CHO, TMOF, THF; (b) mercapto acetic acid; (c) general method 3b.

EXAMPLE 18

Intermediate from example 4
(4-III a,c,d)

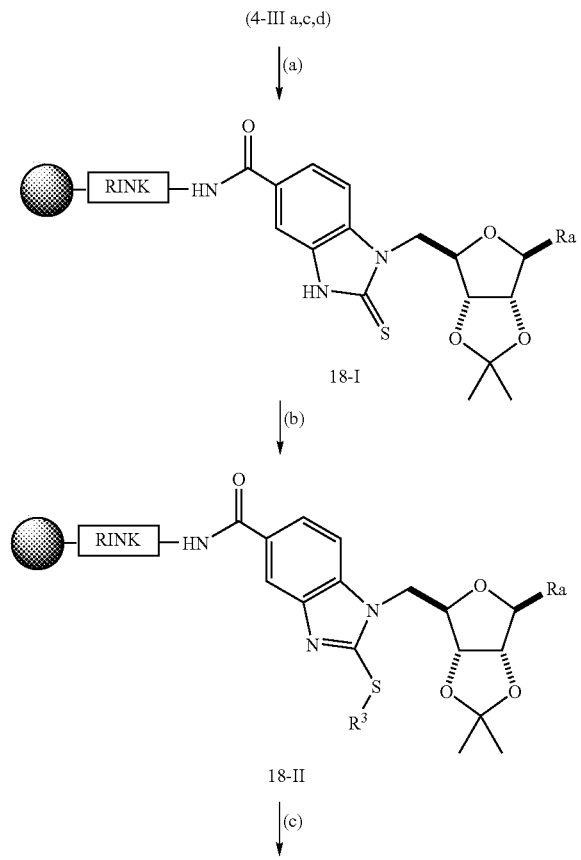

18-I

18-II

52

-continued

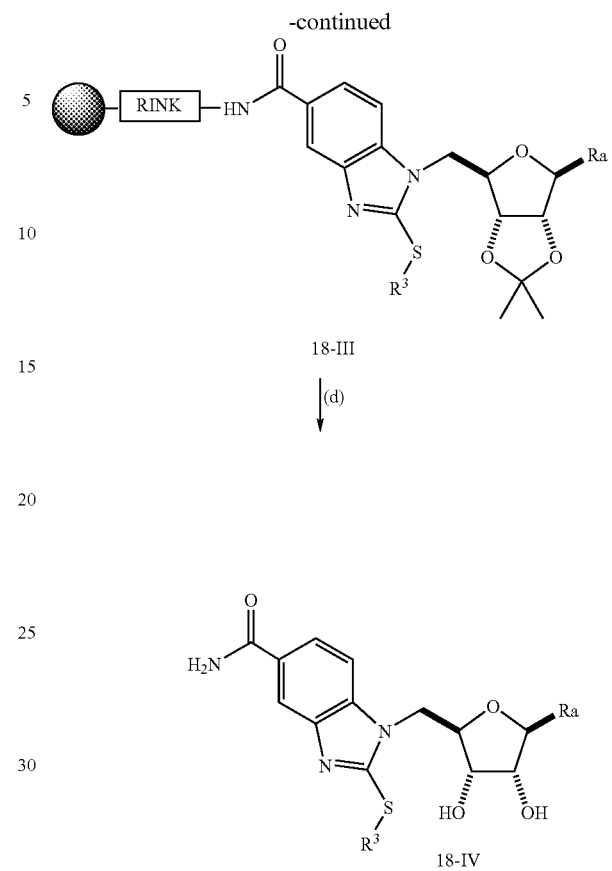

18-III

18-IV (18-a) General Method 15, (18-b) General Method 16, (18-c) General Method 9, hydrazine/DMF conditions for adenosine containing compounds only, (18-d) General Method 3b Exemplary Yield and Crude Product Purity

| Compound | Ra = adenosine Purity of crude cpds (%, by ELSD) | yield (%) |
|---|---|---|
| 86 | 96 | 33 |
| 87 | 92 | 33 |
| 88 | 84 | 31 |
| 89 | 98 | 31 |
| 90 | 97 | 27 |
| 91 | 96 | 46 |
| 92 | 92 | 35 |
| 93 | 87 | 28 |
| 94 | 86 | 34 |
| 95 | 98 | 40 |
| 96 | 85 | 33 |
| 97 | 95 | 35 |
| 98 | 94 | 45 |
| 99 | 97 | 39 |
| 100 | 98 | 39 |

-continued

Ra = adenosine

| Compound | Purity of crude cpds (%, by ELSD) | yield (%) |
|---|---|---|
| 101 | 96 | 40 |
| 102 | 98 | 47 |
| 103 | 63 | 23 |
| 104 | 90 | 38 |
| 105 | 96 | 31 |
| 106 | 95 | 49 |
| 107 | 98 | 46 |
| 108 | 41 | 18 |
| 109 | 89 | 38 |
| 110 | 89 | 41 |
| 111 | 81 | 18 |
| 112 | 20 | 12 |
| 113 | 15 | 8 |
| 114 | 35 | 12 |
| 115 | 95 | 22 |
| 116 | 84 | 42 |
| 117 | 97 | 39 |
| 118 | 88 | 34 |
| 119 | 77 | 25 |
| 120 | 92 | 44 |

Analysis of Some Example Compounds

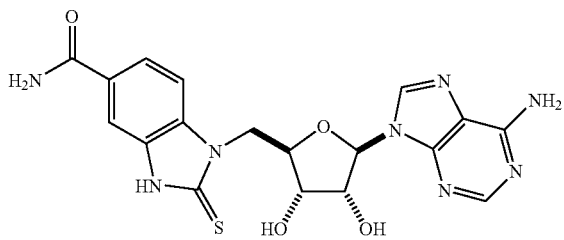

18-1 proton (400 MHz, $d^6$-DMSO): 8.29 (s, 1H, H-8), 8.11 (s, 1H, H-2), 8.00 (d, 1H, J=1.5 Hz, Ar—H), 7.87 (broad s, 1H, NH), 7.61 (dd, 1H, J=1.5, 8.6 Hz, Ar—H), 7.41 (d, 1H, J=8.6 Hz, ArH), 7.30 (broad s, 2H, NH), 7.21 (broad s, 1H, NH), 5.86 (d, 1H, J=5.1 Hz, H'-1), 5.61 (d, 1H, J=6.0 Hz, OH), 5.45 (d, 1H, J=5.4 Hz, OH), 4.72 (qua, 1H, J=5.2 Hz, H'-2 or H'-3), 4.54 (dd, J=15.2, 4.7 Hz, H'-5), 4.47 (dd, 1H, J=15.2, 7.4 Hz, H'-5), 4.31 (qua, 1H, J=4.7 Hz, H'-3 or H'-2), 4.29 (dt, 1H, J=4.7, 7.4 Hz).

carbon (100 MHz, $d^6$-DMSO): 168.7, 156.6, 154.8, 153.2, 149.8, 142.9, 140.4, 139.3, 128.4, 121.9, 119.8, 117.6, 109.8, 88.5, 82.7, 73.5, 71.8, 46.9.

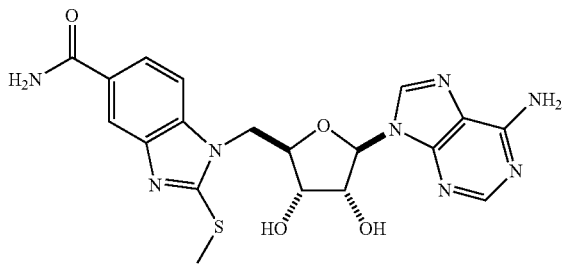

115 proton (400 MHz, $d^6$-DMSO): 8.38 (s, 1H, H-8), 8.15 (s, 1H, H-2), 7.95 (broad s, 1H, NH), 7.64 (d, 1H, J=1.5 Hz, Ar—H), 7.54 (dd, 1H, J=1.5, 8.3 Hz, Ar—H); 7.31 (d, 1H, J=8.5 Hz, Ar—H), 7.30 (broad s, 1H, NH), 7.25 (broad s, 1H, NH), 5.85 (d, 1H, J=6.3 Hz, H'-1), 5.54 (d, 1H, J=6.2 Hz, OH), 5.38 (d, 1H, J=5.1 Hz, OH), 4.82 (qua, 1H, J=5.8 Hz, H'-3 or H'-2), 4.70 (dd, 1H, J=4.6, 13.8 Hz, H'-5), 4.49-4.38 (m, 2H, H'-5+H'4), 4.35 (m, 1H, H'), 2.10 (s, 3H, CH$_3$).

carbon (100 MHz, $d^6$-DMSO): 170.2, 167.9, 156.6, 153.2, 150.0, 140.4, 135.9, 131.1, 129.6, 122.3, 119.8, 110.0, 109.7, 87.8, 82.4, 73.2, 71.9, 46.9, 31.5.

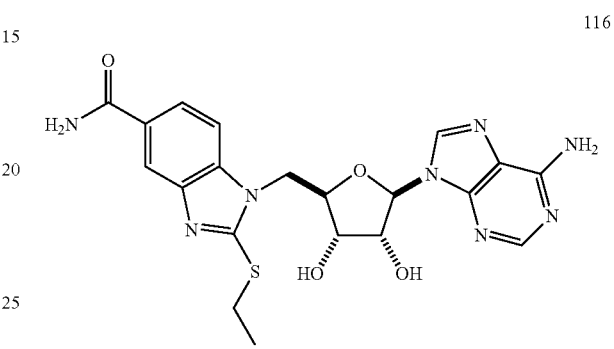

116 proton (400 MHz, $d^6$-DMSO): 8.30 (s, 1H, H-8), 8.11 (s, 1H, H-1), 8.08 (d, 1H, J=1.5 Hz, Ar—H), 7.59 (broad s, 1H, NH), 7.63 (dd, 1H, J=1.5, 8.3 Hz, Ar—H), 7.43 (d, 1H, J=8.3 Hz, Ar—H), 7.31 (broad s, 2H, NH$_2$), 7.22 (broad s, 1H, NH), 5.87 (d, 1H, J=5.0 Hz, H'-1), 5.63 (d, 1H, J=5.8 Hz, OH), 5.46 (d, 1H, J=5.4 Hz, OH), 4.75 (qua, 1H, J=5.0 Hz, H'-2 or H'-3), 4.54 (dd, 1H, J=4.7, 15.3 Hz, H'-5), 4.48 (dd, 1H, J=7.6, 15.3 Hz, H'-5), 4.34 (qua, 1H, J=4.7 Hz, H'-2 or H'-3), 4.25 (dt, 1H, J=4.7, 7.4 Hz, H'-4), 3.24 (qua, 2H, J=7.3 Hz, CH$_2$), 1.32 (t, 3H, J=7.3 Hz, CH$_3$).

carbon (100 MHz, $d^6$-DMSO): 168.7, 156.6, 153.8, 153.2, 149.8, 143.0, 140.4, 139.1, 128.4, 121.9, 119.8, 117.6, 109.9, 88.5, 82.7, 73.4, 71.8, 46.9, 27.2, Yield and Purity of Crude Products Ra=

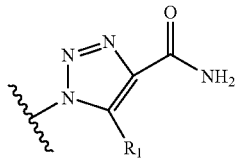

| Compound# | $R^1$ | Purity of Crude cpds (%, by ELSD) | yield (%) |
|---|---|---|---|
| 121 | Ph | 96.9 | 38 |
| 122 | Ph | 94.8 | 5 |
| 123 | Ph | 96.7 | 31 |
| 124 | Ph | 97.8 | 34 |
| 125 | Ph | 50.6 | 38 |
| 126 | Ph | 97.3 | 21 |
| 127 | Ph | 98.3 | 41 |
| 128 | Ph | 97.7 | 26 |
| 129 | Ph | 97.7 | 14 |
| 130 | Ph | 96.7 | 28 |
| 131 | Ph | 91.1 | 23 |
| 132 | Ph | 97.9 | 39 |
| 133 | Ph | 96.9 | 36 |

-continued

Ra=

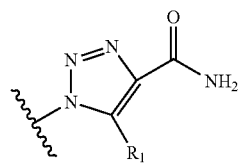

| Compound# | R¹ | Purity of Crude cpds (%, by ELSD) | yield (%) |
|---|---|---|---|
| 134 | Ph | 89.0 | 31 |
| 135 | Ph | 97.5 | 33 |
| 136 | Ph | 96.4 | 22 |
| 137 | Ph | 97.0 | 30 |
| 138 | Ph | 96.7 | 28 |
| 139 | Ph | 84.6 | 23 |
| 140 | Ph | 83.3 | 24 |
| 141 | Ph | 97.1 | 28 |
| 142 | Ph | 97.0 | 27 |
| 143 | Ph | 95.3 | 35 |
| 144 | Ph | 72.8 | 25 |
| 145 | Ph | 88.6 | 30 |
| 146 | Ph | 85.7 | 8 |
| 147 | Ph | 66.3 | 23 |
| 148 | Ph | 68.1 | 25 |
| 149 | Ph | 26.1 | 15 |
| 150 | Ph | 97.7 | 7 |
| 151 | Ph | 99.1 | 5 |
| 152 | Ph | 97.8 | 6 |
| 153 | Ph | 48.4 | 17 |
| 154 | Ph | 95.6 | 26 |
| 155 | Ph | 96.0 | 31 |
| 156 | Ph | 74.50 | 2 |
| 157 | Ph | 7.9 | 3 |
| 158 | Ph | 53.6 | 17 |
| 159 | Pr | 96.4 | 12 |
| 160 | Pr | 98.2 | 37 |
| 161 | Pr | 96.8 | 20 |
| 162 | Pr | 96.9 | 36 |
| 163 | Pr | 97.4 | 19 |
| 164 | Pr | 96.4 | 36 |
| 165 | Pr | 96.7 | 27 |
| 166 | Pr | 97.2 | 24 |
| 167 | Pr | 96.8 | 17 |
| 168 | Pr | 95.0 | 33 |
| 169 | Pr | 82.1 | 15 |
| 170 | Pr | 95.8 | 34 |
| 171 | Pr | 97.0 | 37 |
| 172 | Pr | 97.4 | 23 |
| 173 | Pr | 96.8 | 33 |
| 174 | Pr | 96.9 | 37 |
| 175 | Pr | 96.9 | 41 |
| 176 | Pr | 96.9 | 28 |
| 177 | Pr | 89.9 | 7 |
| 178 | Pr | 98.2 | 35 |
| 179 | Pr | 97.3 | 37 |
| 180 | Pr | 96.4 | 36 |
| 181 | Pr | 93.7 | 28 |
| 182 | Pr | 80.7 | 26 |
| 183 | Pr | 96.6 | 36 |
| 184 | Pr | 97.7 | 36 |
| 185 | Pr | 60.2 | 21 |
| 186 | Pr | 86.9 | 33 |
| 187 | Pr | 39.7 | 15 |
| 188 | Pr | 97.2 | 2 |
| 189 | Pr | 99.5 | 60 |
| 190 | Pr | 98.4 | 4 |
| 191 | Pr | 60.0 | 5 |
| 192 | Pr | 96.0 | 34 |
| 193 | Pr | 96.7 | 36 |
| 194 | Pr | 95.4 | 12 |
| 195 | Pr | 17.0 | 2 |
| 196 | Pr | 80.5 | 11 |

Analysis of a Typical Example Compounds

138

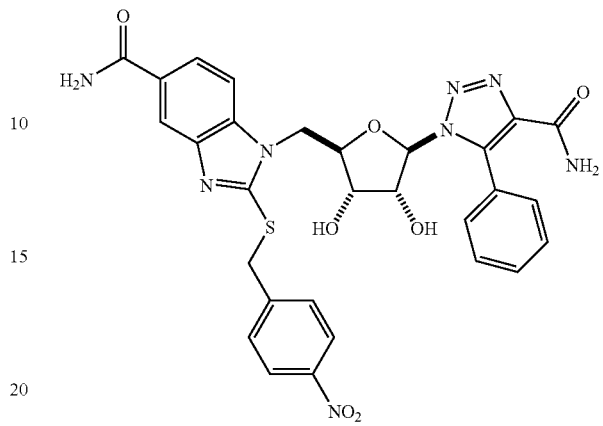

proton (400 MHz, d⁶-DMSO): 8.13 (d, 1H, J=1.3 Hz, Ar—H), 8.09 (d, 1H, J=8.7 Hz, Ar—H), 7.93 (broad s, 1H, NH), 7.86 (broad s, 1H, NH), 7.70 (dd, 1H, J=1.3, 8.4 Hz, Ar—H), 7.64 (d, 1H, J=8.7 Hz, Ar—H), 7.50-7.30 (m, 5H, Ar—H), 7.28 (d, 1H, J=8.5 Hz, Ar—H), 7.25 (broad s, 1H, NH), 5.75 (d, 1H, J=5.48 Hz, OH), 5.53 (d, 1H, J=6.4 Hz, OH), 5.37 (d, 1H, J=1.7 Hz, H'-1), 4.75-4.60 (m, 3H, CH+CH₂), 4.54-4.40 (m, 2H, CH), 4.30-4.23 (m, 2H, CH).

Carbon (100 MHz, d⁶-DMSO): 167.6, 161.1, 152.2, 146.2, 145.3, 141.8, 138.9, 138.2, 138.1, 129.9, 129.7, 129.4, 127.8, 127.7, 125.0, 123.2, 121.3, 116.9, 108.8, 89.7, 82.3, 74.0, 71.8, 46.3, 34.7.

EXAMPLE 19

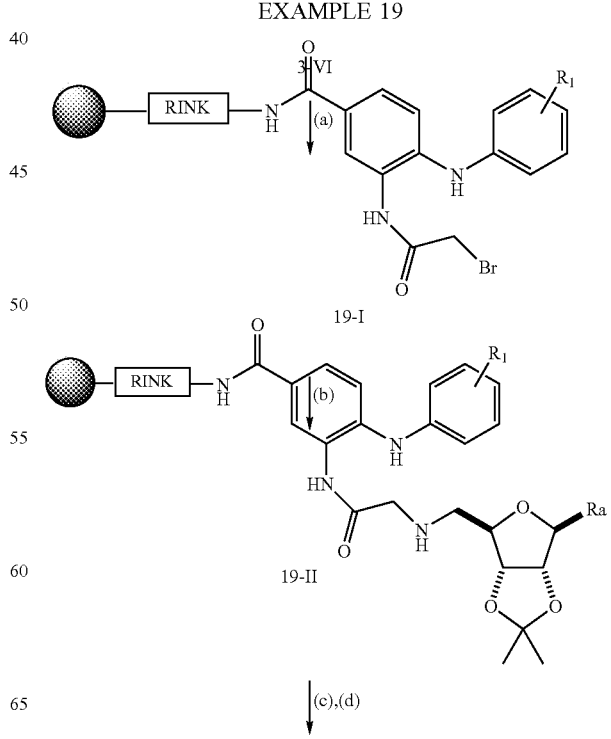

-continued

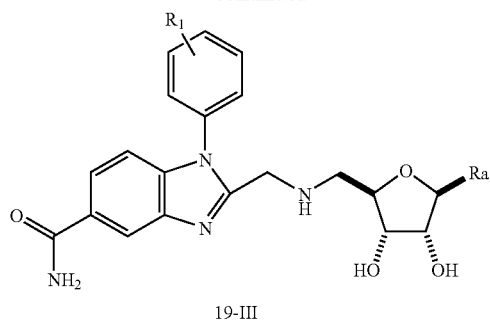

19-III (19-a) General Method 17, (19-b) General Method 18, (19-c) General Method 9 for adenosine containing compounds only, (19-d) General Method 3b.

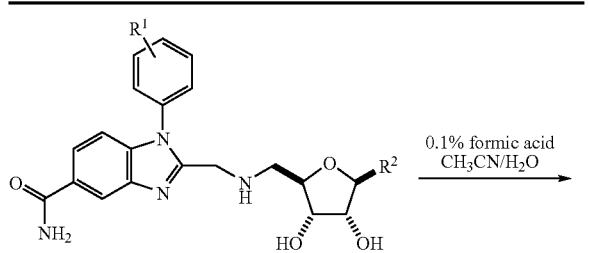

19-III 0.1% formic acid
        CH₃CN/H₂O →

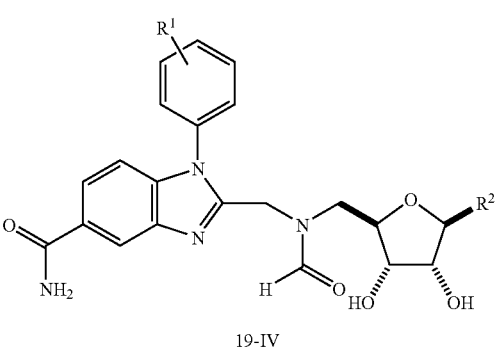

19-IV

| Compound | Retention time, observed mass, yield 2 components 19-III and 19-IV |
|---|---|
| 312 | Rt = 4.24 min (M + H)⁺ = 516 (26%), Rt = 4.75 min (M + H)⁺ = 544 (72%) |
| 313 | Rt = 4.80 min (M + H)⁺ = 550 (3%), Rt = 5.28 min (M + H)⁺ = 578 (72%) |
| 314 | Rt = 4.52 min (M + H)⁺ = 546 (23%), Rt = 4.96 min (M + H)⁺ = 574 (74%) |
| 315 | Rt = 4.70 min (M + H)⁺ = 530 (11%), Rt = 5.17 min (M + H)⁺ = 558 (88%) |
| 316 | Rt = 4.69 min (M + H)⁺ = (2%), Rt = 5.23 min (M + H)⁺ = (19%) |
| 317 | Rt = 5.82 min (M + H)⁺ = 572 (22%), Rt = 6.26 min (M + H)⁺ = 544 (78%) |
| 318 | Rt = 4.81 min (M + H)⁺ = 596 (73%) Rt = 5.40 min (M + H)⁺ = 624 (27%) |
| 319 | Rt = 4.68 min (M + H)⁺ = 530 (2%), Rt = 5.15 min (M + H)⁺ = 558 (98%) |
| 320 | Rt = 5.92 min (M + H)⁺ = 608 (25%), Rt = 6.37 min (M + H)⁺ = 636 (75%) |
| 321 | Rt = 5.97 min (M + H)⁺ = 622 (52%), Rt = 6.48 min (M + H)⁺ = 650 (48%) |
| 322 | Rt = 5.74 min (M + H)⁺ = 592 (43%), Rt = 6.27 min (M + H)⁺ = 620 (57%) |
| 323 | Rt = 5.15 min (M + H)⁺ = 569 (14%), Rt = 5.98 min (M + H)⁺ = 597 (86%) |

-continued

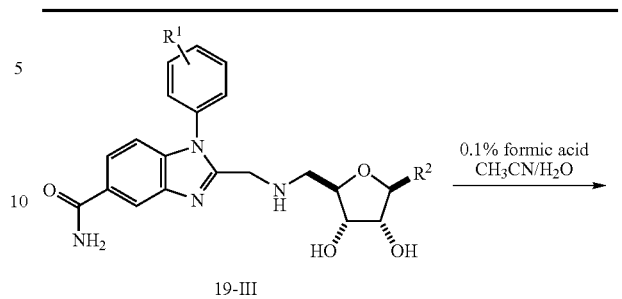

19-III

| Compound | Retention time, observed mass, yield 2 components 19-III and 19-IV |
|---|---|
| 324 | Rt = 5.63 min (M + H)⁺ = 603 (46%), Rt = 6.62 min (M + H)⁺ = 631 (52%) |
| 325 | Rt = 5.34 min (M + H)⁺ = 599 (23%), Rt = 6.20 min (M + H)⁺ = 627 (77%) |
| 326 | Rt = 5.51 min (M + H)⁺ = 583 (38%), Rt = 6.38 min (M + H)⁺ = 611 (62%) |
| 327 | Rt = 5.58 min (M + H)⁺ = 603 (90%), Rt = 6.46 min (M + H)⁺ = 631 (8%) |
| 328 | Rt = 6.54 min (M + H)⁺ = 625 (55%), Rt = 7.41 min (M + H)⁺ = 653 (45%) |
| 329 | Rt = 5.77 min (M + H)⁺ = 647 (31%), Rt = 6.66 min (M + H)⁺ = 677 (55%) |
| 330 | Rt = 5.59 min (M + H)⁺ = 612 (28%), Rt = 6.20 min (M + H)⁺ = 640 (61%) |
| 331 | Rt = 5.51 min (M + H)⁺ = 583 (22%), Rt = 6.31 min (M + H)⁺ = 611 (78%) |
| 332 | Rt = 6.57 min (M + H)⁺ = 661 (42%), Rt = 7.50 min (M + H)⁺ = 689 (58%) |
| 333 | Rt = 6.75 min (M + H)⁺ = 675 (38%), Rt = 7.62 min (M + H)⁺ = 703 (60%) |
| 334 | Rt = 6.56 min (M + H)⁺ = 645 (55%), Rt = 7.38 min (M + H)⁺ = 673 (44%) |
| 335 | Rt = 5.03 min (M + H)⁺ = 535 (17%), Rt = 5.77 min (M + H)⁺ = 563 (82%) |
| 335 | Rt = 5.58 min (M + H)⁺ = 569 (11%), Rt = 6.35 min (M + H)⁺ = 597 (87%) |
| 336 | Rt = 5.26 min (M + H)⁺ = 565 (15%), Rt = 6.0 min (M + H)⁺ = 593 (84%) |
| 337 | Rt = 5.33 min (M + H)⁺ = 5.49 (12%), Rt = 6.04 min (M + H)⁺ = 577 (88%) |
| 338 | Rt = 5.41 min (M + H)⁺ = 569 (79%), Rt = 6.27 min (M + H)⁺ = 597 (5%) |
| 339 | Rt = 6.44 min (M + H)⁺ = 591 (36%), Rt = 7.29 min (M + H)⁺ = 619 (64%) |
| 340 | Rt = 5.67 min (M + H)⁺ = 615 (18%), Rt = 6.46 min (M + H)⁺ = 643 (79%) |
| 341 | Rt = 6.51 min (M + H)⁺ = 591 (8%) |
| 342 | Rt = 5.37 min (M + H)⁺ = 549 (25%), Rt = 6.20 min (M + H)⁺ = 577 (75%) |
| 343 | Rt = 6.54 min (M + H)⁺ = 627 (19%), Rt = 7.40 min (M + H)⁺ = 655 (81%) |
| 344 | Rt = 6.64 min (M + H)⁺ = 641 (30%), Rt = 7.52 min (M + H)⁺ = 669 (69%) |

-continued
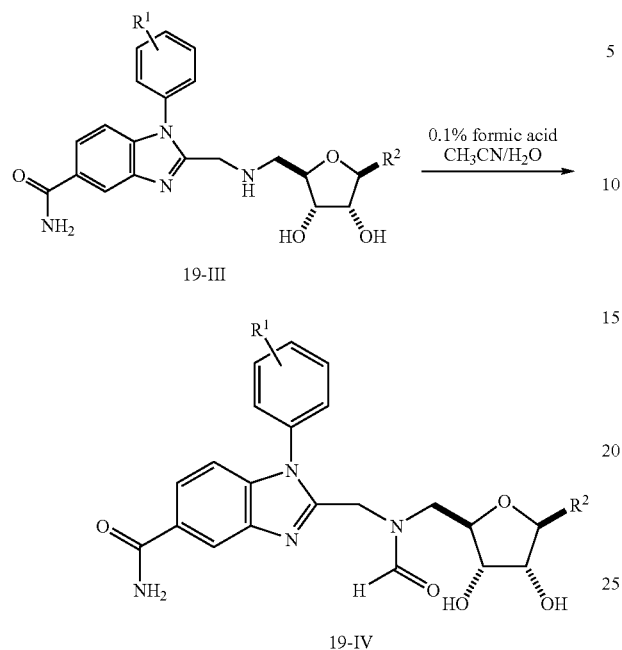
19-III
19-IV
| Compound | Retention time, observed mass, yield 2 components 19-III and 19-IV |
|---|---|
| 345 | Rt = 6.41 min (M + H)⁺ = 611 (58%), Rt = 7.26 min (M + H)⁺ = 639 (42%) |
EXAMPLE 20
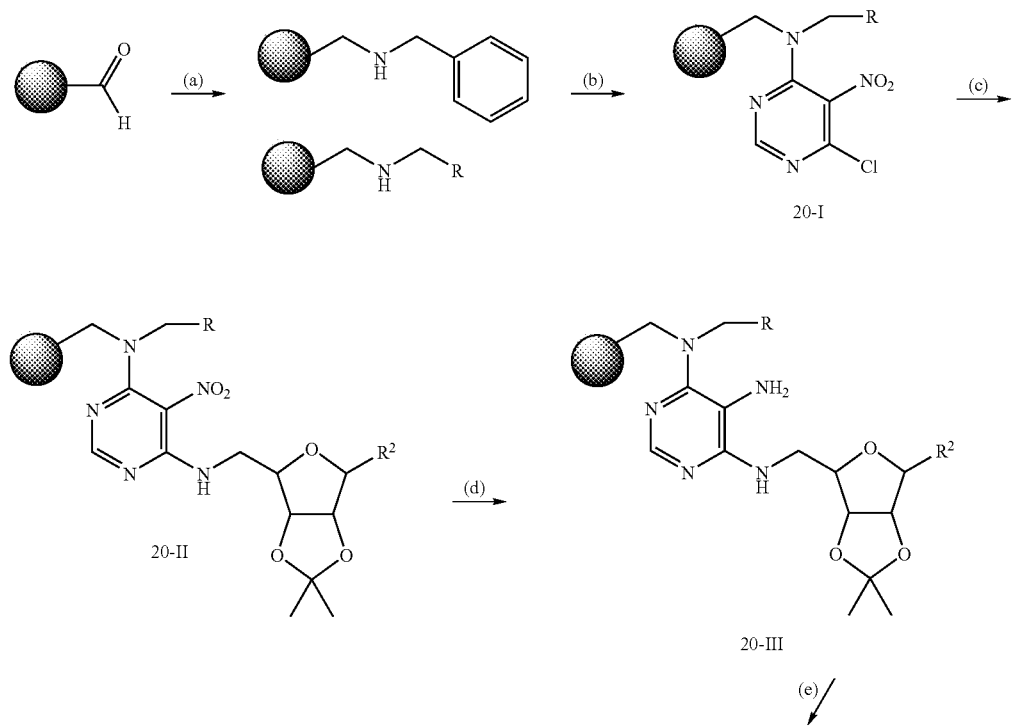

-continued

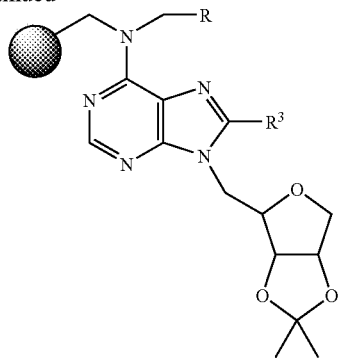

20-IV

↓ (f)

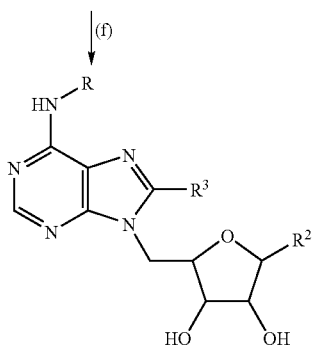

20-V (20-a) General Method 12, (20-b) General Method 19, (20-c) General Method 6, (20-d) General Method 20, (20-e) General Method 21, (20-f) General Method 9 for adenosine containing compounds only, then General Method 3b for all compounds.

Analysis of Some Typical Example Compounds

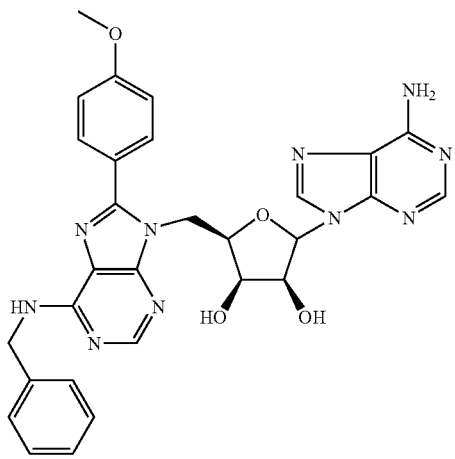

718

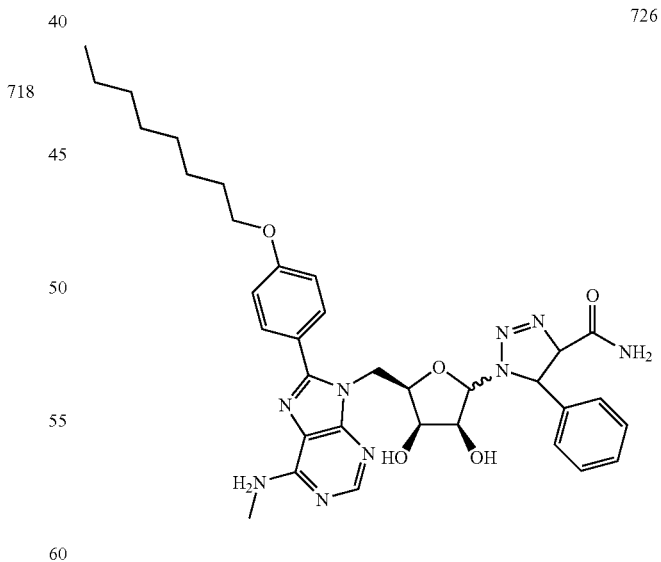

726 proton NMR (400 MHz, $d_6$-DMSO): δ: 8.37 (s, 1H); 8.24 (s, 1H); 7.57 (d, 2H, J=8.8 Hz); 7.35 (d, 2H, J=7.2 Hz); 7.30 (t, 2H, J=7.6 Hz); 7.21 (t, 2H, J=7.2 Hz), 6.77 (d, 2H, J=8.8 Hz), 5.81 (d, 1H, J=4.4 Hz); 4.71-4.63 (m, 3H), 4.64 (t, 1H, J=4.8 Hz); 4.46-4.38 (m, 2H); 4.33-4.30 (m, 1H), 3.76 (s, 3H).

Beta Isomer:
proton NMR (400 MHz, $d_6$-DMSO): δ: 8.27 (s, 1H), 7.88 (s, 1H), 7.55-7.41 (m, 6H); 7.28 (dd, 2H, J=1.2, 7.6 Hz); 6.84 (d, 2H, J=8.8 Hz); 5.31 (d, 1H, J=2 Hz); 4.66 (d, 1H, J=11.2 Hz); 4.51 (s, 1H); 4.41-4.32 (m, 3H); 3.97-3.88 (m, 3H); 2.98 (s, 3H); 1.73-1.66 (m, 2H); 1.39-1.26 (m, 12H); 0.87-0.84 (m, 3H).

Alpha Isomer:
(proton NMR (400 MHz, d$_6$-DMSO): δ: 8.25 (s, 1H), 7.82 (d, 3H, J=8.4 Hz); 7.51-7.46 (m, 6H); 7.11 (d, 2H, J=8.8 Hz); 5.43 (d, 1H, J=4.4 Hz); 4.91 (s, 1H); 4.37 (s, 1H); 4.23 (q, 1H, J=5.6, 8.8 Hz); 4.06 (t, 2H, J=6.4 Hz); 3.79 (s, 3H); 1.77-1.70 (m, 2H); 1.44-1.26 (m, 12H); 0.87-0.84 (m, 3H).
EXAMPLE 21
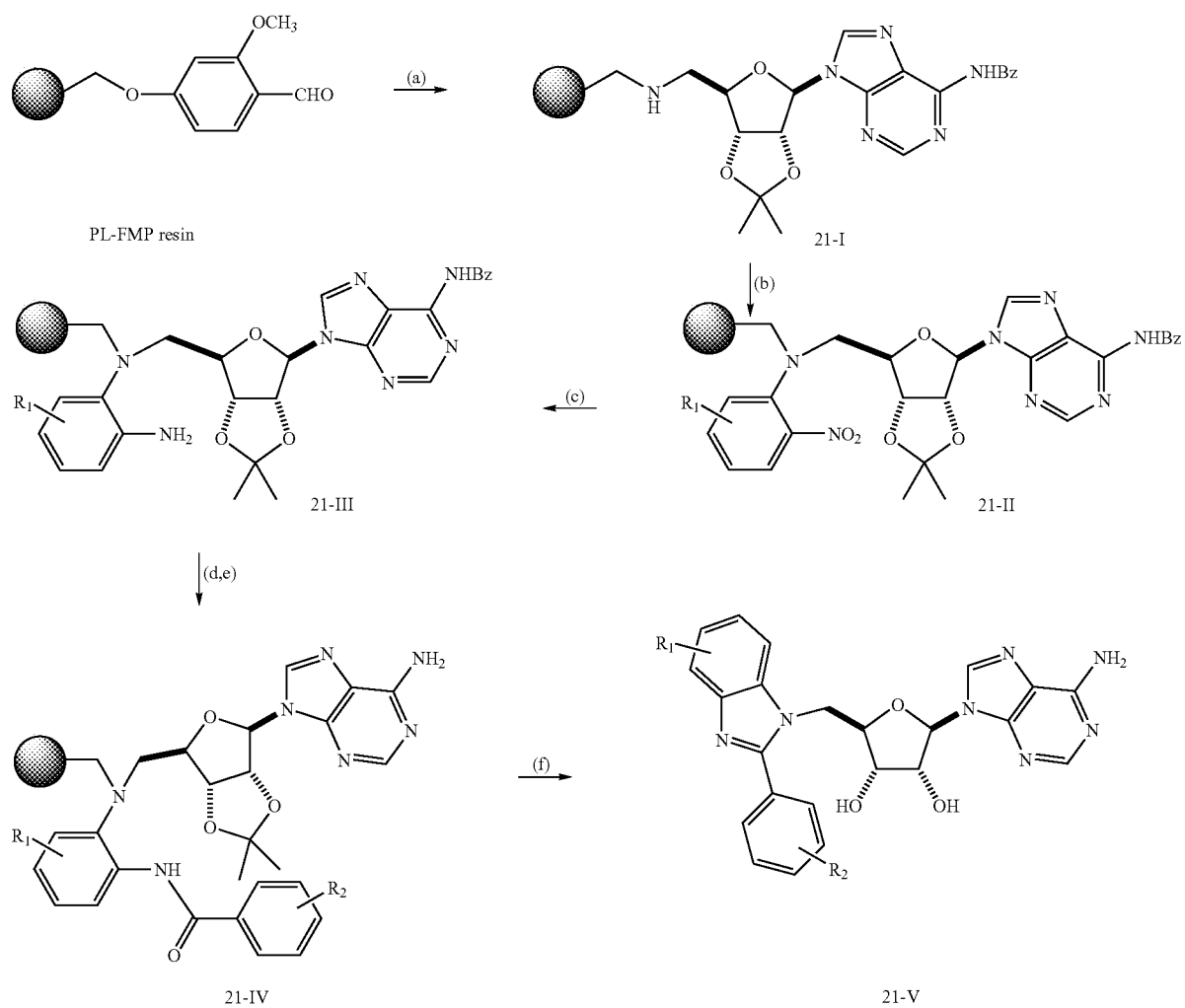
(21-a) General Method 12, (21-b) General Method 6, (21-c) General Method 7, (21-d) General Method 1 or 22, (21-e) General Method 9, (21-f) General Method 3-b then General Method Method 3a.
Analysis of Some Typical Example Compounds
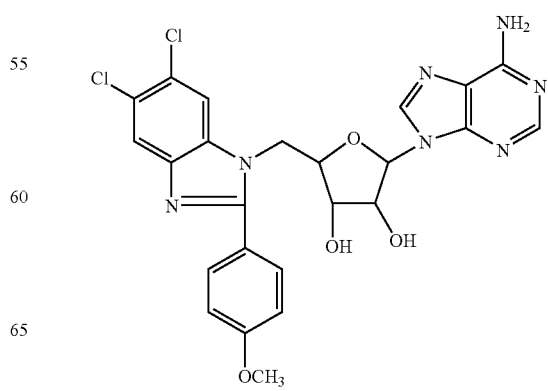
920 proton (400 MHz, d⁶-DMSO): 8.36 (s, 1H, H-8), 8.25 (s, 1H, H-2), 7.88 (s, 2H, ArCH), 7.62 (d, 2H, J=8.8 Hz, ArCH), 6.84 (d, 2H, J=8.8 Hz, ArCH), 5.85 (d, 1H, J=3.6 Hz, H'-1), 4.73 (dd, 1H, J=3.5, 15.8 Hz, CH), 4.57-4.64 (m, 2H, CH$_2$), 4.36 (t, 1H, J=5.6 Hz, CH), 4.22 (m, 1H, H'-4), 3.80 (s, 3H, OCH$_3$).
EXAMPLE 22
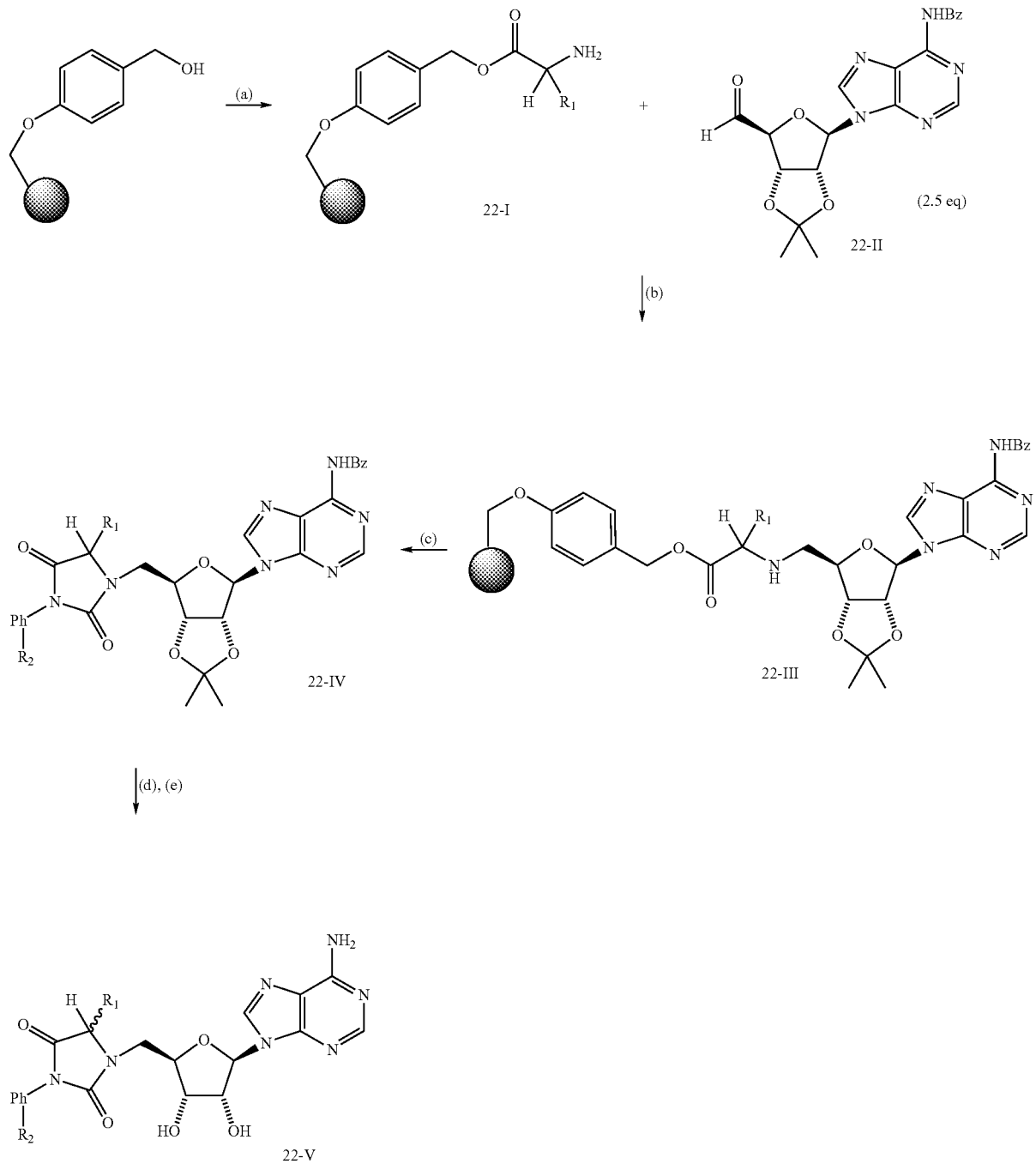
(22-a) General Method 1, general method 4 (22-b) General Method 12, (22-c) General Method 23, (22-d) General Method 9, (22-e) General Method 3-a.

Analysis of Some Typical Example Compounds

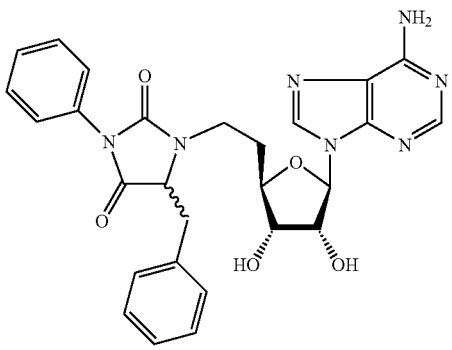
741

Isomer 1:
proton NMR (400 MHz, d$_6$-DMSO): δ: 8.48 (s, 1H); 8.17 (s, 1H); 7.39-7.22 (m, 6H); 7.11 (d, 2H, J=7.6 Hz); 6.86 (d, 2H, J=6.8 Hz); 5.93 (d, 1H, J=4.8 Hz); 4.67 (t, 1H, J=4.8 Hz); 4.59 (t, 1H, J=3.6 Hz); 4.34 (t, 1H, J=5.2 Hz); 4.22 (q, 1H, J=4.8, 10 Hz); 4.00 (dd, 1H, =6.8, 15.2 Hz); 3.76 (dd, 1H, J=7.6, 14.8 Hz); 3.26 (dd, 1H, J=4.4, 14 Hz); 3.05 (dd, 1H, J=3.6, 14.4 Hz).

Isomer 2:
proton NMR (400 MHz, d$_6$-DMSO): δ: 8.59 (s, 1H); 8.31 (s, 1H); 7.38-7.23 (m, 5H); 7.11-7.06 (m, 3H); 6.88 (d, 2H, J=6.8 Hz); 5.97 (d, 1H, J=6 Hz); 4.84 (t, 1H, J=4.8 Hz); 4.50 (t, 1H, J=3.6 Hz); 4.25-4.22 (m, 2H); 4.14 (dd, 1H, J=3.6, 14.8 Hz); 3.23 (dd, 1H, J=5.2, 14.4 Hz); 3.00 (dd, 1H, J=2.8, 14 Hz).

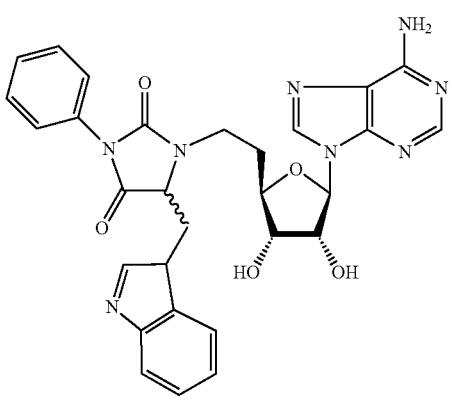
935

Isomer 1:
proton NMR (400 MHz, d$_6$-DMSO): δ: 10.94 (s, 1H); 8.59 (s, 1H); 8.26 (s, 1H); 7.48 (d, 1H, J=8 Hz); 7.32-7.26 (m, 4H); 7.10 (s, 1H); 7.06 (t, 1H, J=7.6 Hz); 6.93 (t, 1H, J=7.6 Hz); 6.69-6.67 (m, 2H); 5.95 (d, 1H, J=5.2 Hz); 4.66 (t, 1H, J=5.6 Hz); 4.54 (t, 1H, J=3.2 Hz); 4.33 (t, 1H, J=4.8 Hz); 4.25 (q, 1H, J=5.2, 10.8 Hz); 4.00 (dd, 1H, J=6.4, 15.2 Hz); 3.76 (dd, 1H, J=4, 14.8 Hz); 3.37-3.25 (m, 2H).

Isomer 2:
proton NMR (400 MHz, d$_6$-DMSO): δ: 10.95 (s, 1H); 8.68 (s, 1H); 7.43 (d, 1H, J=8 Hz); 7.32 (d, 2H, J=8 Hz); 7.27-7.25 (m, 2H); 7.09 (s, 1H); 7.06 (t, 1H, J=8 Hz); 6.92 (t, 1H, J=8 Hz); 6.70 (dd, 2H, J=3.6, 7.6 Hz); 5.99 (d, 1H, J=5.6 Hz); 4.81 (t, 1H, J=5.2 Hz); 4.47 (t, 1H, J=3.2 Hz); 4.29-4.22 (m, 2H); 4.12 (dd, 1H, J=4.4, 14.8 Hz); 3.68 (dd, 1H, J=8.4, 14.8 Hz); 3.36 (dd, 1H, J=5.2, 15.2 Hz); 3.24 (dd, 1H, J=2.4, 15.2 Hz).

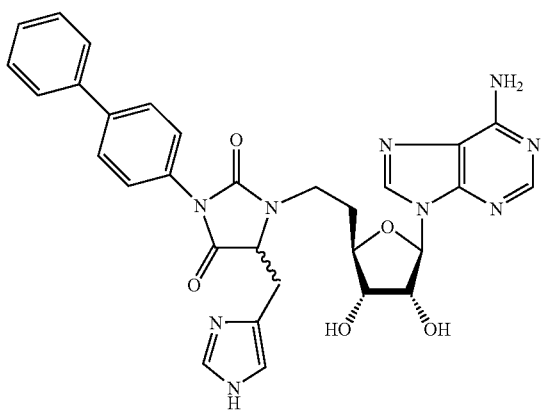
948

Isomer 1:
proton NMR (400 MHz, d$_6$-DMSO): δ: 8.96 (s, 1H); 8.49 (s, 1H); 8.03 (s, 1H); 7.73 (d, 2H, J=10.8 Hz); 7.61 (d, 2H, J=7.2 Hz); 7.49 (t, 2H, J=7.6 Hz); 7.40-7.35 (m, 2H); 7.34 (d, 2H, J=8.4 Hz); 5.95 (d, 1H, J=5.6 Hz); 4.70 (t, 1H, J=5.2 Hz); 4.65 (t, 1H, J=4.4 Hz); 4.31 (t, 1H, J=4.8 Hz); 4.27-4.23 (m, 1H); 3.95 (dd, 1H, J=7.6, 15.2 Hz); 3.77 (dd, 1H, J=4, 14.8 Hz); 3.26-3.24 (m, 2H).

Isomer 2:
proton NMR (400 MHz, d$_6$-DMSO): δ: 8.97 (s, 1H); 8.51 (s, 1H); 7.82 (s, 1H); 7.73 (d, 2H, J=8.8 Hz); 7.67 (d, 2H, J=7.2 Hz); 7.49 (t, 2H, J=7.2 Hz); 7.40-7.35 (m, 2H); 7.25 (d, 2H, J=8.4 Hz); 5.95 (d, 1H, J=5.6 Hz); 4.79 (t, 1H, J=4.8 Hz); 4.62 (t, 1H, J=5.6 Hz); 4.27-4.22 (m, 2H); 4.16 (dd, 1H, J=4, 14.8 Hz); 3.33-3.21 (m, 2H).

EXAMPLE 23

Part A

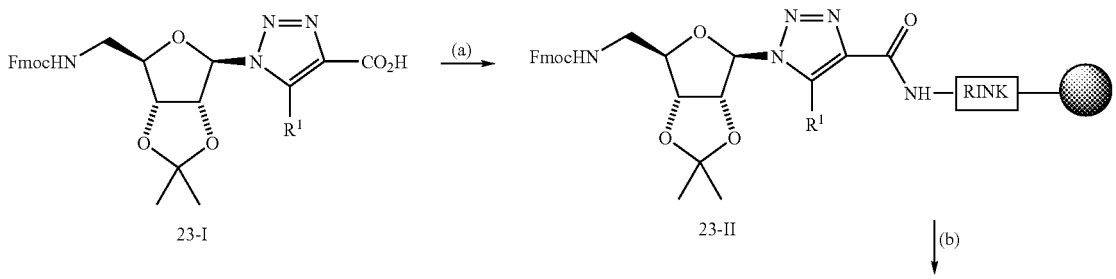

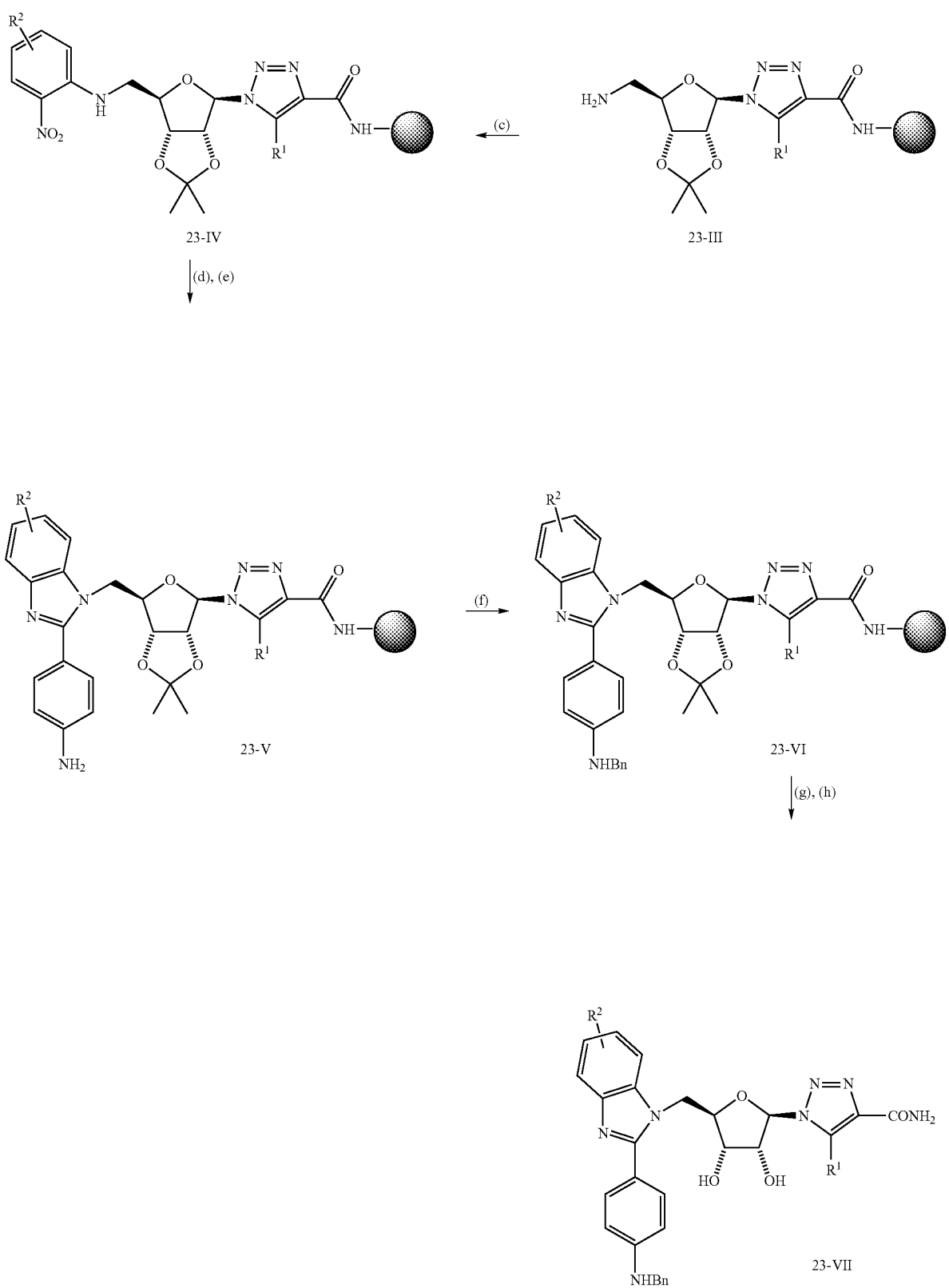
-continued
(23-a) General Method 1, (23-B) General Method 4, (23-c) General Method 6, (23-d) General Method 10, (23-e) Genreal Method 4 or General Method 20, (23-F) General Method 12. (23-g) General Method 9. (23-h) Gerneral Method 3a.

Part B
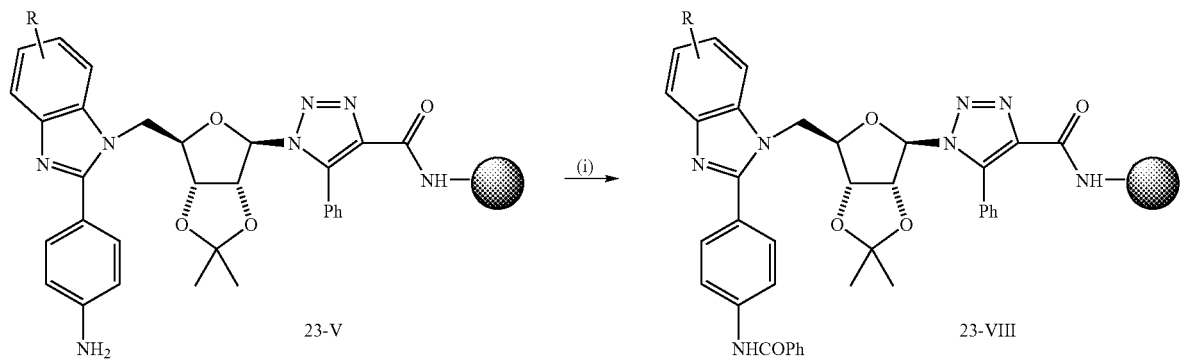
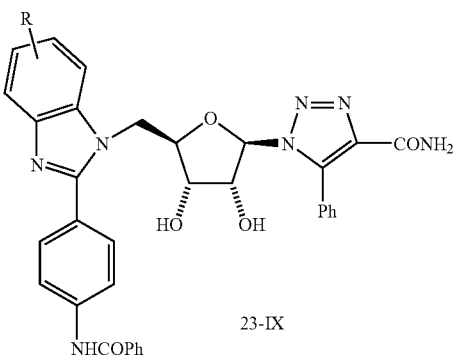
(23-i) General Method 22, (23-j) General Method 3-a
Part-C
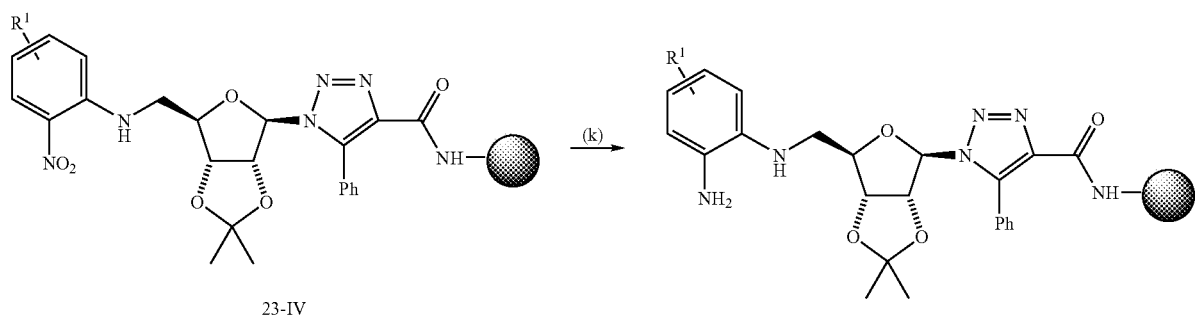

-continued

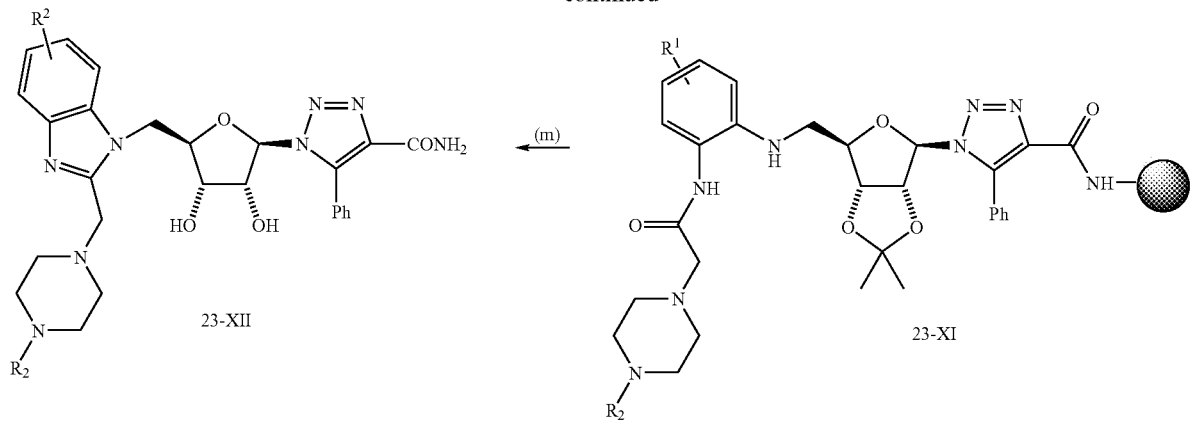

(23-k) General Method 7, (23-l) General Method 17, followed by treatment of the resins with a 1.43 Molar solution (~ 10 equivalents) of piperazine in dry DMF at room temperature overnight. The resin was then drained, washed ( 2 × DMF and 3 × DCM) and then dried in vacuo, General Method 12; (23-m)

General Method 3-a.

Analysis of a Typical Example Compounds

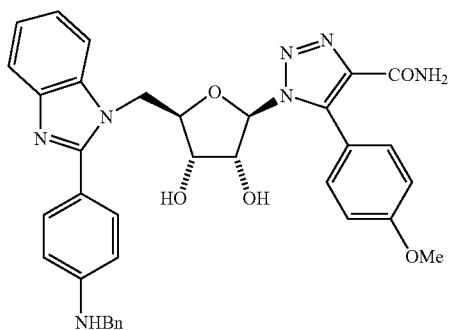

proton (400 MHz: $d_6$ DMSO) 3.79 (s, 3H, OCH$_3$), 4.30 (bs, 2H, H2, H3), 4.43 (bd, J 6.0 Hz, 3H, H4, NCH$_2$Ph), 4.65 (dd, J 15.6, 6.2 Hz, 1H, H5a), 4.91 (d, J 14.8 Hz, 1H, H5b), 5.35 (s, 1H, H1), 6.64 (d, J 8.8 Hz, 2H, ArH), 6.98 (d, J 8.8 Hz, 2H, ArH), 7.19 (d, J 8.8 Hz, 2H, ArH), 7.22-7.36 (m, 5H, ArH, NHa), 7.42-7.56 (m, 5H, ArH), 7.71 (t, J 7.6 Hz, 2H, ArH), 7.82 (bs, 1H, NHb).

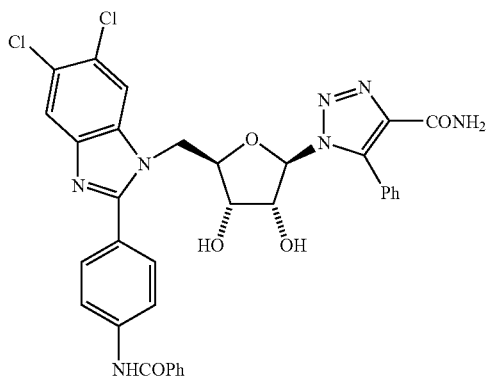

968 proton (400 MHz: $d_6$ DMSO) 4.24-4.31 (m, 1H, H4), 4.38 (dd, J 7.4, 5.0 Hz, 1H, H3), 4.47 (dd, J 4.4, 1.6 Hz, 1H, H2), 4.50 (dd, J 15.6, 7.6 Hz, 1H, H5a), 4.76 (dd, J 15.6, 2.8 Hz, 1H, H5b), 5.33 (d, J 1.2 Hz, 1H, H1), 7.29 (dd, J 7.8, 1.4 Hz, 2H, ArH), 7.40-7.62 (m, 8H, ArH, ArCONHa), 7.68 (d, J 8.4 Hz, 2H, ArH), 7.83 (s, 1H, ArCONHb), 7.88 (d, J 8.8 Hz, 2H, ArH), 7.91-7.99 (m, 3H, ArH), 10.46 (s, 1H, ArNH-COPh).

EXAMPLE 24

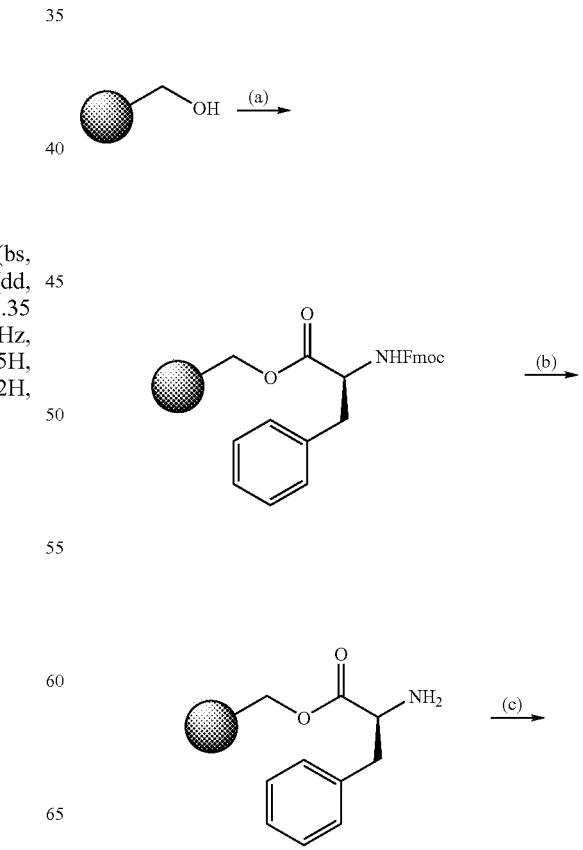

-continued

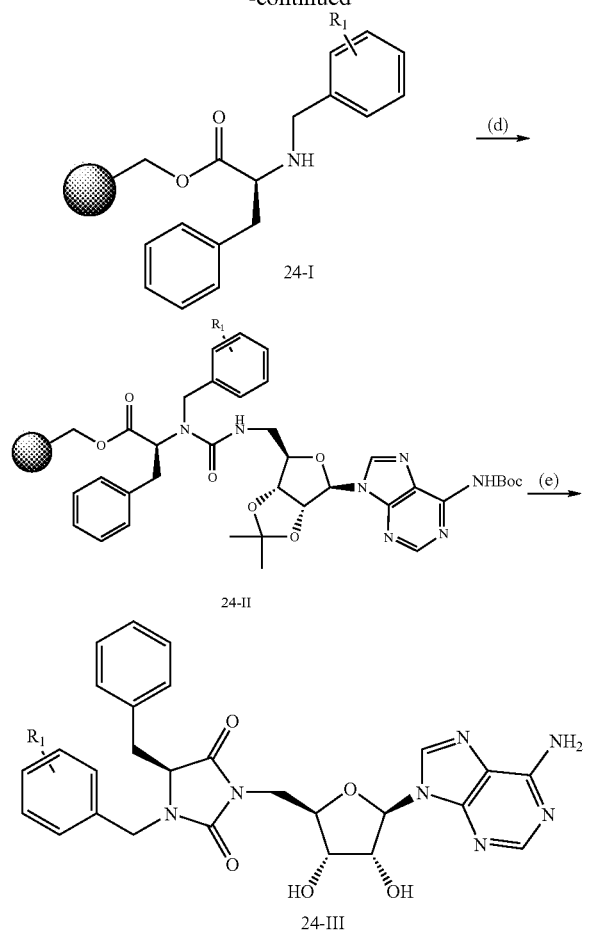

24-I

24-II

24-III (24-a) General Method 1, (24-b) General Method 4, (24-c) General Method 12, (24-d) General Method 13, (24-e) General Method 3-b.

Analysis of Some Typical Example Compounds

954

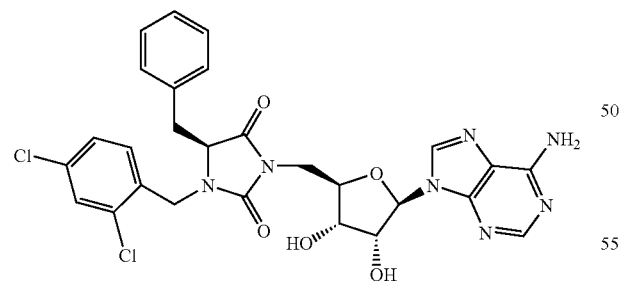

proton (d$^6$-DMSO, 400 MHz): 8.51 (s, 1H, H-2/8), 8.31 (s, 1H, H-2/8), 7.60-7.05 (m, 8H, ArCH), 5.86 (d, 1H, J=5.6, Hz, H'-1), 4.67 (t, 1H, J=5.5 Hz, H'-2/3), 4.64 (d, 1H, J$_{AB}$=16.1 Hz, HA-), 4.39 (d, 1H, J$_{AB}$=16.1 Hz, HB-), 4.34 (t, 1H, J=5.1 Hz, H-2/3), 4.09 (t, 1H, J=4.2 Hz), 3.99 (m, 1H, H'-4), 3.67 (dd, 1H, J=5.8 Hz, 14.0 Hz, HA), 3.58 (dd, 1H, J=7.6, 14.0 Hz, HB), 3.14 (dd, 1H, J=5.1, 14.4 Hz, H'-5A), 3.02 (dd, 1H, J=4.6, 14.4 Hz, H'-5B).

960

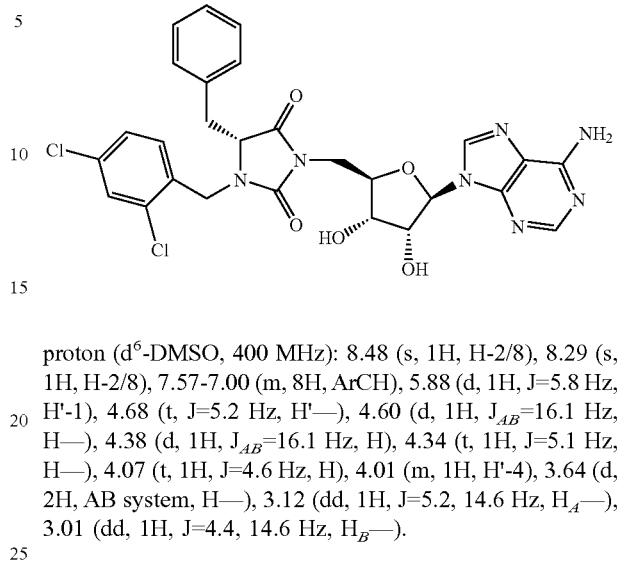

proton (d$^6$-DMSO, 400 MHz): 8.48 (s, 1H, H-2/8), 8.29 (s, 1H, H-2/8), 7.57-7.00 (m, 8H, ArCH), 5.88 (d, 1H, J=5.8 Hz, H'-1), 4.68 (t, J=5.2 Hz, H'—), 4.60 (d, 1H, J$_{AB}$=16.1 Hz, H—), 4.38 (d, 1H, J$_{AB}$=16.1 Hz, H), 4.34 (t, 1H, J=5.1 Hz, H—), 4.07 (t, 1H, J=4.6 Hz, H), 4.01 (m, 1H, H'-4), 3.64 (d, 2H, AB system, H—), 3.12 (dd, 1H, J=5.2, 14.6 Hz, H$_A$—), 3.01 (dd, 1H, J=4.4, 14.6 Hz, H$_B$—).

Exemplary Compounds of the Invention

The substructures A-H listed below are substituents in the field R1 in the libraries of compounds that follow.

A

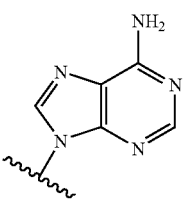

B

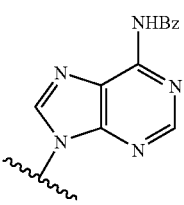

C

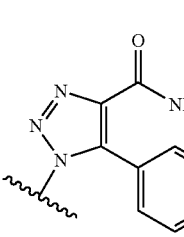

D

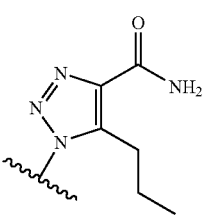

-continued

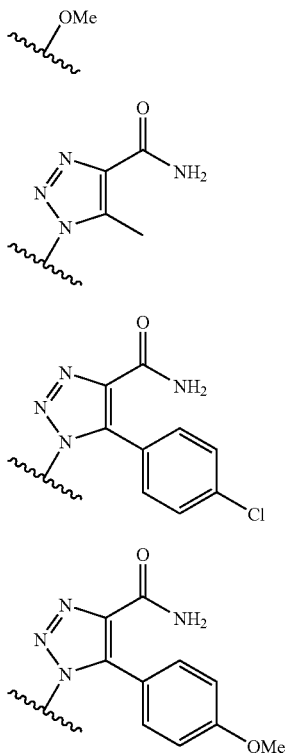

Others substituents referred to in the following libraries may be subsequently found in the text at the end of examples.

EXAMPLE 25

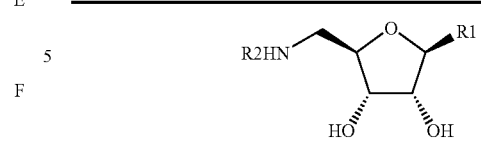

| Comp. | R1 | R2 | ISOMER | R (on arm) |
|---|---|---|---|---|
| 1 | A | IIa-1 | L and D | H |
| 2 | A | IIb-1 | L and D | H |
| 3 | A | IIc-1 | L and D | H |
| 4 | A | IId-1 | L and D | H |
| 5 | A | IIe-1 | L | H |
| 6 | A | IIe-1 | D | H |
| 7 | A | IIf-1 | L and D | H |
| 8 | A | IIg-1 | L and D | H |
| 9 | A | IIh-1 | L and D | H |
| 10 | A | IIi-1 | L and D | H |
| 11 | A | IIj-1 | L and D | H |
| 12 | A | IIk-1 | L and D | H |
| 13 | A | IIl-1 | L and D | H |
| 14 | A | IIo-1 | L | H |
| 15 | A | IIo-1 | D | H |
| 16 | B | IIa-1 | L and D | methyl |
| 17 | B | IIb-1 | L and D | methyl |
| 18 | B | IIc-1 | L and D | methyl |
| 19 | B | IId-1 | L and D | methyl |
| 20 | B | IIe-1 | L and D | H |
| 21 | B | IIf-1 | L and D | H |
| 22 | B | IIh-1 | L and D | methyl |
| 23 | B | IIi-1 | L and D | ethyl |
| 24 | B | IIj-1 | L and D | ethyl |
| 25 | B | IIk-1 | L and D | methyl |
| 26 | B | IIr-1 | L and D | methyl |
| 27 | B | IIl-1 | L and D | methyl |
| 28 | B | IIo-1 | L and D | methyl |
| 29 | B | IIp-1 | L and D | methyl |
| 30 | B | IIq-1 | L and D | methyl |

EXAMPLE 26

| Comp. | R1 | R2 | Isomer | R (on arm) |
|---|---|---|---|---|
| 31 | C | IIa-1 | L and D | H |
| 32 | C | IIb-1 | L and D | H |
| 33 | D | IIb-1 | L and D | H |
| 34 | C | IIc-1 | L and D | H |
| 35 | C | IId-1 | L and D | H |
| 36 | D | IId-1 | L and D | H |
| 37 | D | IIe-1 | L and D | H |
| 38 | C | IIe-1 | L and D | H |
| 39 | D | IIf-1 | L and D | H |
| 40 | C | IIf-1 | L and D | H |
| 41 | D | IIg-1 | L and D | H |
| 42 | C | IIh-1 | L and D | H |
| 43 | D | IIh-1 | L and D | H |
| 44 | C | IIi-1 | L | H |
| 45 | D | IIi-1 | L | H |
| 46 | C | IIj-1 | L | H |
| 47 | D | IIj-1 | L | H |
| 48 | C | IIk-1 | L and D | H |
| 49 | D | IIk-1 | L and D | H |
| 50 | C | IIr-1 | L | H |
| 51 | D | IIr-1 | L | H |
| 52 | C | IIl-1 | L | H |
| 53 | D | IIl-1 | L | H |
| 54 | C | IIn-1 | L | H |
| 55 | D | IIn-1 | L | H |
| 56 | C | IIo-1 | L | H |
| 57 | D | IIo-1 | L | H |
| 58 | C | IIp-1 | L | H |
| 59 | D | IIp-1 | L | H |
| 60 | C | IIq-1 | L | H |
| 61 | D | IIq-1 | L | H |
| 62 | C | IIb-1 | L | H |
| 63 | D | IIb-1 | L | H |
| 64 | C | IIe-1 | L | H |
| 65 | D | IIe-1 | L | H |

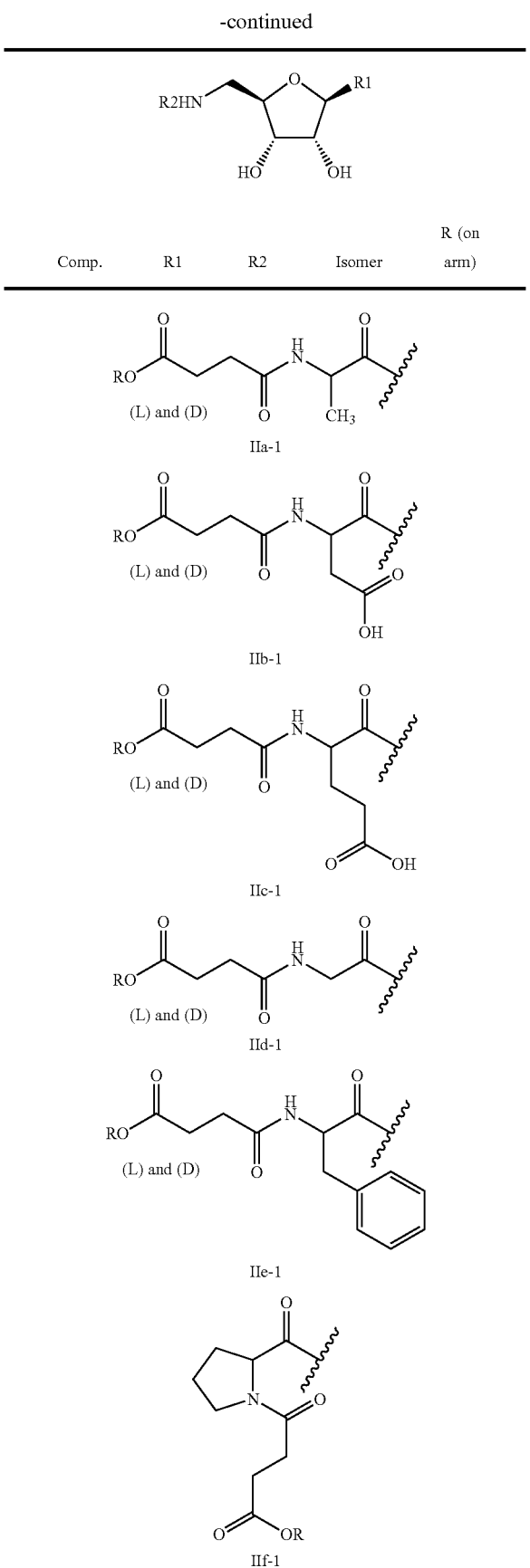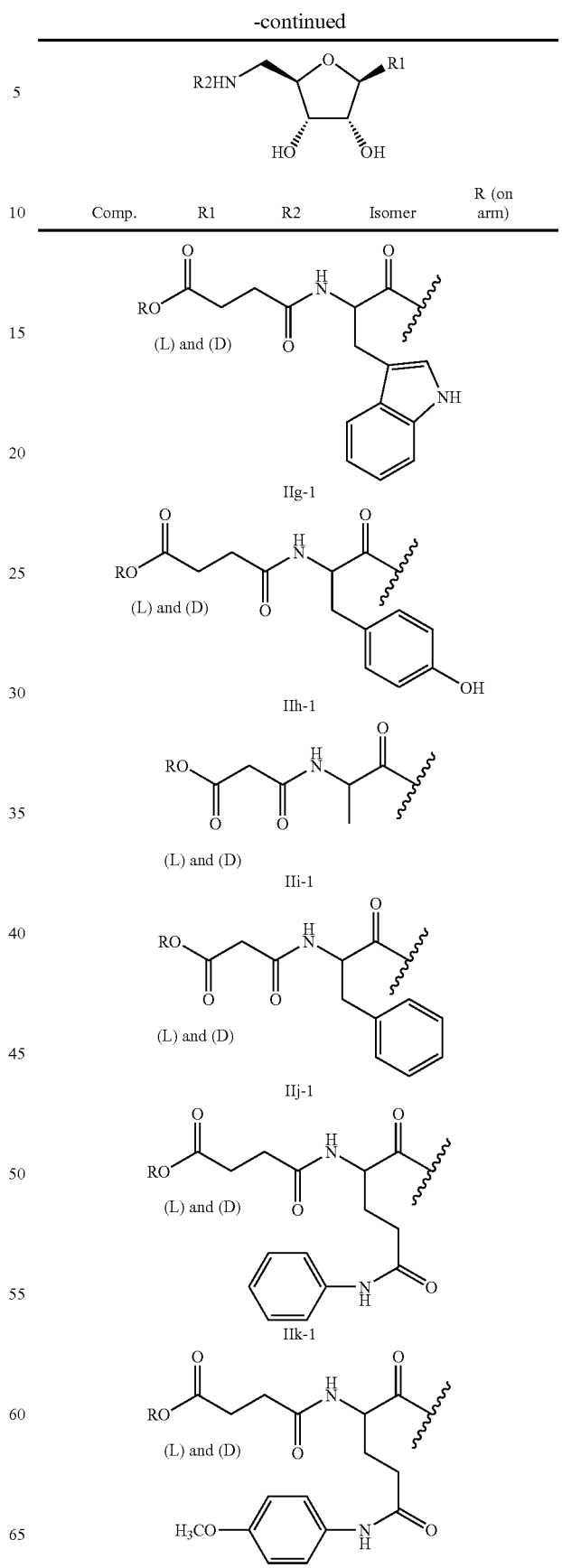

-continued

R2HN—[furanose ring]—R1, with HO, OH
III-1

| Comp. | R1 | R2 | Isomer | R (on arm) |
|---|---|---|---|---|

IIm-1: RO-C(O)-CH2CH2-C(O)-NH-CH(~)-C(O)-, side chain -CH2CH2-C(O)-NH-C6H4-4-CF3, (L) and (D)

IIn-1: RO-C(O)-CH2CH2-C(O)-NH-CH(~)-C(O)-, side chain -CH2-C(O)-NH-C6H4-3-Cl, (L) and (D)

IIo-1: RO-C(O)-CH2CH2-C(O)-NH-CH(~)-C(O)-, side chain -CH2-C(O)-NH-C6H5, (L) and (D)

IIp-1: RO-C(O)-CH2CH2-C(O)-NH-CH(~)-C(O)-, side chain -CH2-C(O)-NH-C6H4-3-CF3, (L) and (D)

IIq-1: RO-C(O)-CH2CH2-C(O)-NH-CH(~)-C(O)-, side chain -CH2-C(O)-NH-C6H4-4-CH3, (L) and (D)

-continued

R2HN—[furanose ring]—R1, with HO, OH

| Comp. | R1 | R2 | Isomer | R (on arm) |
|---|---|---|---|---|

IIr-1: RO-C(O)-CH2CH2-C(O)-NH-CH(~)-C(O)-, side chain -CH2CH2-C(O)-NH-C6H4-3-CF3, (L) and (D)

EXAMPLE 27

R3-NH-C(O)-CH(R2)-N(C(O)R4)-CH2-[furanose]-R1, HO, OH

| Comp. | R1 | R2 | R3 | R4 |
|---|---|---|---|---|
| 66 | A | α4 | ν2 | Σ1 |
| 67 | A | β7 | ν2 | Σ1 |
| 68 | A | β6 | ν2 | Σ1 |
| 69 | A | χ5 | ν2 | Σ1 |
| 70 | A | κ4 | ν2 | Σ1 |
| 71 | A | α4 | ν2 | α4 |
| 72 | A | β7 | ν2 | α4 |
| 73 | A | β6 | ν2 | α4 |
| 74 | A | χ5 | ν2 | α4 |
| 75 | A | κ4 | ν2 | α4 |
| 76 | A | α4 | α1 | Σ1 |
| 77 | A | β7 | α1 | Σ1 |
| 78 | A | β6 | α1 | Σ1 |
| 79 | A | χ5 | α1 | Σ1 |
| 80 | A | κ4 | α1 | Σ1 |
| 81 | A | α4 | α1 | α1 |
| 82 | A | β7 | α1 | α1 |
| 83 | A | β6 | α1 | α1 |
| 84 | A | χ5 | α1 | α1 |
| 85 | A | κ4 | α1 | α1 |

EXAMPLE 28
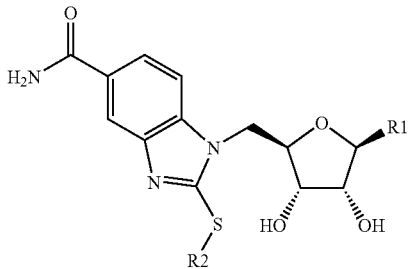
| Comp. | R1 | R2 |
|---|---|---|
| 86 | A | β1 |
| 87 | A | γ1 |
| 88 | A | β2 |
| 89 | A | δ2 |
| 90 | A | ε1 |
| 91 | A | κ1 |
| 92 | A | π1 |
| 93 | A | ω1 |
| 94 | A | ε2 |
| 95 | A | σ1 |
| 96 | A | β3 |
| 97 | A | γ2 |
| 98 | A | γ3 |
| 99 | A | δ2 |
| 100 | A | ε3 |
| 101 | A | κ2 |
| 102 | A | π2 |
| 103 | A | ε4 |
| 104 | A | β4 |
| 105 | A | γ4 |
| 106 | A | β5 |
| 107 | A | φ1 |
| 108 | A | π3 |
| 109 | A | φ2 |
| 110 | A | ν1 |
| 111 | A | ν2 |
| 112 | A | ν3 |
| 113 | A | ν4 |
| 114 | A | λ1 |
| 115 | A | ν5 |
| 116 | A | ν6 |
| 117 | A | ε5 |
| 118 | A | ε6 |
| 119 | A | ν7 |
| 120 | A | χ1 |
EXAMPLE 29
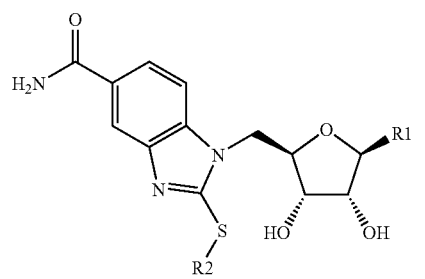
| Comp. | R1 | R2 |
|---|---|---|
| 121 | C | α1 |
| 122 | C | β1 |
| 123 | C | γ1 |
| 124 | C | β2 |
| 125 | C | δ1 |
| 126 | C | ε1 |
| 127 | C | κ1 |
| 128 | C | π1 |
| 129 | C | ω1 |
| 130 | C | ε2 |
| 131 | C | σ1 |
| 132 | C | β3 |
| 133 | C | γ2 |
| 134 | C | γ3 |
| 135 | C | δ2 |
| 137 | C | ε3 |
| 137 | C | κ2 |
| 138 | C | π2 |
| 139 | C | ε4 |
| 140 | C | β4 |
| 141 | C | γ4 |
| 142 | C | β5 |
| 143 | C | φ1 |
| 144 | C | π3 |
| 145 | C | φ2 |
| 146 | C | ν1 |
| 147 | C | ν2 |
| 148 | C | ν3 |
| 149 | C | ν4 |
| 150 | C | λ1 |
| 151 | C | ν5 |
| 152 | C | ν6 |
| 153 | C | ρ1 |
| 154 | C | ε5 |
| 155 | C | ε6 |
| 156 | C | ρ2 |
| 157 | C | ν7 |
| 158 | C | χ1 |
| 159 | D | α1 |
| 160 | D | β1 |
| 161 | D | γ1 |
| 162 | D | β2 |
| 163 | D | δ1 |
| 164 | D | ε1 |
| 165 | D | κ1 |
| 166 | D | π1 |
| 167 | D | ω1 |
| 168 | D | ε2 |
| 169 | D | σ1 |
| 170 | D | β3 |
| 171 | D | γ2 |
| 172 | D | γ3 |
| 173 | D | δ2 |
| 174 | D | ε3 |
| 175 | D | κ2 |
| 176 | D | π2 |
| 177 | D | ε4 |
| 178 | D | β4 |
| 179 | D | γ4 |
| 180 | D | β5 |
| 181 | D | φ1 |
| 182 | D | π3 |
| 183 | D | φ2 |
| 184 | D | ν1 |

-continued
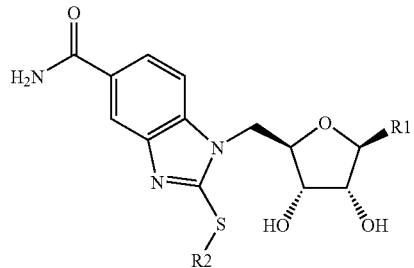
| Comp. | R1 | R2 |
|---|---|---|
| 185 | D | ν2 |
| 186 | D | ν3 |
| 187 | D | ν4 |
| 188 | D | λ1 |
| 189 | D | ν5 |
| 190 | D | ν6 |
| 191 | D | ρ1 |
| 192 | D | ε5 |
| 193 | D | ε6 |
| 194 | D | ρ2 |
| 195 | D | ν7 |
| 196 | D | χ1 |
EXAMPLE 30
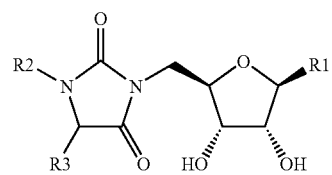
| Comp. | R1 | R2 | R3 |
|---|---|---|---|
| 197 | A | π4 | ψ1 |
| 198 | A | β1 | ψ1 |
| 199 | A | ξ1 | ψ1 |
| 200 | A | ε5 | ψ1 |
| 201 | A | ε2 | ψ1 |
| 202 | A | σ1 | ψ1 |
| 203 | A | α2 | ψ1 |
| 204 | A | μ1 | ψ1 |
| 205 | A | τ1 | ψ1 |
| 206 | A | τ2 | ψ1 |
| 207 | A | μ2 | ψ1 |
| 208 | A | ε7 | ψ1 |
| 209 | A | μ3 | ψ1 |
| 210 | A | γ2 | ψ1 |
| 211 | A | γ5 | ψ1 |
| 212 | A | π4 | α1 |
| 213 | A | β1 | α1 |
| 214 | A | ξ1 | α1 |
| 215 | A | ε5 | α1 |
| 216 | A | ε2 | α1 |
| 217 | A | σ1 | α1 |
| 218 | A | α2 | α1 |
| 219 | A | μ1 | α1 |
| 220 | A | τ1 | α1 |
| 221 | A | τ2 | α1 |
| 222 | A | ε7 | α1 |
| 223 | A | μ3 | α1 |
| 224 | A | γ2 | α1 |
| 225 | A | γ5 | α1 |
| 226 | C | π4 | ψ1 |
| 227 | C | β1 | ψ1 |
-continued
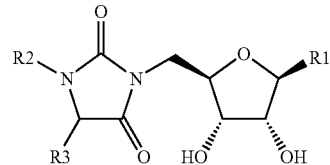
| Comp. | R1 | R2 | R3 |
|---|---|---|---|
| 228 | C | ξ1 | ψ1 |
| 229 | C | ε5 | ψ1 |
| 230 | C | μ1 | ψ1 |
| 231 | C | τ1 | ψ1 |
| 232 | C | τ2 | ψ1 |
| 233 | C | μ2 | ψ1 |
| 234 | C | ε7 | ψ1 |
| 235 | C | μ3 | ψ1 |
| 236 | C | γ2 | ψ1 |
| 237 | C | γ5 | ψ1 |
| 238 | C | ξ1 | α1 |
| 239 | C | ε5 | α1 |
| 240 | C | ε2 | α1 |
| 241 | C | σ1 | α1 |
| 242 | C | α2 | α1 |
| 243 | C | μ1 | α1 |
| 244 | C | τ1 | α1 |
| 245 | C | τ2 | α1 |
| 246 | C | μ2 | α1 |
| 247 | C | ε7 | α1 |
| 248 | C | μ3 | α1 |
| 249 | C | γ2 | α1 |
| 250 | C | γ5 | α1 |
| 251 | D | π4 | α1 |
| 252 | D | β1 | α1 |
| 253 | D | ε2 | ψ1 |
| 254 | D | σ1 | ψ1 |
EXAMPLE 31
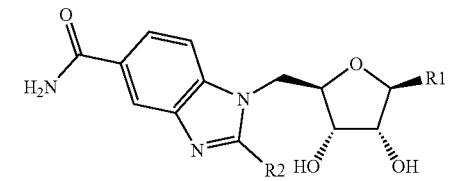
| Comp. | R1 | R2 |
|---|---|---|
| 255 | A | σ2 |
| 256 | A | ξ3 |
| 257 | A | β6 |
| 258 | A | θ1 |
| 259 | A | ε8 |
| 260 | A | χ2 |
| 261 | A | χ3 |
| 262 | A | χ4 |
| 263 | A | ν8 |
| 264 | A | β8 |
| 265 | A | π5 |
| 266 | A | μ4 |
| 267 | A | μ5 |
| 268 | A | τ3 |
| 269 | A | α3 |
| 270 | A | τ4 |
| 271 | A | σ3 |
| 272 | A | β9 |
| 273 | A | μ6 |
| 274 | C | ξ2 |

-continued
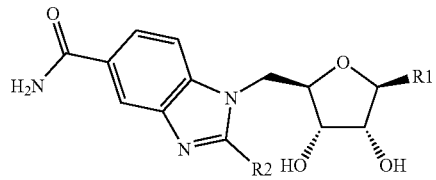
| Comp. | R1 | R2 |
|---|---|---|
| 275 | C | β6 |
| 276 | C | φ1 |
| 277 | C | θ1 |
| 278 | C | χ2 |
| 279 | C | χ3 |
| 280 | C | χ4 |
| 281 | C | ν8 |
| 282 | C | β8 |
| 283 | C | π5 |
| 284 | C | μ4 |
| 285 | C | μ5 |
| 286 | C | τ3 |
| 287 | C | σ3 |
| 288 | C | τ4 |
| 289 | C | σ3 |
| 290 | C | β9 |
| 291 | C | μ6 |
| 292 | D | σ2 |
| 293 | D | ξ2 |
| 294 | D | β6 |
| 295 | D | φ1 |
| 296 | D | θ1 |
| 297 | D | ε8 |
| 298 | D | χ2 |
| 299 | D | χ3 |
| 300 | D | χ4 |
| 301 | D | ν8 |
| 302 | D | β8 |
| 303 | D | π5 |
| 304 | D | μ4 |
| 305 | D | μ5 |
| 306 | D | τ3 |
| 307 | D | α3 |
| 308 | D | τ4 |
| 309 | D | σ3 |
| 310 | D | β9 |
| 311 | D | μ6 |
EXAMPLE 32
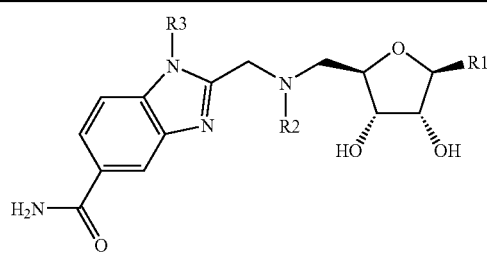
| Comp. | R1 | R2 | R3 |
|---|---|---|---|
| 312 | A | Σ2 | α4 |
| 313 | A | Σ2 | β6 |
| 314 | A | Σ2 | χ5 |
| 315 | A | Σ2 | ε9 |
| 316 | A | Σ2 | β7 |
| 317 | A | Σ2 | ε10 |
| 318 | A | ψ1 | θ2 |
-continued
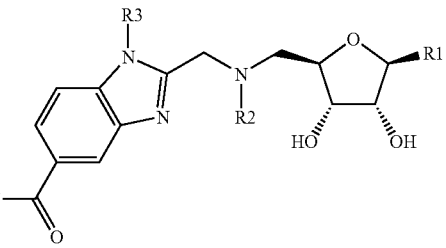
| Comp. | R1 | R2 | R3 |
|---|---|---|---|
| 319 | A | Σ2 | ε11 |
| 320 | A | Σ2 | χ6 |
| 321 | A | ψ1 | χ4 |
| 322 | A | Σ2 | σ3 |
| 323 | C | Σ2 | α4 |
| 324 | C | Σ2 | β6 |
| 325 | C | Σ2 | χ5 |
| 326 | C | Σ2 | ε9 |
| 327 | C | ψ1 | β7 |
| 328 | C | ψ1 | ε10 |
| 329 | C | Σ2 | θ2 |
| 330 | C | Σ2 | ξ3 |
| 331 | C | Σ2 | ε11 |
| 332 | C | Σ2 | χ6 |
| 333 | C | Σ2 | χ4 |
| 334 | C | ψ1 | σ3 |
| 335 | D | Σ2 | α4 |
| 336 | D | Σ2 | β6 |
| 337 | D | Σ2 | χ5 |
| 338 | D | Σ2 | ε9 |
| 339 | D | ψ1 | β7 |
| 340 | D | Σ2 | ε10 |
| 341 | D | Σ2 | θ2 |
| 342 | D | Σ2 | ε11 |
| 343 | D | Σ2 | χ6 |
| 344 | D | Σ2 | χ4 |
| 345 | D | ψ1 | σ3 |
EXAMPLE 33
| Comp. | R1 | R2 |
|---|---|---|
| 346 | A | χ5 |
| 347 | D | χ5 |
| 348 | A | ε9 |
| 349 | D | ε9 |
| 350 | A | χ6 |
| 351 | D | χ7 |
| 352 | A | α1 |
| 353 | C | α1 |
| 354 | D | α1 |
| 355 | A | θ3 |
| 356 | C | θ3 |
| 357 | D | θ3 |
| 358 | A | γ3 |
| 359 | C | γ3 |
| 360 | D | γ3 |
| 361 | A | θ4 |

-continued
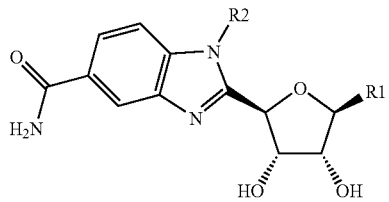
| Comp. | R1 | R2 |
|---|---|---|
| 362 | C | θ4 |
| 363 | D | θ4 |
| 364 | A | γ¹ |
| 365 | C | γ¹ |
| 366 | D | γ¹ |
| 367 | A | ε3 |
| 368 | C | ε3 |
| 369 | D | ε3 |
| 370 | A | χ¹ |
| 371 | C | χ¹ |
| 372 | D | χ¹ |
| 373 | A | ε5 |
| 374 | C | ε5 |
| 375 | D | ε5 |
| 376 | A | κ1 |
| 377 | C | κ1 |
| 378 | D | κ1 |
| 379 | A | θ1 |
| 380 | C | θ1 |
| 381 | D | θ1 |
| 382 | A | κ2 |
| 383 | C | κ2 |
| 384 | D | κ2 |
| 385 | A | α5 |
| 386 | C | α5 |
| 387 | D | α5 |
| 388 | A | β10 |
| 389 | C | β10 |
| 390 | D | β10 |
| 391 | A | γ6 |
| 392 | C | γ6 |
| 393 | D | γ6 |
| 394 | A | ν2 |
| 395 | C | ν2 |
| 396 | D | ν2 |
EXAMPLE 34
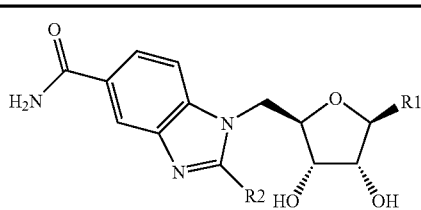
| Comp. | R1 | R2 |
|---|---|---|
| 397 | A | θ1 |
| 398 | C | θ1 |
| 399 | D | θ1 |
| 400 | A | α4 |
| 401 | A | ε11 |
| 402 | A | χ⁸ |
| 403 | A | ε9 |
| 404 | A | ξ3 |
| 405 | A | ω2 |
| 406 | A | α6 |
-continued
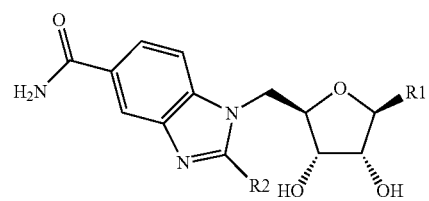
| Comp. | R1 | R2 |
|---|---|---|
| 407 | A | μ7 |
| 408 | A | φ3 |
| 409 | A | τ4 |
| 410 | A | α7 |
| 411 | A | μ8 |
| 412 | A | α1 |
| 413 | A | ε10 |
| 414 | A | κ3 |
| 415 | A | ε12 |
| 416 | A | γ⁷ |
| 417 | A | γ⁸ |
| 418 | A | γ⁹ |
| 419 | C | α4 |
| 420 | C | ε11 |
| 421 | C | χ⁸ |
| 422 | C | ε9 |
| 423 | C | ξ3 |
| 424 | C | ω2 |
| 425 | C | α6 |
| 426 | C | μ7 |
| 427 | C | φ3 |
| 428 | C | τ4 |
| 429 | C | α7 |
| 430 | C | μ6 |
| 431 | C | α1 |
| 432 | C | ε10 |
| 433 | C | κ3 |
| 434 | C | ε12 |
| 435 | C | γ⁷ |
| 436 | C | γ⁸ |
| 437 | C | γ⁹ |
| 438 | D | α4 |
| 439 | D | ε11 |
| 440 | D | χ⁸ |
| 441 | D | ε9 |
| 442 | D | ξ3 |
| 443 | D | ω2 |
| 444 | D | α6 |
| 445 | D | μ7 |
| 446 | D | φ3 |
| 447 | D | τ4 |
| 448 | D | α7 |
| 449 | D | μ8 |
| 450 | D | α1 |
| 451 | D | ε10 |
| 452 | D | κ3 |
| 453 | D | ε12 |
| 454 | D | γ⁷ |
| 455 | D | γ⁸ |
| 456 | D | γ⁹ |

EXAMPLE 35

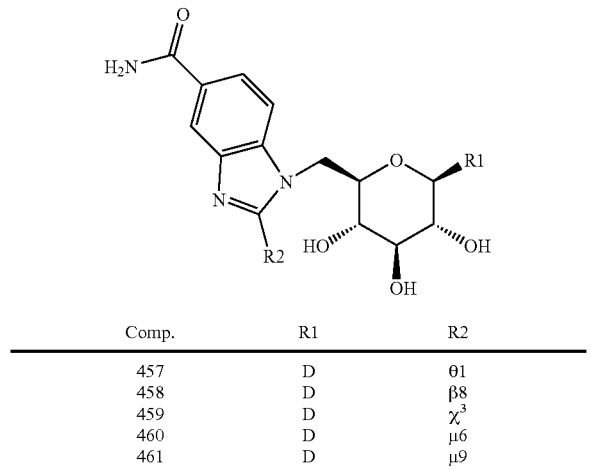

| Comp. | R1 | R2 |
|---|---|---|
| 457 | D | θ1 |
| 458 | D | β8 |
| 459 | D | $\chi^3$ |
| 460 | D | μ6 |
| 461 | D | μ9 |

EXAMPLE 36

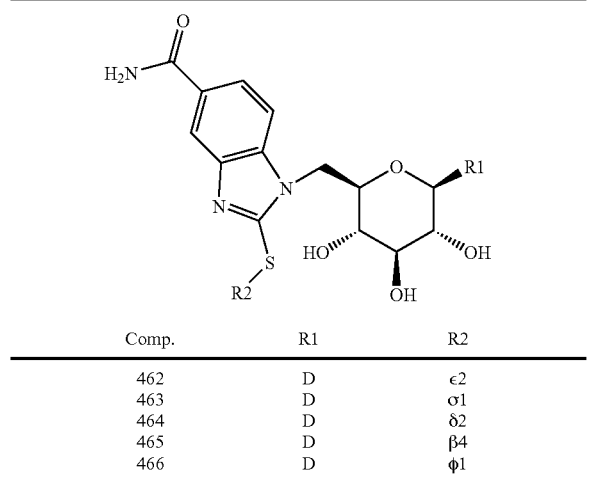

| Comp. | R1 | R2 |
|---|---|---|
| 462 | D | ε2 |
| 463 | D | σ1 |
| 464 | D | δ2 |
| 465 | D | β4 |
| 466 | D | φ1 |

EXAMPLE 37

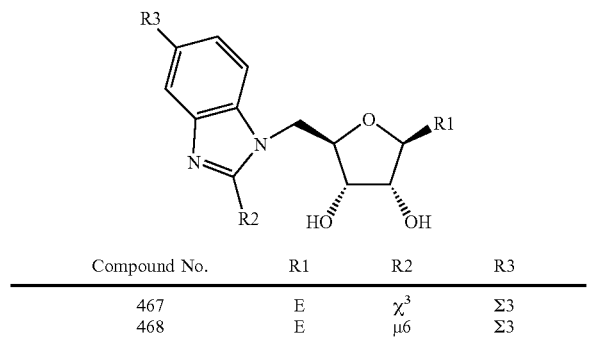

| Compound No. | R1 | R2 | R3 |
|---|---|---|---|
| 467 | E | $\chi^3$ | Σ3 |
| 468 | E | μ6 | Σ3 |

-continued

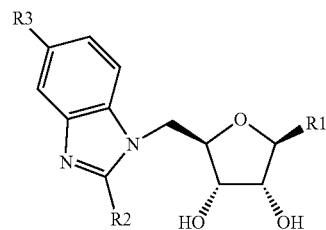

| Compound No. | R1 | R2 | R3 |
|---|---|---|---|
| 469 | E | $\chi^2$ | Σ3 |
| 470 | E | $\chi^3$ | ψ1 |
| 471 | E | μ6 | ψ1 |
| 472 | E | σ3 | ψ1 |
| 473 | E | $\chi^4$ | ψ1 |
| 474 | E | $\chi^2$ | ψ1 |
| 475 | C | $\chi^3$ | ψ1 |
| 476 | C | μ6 | ψ1 |
| 477 | C | σ3 | ψ1 |
| 478 | C | $\chi^4$ | ψ1 |
| 479 | C | $\chi^2$ | ψ1 |
| 480 | A | $\chi^3$ | ψ1 |
| 481 | A | μ6 | ψ1 |
| 482 | A | σ3 | ψ1 |
| 483 | A | $\chi^4$ | ψ1 |
| 484 | A | $\chi^2$ | ψ1 |

EXAMPLE 38

| Compound No | R1 | R2 | R3 |
|---|---|---|---|
| 485 | A | $\chi^5$ | ψ1 |
| 486 | A | $\chi^9$ | ψ1 |
| 487 | A | $\chi^7$ | ψ1 |
| 488 | A | $\chi^{10}$ | ψ1 |
| 489 | A | $\chi^{11}$ | ψ1 |
| 490 | A | $\chi^{12}$ | ψ1 |
| 491 | A | $\chi^{13}$ | ψ1 |
| 492 | A | $\chi^{14}$ | ψ1 |
| 493 | A | $\chi^{15}$ | ψ1 |
| 494 | A | $\chi^{16}$ | ψ1 |
| 495 | A | $\chi^{17}$ | ψ1 |
| 496 | A | $\chi^{18}$ | ψ1 |
| 497 | A | $\chi^{19}$ | ψ1 |
| 498 | A | $\chi^{23}$ | ψ1 |
| 499 | A | σ4 | ψ1 |
| 500 | A | $\chi^{20}$ | ψ1 |
| 501 | A | ξ4 | ψ1 |
| 502 | A | β11 | ψ1 |
| 503 | A | $\chi^{21}$ | ψ1 |
| 504 | A | $\chi^{22}$ | ψ1 |
| 505 | C | $\chi^5$ | ψ1 |
| 506 | C | $\chi^9$ | ψ1 |
| 507 | C | $\chi^7$ | ψ1 |

-continued

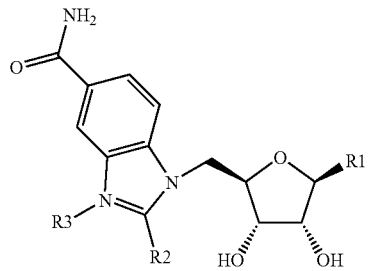

| Compound No | R1 | R2 | R3 |
|---|---|---|---|
| 508 | C | $\chi^{10}$ | $\psi 1$ |
| 509 | C | $\chi^{11}$ | $\psi 1$ |
| 510 | C | $\chi^{12}$ | $\psi 1$ |
| 511 | C | $\chi^{13}$ | $\psi 1$ |
| 512 | C | $\chi^{14}$ | $\psi 1$ |
| 513 | C | $\chi^{15}$ | $\psi 1$ |
| 514 | C | $\chi^{16}$ | $\psi 1$ |
| 515 | C | $\chi^{17}$ | $\psi 1$ |
| 516 | C | $\chi^{18}$ | $\psi 1$ |
| 517 | C | $\chi^{19}$ | $\psi 1$ |
| 518 | C | $\chi^{23}$ | $\psi 1$ |
| 519 | C | $\sigma 4$ | $\psi 1$ |
| 520 | C | $\chi^{20}$ | $\psi 1$ |
| 521 | C | $\xi 4$ | $\psi 1$ |
| 522 | C | $\beta 11$ | $\psi 1$ |
| 523 | C | $\chi^{21}$ | $\psi 1$ |
| 524 | C | $\chi^{22}$ | $\psi 1$ |
| 525 | D | $\chi^{5}$ | $\psi 1$ |
| 526 | D | $\chi^{9}$ | $\psi 1$ |
| 527 | D | $\chi^{7}$ | $\psi 1$ |
| 528 | D | $\chi^{10}$ | $\psi 1$ |
| 529 | D | $\chi^{11}$ | $\psi 1$ |
| 530 | D | $\chi^{12}$ | $\psi 1$ |
| 531 | D | $\chi^{13}$ | $\psi 1$ |
| 532 | D | $\chi^{14}$ | $\psi 1$ |
| 533 | D | $\chi^{15}$ | $\psi 1$ |
| 534 | D | $\chi^{16}$ | $\psi 1$ |
| 535 | D | $\chi^{17}$ | $\psi 1$ |
| 536 | D | $\chi^{18}$ | $\psi 1$ |
| 537 | D | $\chi^{19}$ | $\psi 1$ |
| 538 | D | $\chi^{23}$ | $\psi 1$ |
| 539 | D | $\sigma 4$ | $\psi 1$ |
| 540 | D | $\chi^{20}$ | $\psi 1$ |
| 541 | D | $\xi 4$ | $\psi 1$ |
| 542 | D | $\beta 11$ | $\psi 1$ |
| 543 | D | $\chi^{21}$ | $\psi 1$ |
| 544 | D | $\chi^{22}$ | $\psi 1$ |
| 545 | A | $\chi^{5}$ | $\chi^{1}$ |
| 546 | A | $\chi^{9}$ | $\chi^{9-1}$ |
| 547 | A | $\chi^{7}$ | $\chi^{7-1}$ |
| 548 | A | $\chi^{10}$ | $\chi^{10-1}$ |
| 549 | A | $\chi^{11}$ | $\chi^{11-1}$ |
| 550 | A | $\chi^{12}$ | $\chi^{12-1}$ |
| 551 | A | $\chi^{13}$ | $\chi^{13-1}$ |
| 552 | A | $\chi^{14}$ | $\chi^{14-1}$ |
| 553 | A | $\chi^{15}$ | $\chi^{15-1}$ |
| 554 | A | $\chi^{16}$ | $\chi^{16-1}$ |
| 555 | A | $\chi^{17}$ | $\chi^{17-1}$ |
| 556 | A | $\chi^{18}$ | $\chi^{18-1}$ |
| 557 | A | $\chi^{19}$ | $\chi^{19-1}$ |
| 558 | A | $\chi^{23}$ | $\chi^{23-1}$ |
| 559 | A | $\sigma 4$ | $\sigma 4-1$ |
| 560 | A | $\chi^{20}$ | $\chi^{20-1}$ |
| 561 | A | $\xi 4$ | $\xi 4-1$ |
| 562 | A | $\beta 11$ | $\beta 4$ |
| 563 | A | $\chi^{22}$ | $\chi^{22-1}$ |
| 564 | C | $\chi^{5}$ | $\chi^{1}$ |
| 565 | C | $\chi^{9}$ | $\chi^{9-1}$ |
| 566 | C | $\chi^{7}$ | $\chi^{7-1}$ |
| 567 | C | $\chi^{10}$ | $\chi^{10-1}$ |
| 568 | C | $\chi^{11}$ | $\chi^{11-1}$ |
| 569 | C | $\chi^{12}$ | $\chi^{12-1}$ |
| 570 | C | $\chi^{13}$ | $\chi^{13-1}$ |

-continued

| Compound No | R1 | R2 | R3 |
|---|---|---|---|
| 571 | C | $\chi^{14}$ | $\chi^{14-1}$ |
| 572 | C | $\chi^{15}$ | $\chi^{15-1}$ |
| 573 | C | $\chi^{16}$ | $\chi^{16-1}$ |
| 574 | C | $\chi^{17}$ | $\chi^{17-1}$ |
| 575 | C | $\chi^{18}$ | $\chi^{18-1}$ |
| 576 | C | $\chi^{19}$ | $\chi^{19-1}$ |
| 577 | C | $\chi^{23}$ | $\chi^{23-1}$ |
| 578 | C | $\sigma 4$ | $\sigma 4-1$ |
| 579 | C | $\chi^{20}$ | $\chi^{20-1}$ |
| 580 | C | $\xi 4$ | $\xi 4-1$ |
| 581 | C | $\beta 11$ | $\beta 4$ |
| 582 | C | $\chi^{22}$ | $\chi^{22-1}$ |
| 583 | D | $\chi^{5}$ | $\chi^{1}$ |
| 584 | D | $\chi^{9}$ | $\chi^{9-1}$ |
| 585 | D | $\chi^{7}$ | $\chi^{7-1}$ |
| 586 | D | $\chi^{10}$ | $\chi^{10-1}$ |
| 587 | D | $\chi^{11}$ | $\chi^{11-1}$ |
| 588 | D | $\chi^{12}$ | $\chi^{12-1}$ |
| 589 | D | $\chi^{13}$ | $\chi^{13-1}$ |
| 590 | D | $\chi^{14}$ | $\chi^{14-1}$ |
| 591 | D | $\chi^{15}$ | $\chi^{15-1}$ |
| 592 | D | $\chi^{16}$ | $\chi^{16-1}$ |
| 593 | D | $\chi^{17}$ | $\chi^{17-1}$ |
| 594 | D | $\chi^{18}$ | $\chi^{18-1}$ |
| 595 | D | $\chi^{19}$ | $\chi^{19-1}$ |
| 596 | D | $\chi^{23}$ | $\chi^{23-1}$ |
| 597 | D | $\sigma 4$ | $\sigma 4-1$ |
| 598 | D | $\xi 4$ | $\xi 4-1$ |
| 599 | D | $\beta 11$ | $\beta 4$ |
| 600 | D | $\chi^{22}$ | $\chi^{22-1}$ |

EXAMPLE 39

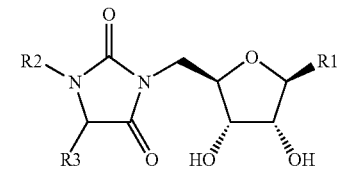

| Compound No | R1 | R2 | R3 |
|---|---|---|---|
| 601 | A | $\xi 1$ | $\alpha 1$ |
| 602 | A | $\epsilon 5$ | $\alpha 1$ |
| 603 | A | $\epsilon 2$ | $\alpha 1$ |
| 604 | A | $\tau 1$ | $\alpha 1$ |
| 605 | A | $\tau 2$ | $\alpha 1$ |
| 606 | A | $\mu 3$ | $\alpha 1$ |
| 607 | E | $\tau 2$ | $\alpha 1$ |
| 608 | E | $\mu 2$ | $\alpha 1$ |
| 609 | E | $\mu 3$ | $\alpha 1$ |
| 610 | E | $\gamma^{5}$ | $\alpha 1$ |

EXAMPLE 40

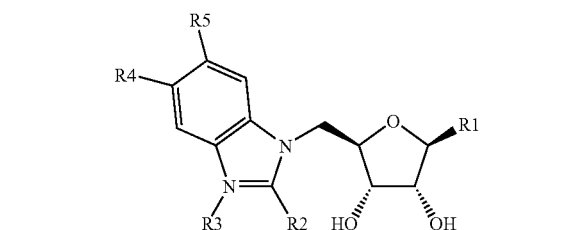

| Compound No | R1 | R2 | R3 | R4 | R5 |
|---|---|---|---|---|---|
| 611 | C | $\chi^4$ | | $\psi1$ | $\psi1$ |
| 612 | F | $\chi^5$ | | $\psi1$ | $\psi1$ |
| 613 | D | $\chi^5$ | | $\psi1$ | $\psi1$ |
| 614 | C | $\chi^5$ | | $\psi1$ | $\psi1$ |
| 615 | G | $\chi^5$ | | $\psi1$ | $\psi1$ |
| 616 | H | $\chi^5$ | | $\psi1$ | $\psi1$ |
| 617 | F | $\chi^5$ | | $\kappa5$ | $\psi1$ |
| 618 | D | $\chi^5$ | | $\kappa5$ | $\psi1$ |
| 619 | C | $\chi^5$ | | $\kappa5$ | $\psi1$ |
| 620 | G | $\chi^5$ | | $\kappa5$ | $\psi1$ |
| 621 | H | $\chi^5$ | | $\kappa5$ | $\psi1$ |
| 622 | F | $\chi^5$ | | $\psi1$ | $\nu5$ |
| 623 | D | $\chi^5$ | | $\psi1$ | $\nu5$ |
| 624 | C | $\chi^5$ | | $\psi1$ | $\nu5$ |
| 625 | G | $\chi^5$ | | $\psi1$ | $\nu5$ |
| 626 | H | $\chi^5$ | | $\psi1$ | $\nu5$ |
| 627 | F | $\chi^5$ | | $\beta12$ | $\beta12$ |
| 628 | D | $\chi^5$ | | $\beta12$ | $\beta12$ |
| 629 | C | $\chi^5$ | | $\beta12$ | $\beta12$ |
| 630 | G | $\chi^5$ | | $\beta12$ | $\beta12$ |
| 631 | H | $\chi^5$ | | $\beta12$ | $\beta12$ |
| 632 | F | $\chi^{18}$ | | $\psi1$ | $\psi1$ |
| 633 | D | $\chi^{18}$ | | $\psi1$ | $\psi1$ |
| 634 | C | $\chi^{18}$ | | $\psi1$ | $\psi1$ |
| 635 | G | $\chi^{18}$ | | $\psi1$ | $\psi1$ |
| 636 | H | $\chi^{18}$ | | $\psi1$ | $\psi1$ |
| 637 | F | $\chi^{18}$ | | $\kappa5$ | $\psi1$ |
| 638 | D | $\chi^{18}$ | | $\kappa5$ | $\psi1$ |
| 639 | C | $\chi^{18}$ | | $\kappa5$ | $\psi1$ |
| 640 | G | $\chi^{18}$ | | $\kappa5$ | $\psi1$ |
| 641 | H | $\chi^{18}$ | | $\kappa5$ | $\psi1$ |
| 642 | F | $\chi^{18}$ | | $\psi1$ | $\nu5$ |
| 643 | D | $\chi^{18}$ | | $\psi1$ | $\nu5$ |
| 644 | C | $\chi^{18}$ | | $\psi1$ | $\nu5$ |
| 645 | G | $\chi^{18}$ | | $\psi1$ | $\nu5$ |
| 646 | H | $\chi^{18}$ | | $\psi1$ | $\nu5$ |
| 647 | F | $\chi^{18}$ | | $\beta12$ | $\beta12$ |
| 648 | D | $\chi^{18}$ | | $\beta12$ | $\beta12$ |
| 649 | C | $\chi^{18}$ | | $\beta12$ | $\beta12$ |
| 650 | G | $\chi^{18}$ | | $\beta12$ | $\beta12$ |
| 651 | H | $\chi^{18}$ | | $\beta12$ | $\beta12$ |
| 652 | F | $\chi^4$ | | $\psi1$ | $\psi1$ |
| 653 | D | $\chi^4$ | | $\psi1$ | $\psi1$ |
| 654 | G | $\chi^4$ | | $\psi1$ | $\psi1$ |
| 655 | H | $\chi^4$ | | $\psi1$ | $\psi1$ |
| 656 | F | $\chi^4$ | | $\kappa5$ | $\psi1$ |
| 657 | D | $\chi^4$ | | $\kappa5$ | $\psi1$ |
| 658 | C | $\chi^4$ | | $\kappa5$ | $\psi1$ |
| 659 | G | $\chi^4$ | | $\kappa5$ | $\psi1$ |
| 660 | H | $\chi^4$ | | $\kappa5$ | $\psi1$ |
| 661 | F | $\chi^4$ | | $\psi1$ | $\nu5$ |
| 662 | D | $\chi^4$ | | $\psi1$ | $\nu5$ |
| 663 | C | $\chi^4$ | | $\psi1$ | $\nu5$ |
| 664 | G | $\chi^4$ | | $\psi1$ | $\nu5$ |
| 665 | H | $\chi^4$ | | $\psi1$ | $\nu5$ |
| 666 | F | $\chi^4$ | | $\beta12$ | $\beta12$ |
| 667 | D | $\chi^4$ | | $\beta12$ | $\beta12$ |
| 668 | C | $\chi^4$ | | $\beta12$ | $\beta12$ |
| 669 | G | $\chi^4$ | | $\beta12$ | $\beta12$ |
| 670 | H | $\chi^4$ | | $\beta12$ | $\beta12$ |
| 671 | F | $\chi^5$ | $\chi^1$ | $\psi1$ | $\psi1$ |
| 672 | D | $\chi^5$ | $\chi^1$ | $\psi1$ | $\psi1$ |

-continued

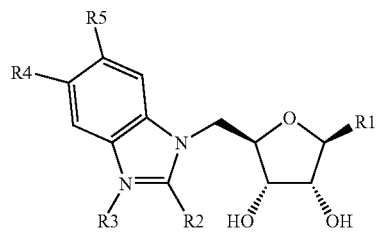

| Compound No | R1 | R2 | R3 | R4 | R5 |
|---|---|---|---|---|---|
| 673 | C | $\chi^5$ | $\chi^1$ | $\psi1$ | $\psi1$ |
| 674 | G | $\chi^5$ | $\chi^1$ | $\psi1$ | $\psi1$ |
| 675 | H | $\chi^5$ | $\chi^1$ | $\psi1$ | $\psi1$ |
| 676 | F | $\chi^5$ | $\chi^1$ | $\kappa5$ | $\psi1$ |
| 677 | D | $\chi^5$ | $\chi^1$ | $\kappa5$ | $\psi1$ |
| 678 | C | $\chi^5$ | $\chi^1$ | $\kappa5$ | $\psi1$ |
| 679 | G | $\chi^5$ | $\chi^1$ | $\kappa5$ | $\psi1$ |
| 680 | H | $\chi^5$ | $\chi^1$ | $\kappa5$ | $\psi1$ |
| 681 | F | $\chi^5$ | $\chi^1$ | $\psi1$ | $\nu5$ |
| 682 | D | $\chi^5$ | $\chi^1$ | $\psi1$ | $\nu5$ |
| 683 | C | $\chi^5$ | $\chi^1$ | $\psi1$ | $\nu5$ |
| 684 | G | $\chi^5$ | $\chi^1$ | $\psi1$ | $\nu5$ |
| 685 | H | $\chi^5$ | $\chi^1$ | $\psi1$ | $\nu5$ |
| 686 | D | $\chi^5$ | $\chi^1$ | $\beta12$ | $\beta12$ |
| 687 | C | $\chi^5$ | $\chi^1$ | $\beta12$ | $\beta12$ |
| 688 | G | $\chi^5$ | $\chi^1$ | $\beta12$ | $\beta12$ |
| 689 | H | $\chi^5$ | $\chi^1$ | $\beta12$ | $\beta12$ |
| 690 | F | $\chi^{18}$ | $\chi^{18-1}$ | $\psi1$ | $\psi1$ |
| 691 | C | $\chi^{18}$ | $\chi^{18-1}$ | $\psi1$ | $\psi1$ |
| 692 | G | $\chi^{18}$ | $\chi^{18-1}$ | $\psi1$ | $\psi1$ |
| 693 | H | $\chi^{18}$ | $\chi^{18-1}$ | $\psi1$ | $\psi1$ |
| 694 | H | $\chi^{18}$ | $\chi^{18-1}$ | $\kappa5$ | $\psi1$ |
| 695 | F | $\chi^{18}$ | $\chi^{18-1}$ | $\psi1$ | $\nu5$ |
| 696 | C | $\chi^{18}$ | $\chi^{18-1}$ | $\psi1$ | $\nu5$ |
| 697 | D | $\chi^{18}$ | $\chi^{18-1}$ | $\psi1$ | $\nu5$ |
| 698 | G | $\chi^{18}$ | $\chi^{18-1}$ | $\psi1$ | $\nu5$ |
| 699 | H | $\chi^{18}$ | $\chi^{18-1}$ | $\psi1$ | $\nu5$ |
| 700 | F | $\chi^{18}$ | $\chi^{18-1}$ | $\beta12$ | $\beta12$ |
| 701 | D | $\chi^{18}$ | $\chi^{18-1}$ | $\beta12$ | $\beta12$ |
| 702 | C | $\chi^{18}$ | $\chi^{18-1}$ | $\beta12$ | $\beta12$ |
| 703 | G | $\chi^{18}$ | $\chi^{18-1}$ | $\beta12$ | $\beta12$ |
| 704 | H | $\chi^{18}$ | $\chi^{18-1}$ | $\beta12$ | $\beta12$ |
| 705 | F | $\chi^4$ | $\chi^{24}$ | $\psi1$ | $\psi1$ |
| 706 | C | $\chi^4$ | $\chi^{24}$ | $\psi1$ | $\psi1$ |
| 707 | G | $\chi^4$ | $\chi^{24}$ | $\psi1$ | $\psi1$ |
| 708 | H | $\chi^4$ | $\chi^{24}$ | $\psi1$ | $\psi1$ |
| 709 | F | $\chi^4$ | $\chi^{24}$ | $\kappa5$ | $\psi1$ |
| 710 | D | $\chi^4$ | $\chi^{24}$ | $\kappa5$ | $\psi1$ |
| 711 | C | $\chi^4$ | $\chi^{24}$ | $\kappa5$ | $\psi1$ |
| 712 | H | $\chi^4$ | $\chi^{24}$ | $\kappa5$ | $\psi1$ |
| 713 | D | $\chi^4$ | $\chi^{24}$ | $\psi1$ | $\nu5$ |
| 714 | F | $\chi^4$ | $\chi^{24}$ | $\beta12$ | $\beta12$ |

EXAMPLE 41

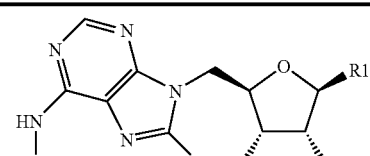

| Compound No. | R1 | R2 | R3 |
|---|---|---|---|
| 715 | A | $\chi^5$ | $\alpha1$ |
| 716 | C | $\chi^5$ | $\alpha1$ |
| 717 | A | $\chi^3$ | $\alpha1$ |

-continued

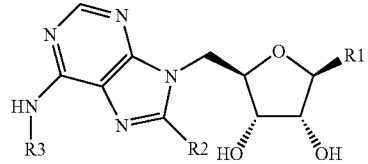

| Compound No. | R1 | R2 | R3 |
|---|---|---|---|
| 718 | C | $\chi^3$ | $\alpha1$ |
| 719 | A | $\sigma3$ | $\alpha1$ |
| 720 | C | $\sigma3$ | $\alpha1$ |
| 721 | A | $\chi^5$ | $\nu5$ |
| 722 | C | $\chi^5$ | $\nu5$ |
| 723 | C | $\chi^5$ | $\nu5$ |
| 724 | A | $\chi^3$ | $\nu5$ |
| 725 | C | $\chi^3$ | $\nu5$ |
| 726 | C | $\chi^3$ | $\nu5$ |
| 727 | A | $\sigma3$ | $\nu5$ |
| 728 | C | $\sigma3$ | $\nu5$ |
| 729 | C | $\sigma3$ | $\nu5$ |

EXAMPLE 42

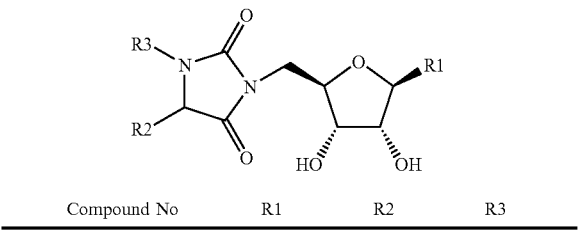

| Compound No | R1 | R2 | R3 |
|---|---|---|---|
| 730 | A | $\beta2$ | $\alpha1$ |
| 731 | A | $\epsilon5$ | $\alpha1$ |
| 732 | A | $\beta3$ | $\alpha1$ |
| 733 | A | $\chi^{19}$ | $\alpha1$ |
| 734 | A | $\chi^1$ | $\alpha1$ |
| 735 | A | $\gamma^{10}$ | $\alpha1$ |
| 736 | A | $\xi5$ | $\alpha1$ |
| 737 | A | $\sigma1$ | $\alpha1$ |
| 738 | A | $\chi^{4-1}$ | $\alpha1$ |
| 739 | A | $\mu10$ | $\alpha1$ |
| 740 | A | $\phi2$ | $\alpha1$ |
| 741 | A | $\alpha4$ | $\alpha1$ |
| 742 | A | $\alpha8$ | $\alpha1$ |
| 743 | A | $\beta2$ | $\beta2$ |
| 744 | A | $\epsilon5$ | $\beta2$ |
| 745 | A | $\beta3$ | $\beta2$ |
| 746 | A | $\chi^{19}$ | $\beta2$ |
| 747 | A | $\chi^1$ | $\beta2$ |
| 748 | A | $\gamma^{10}$ | $\beta2$ |
| 749 | A | $\xi5$ | $\beta2$ |
| 750 | A | $\sigma1$ | $\beta2$ |
| 751 | A | $\chi^{4-1}$ | $\beta2$ |
| 752 | A | $\mu10$ | $\beta2$ |
| 753 | A | $\phi2$ | $\beta2$ |
| 754 | A | $\alpha4$ | $\beta2$ |
| 755 | A | $\alpha8$ | $\beta2$ |
| 756 | A | $\beta2$ | $\epsilon5$ |
| 757 | A | $\epsilon5$ | $\epsilon5$ |
| 758 | A | $\beta3$ | $\epsilon5$ |
| 759 | A | $\chi^{19}$ | $\epsilon5$ |
| 760 | A | $\chi^1$ | $\epsilon5$ |
| 761 | A | $\gamma^{10}$ | $\epsilon5$ |
| 762 | A | $\xi5$ | $\epsilon5$ |
| 763 | A | $\sigma1$ | $\epsilon5$ |
| 764 | A | $\chi^{4-1}$ | $\epsilon5$ |
| 765 | A | $\mu10$ | $\epsilon5$ |

-continued

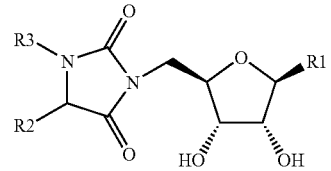

| Compound No | R1 | R2 | R3 |
|---|---|---|---|
| 766 | A | $\phi2$ | $\epsilon5$ |
| 767 | A | $\alpha4$ | $\epsilon5$ |
| 768 | A | $\alpha8$ | $\epsilon5$ |
| 769 | A | $\beta2$ | $\xi1$ |
| 770 | A | $\epsilon5$ | $\xi1$ |
| 771 | A | $\beta3$ | $\xi1$ |
| 772 | A | $\chi^1$ | $\xi1$ |
| 773 | A | $\gamma^{10}$ | $\xi1$ |
| 774 | A | $\sigma1$ | $\xi1$ |
| 775 | A | $\chi^{4-1}$ | $\xi1$ |
| 776 | A | $\mu10$ | $\xi1$ |
| 777 | A | $\phi2$ | $\xi1$ |
| 778 | A | $\alpha4$ | $\xi1$ |
| 779 | A | $\alpha8$ | $\xi1$ |
| 780 | A | $\beta2$ | $\psi1$ |
| 781 | A | $\beta2$ | $\xi5$ |
| 782 | A | $\epsilon5$ | $\psi1$ |
| 783 | A | $\epsilon5$ | $\xi5$ |
| 784 | A | $\beta3$ | $\psi1$ |
| 785 | A | $\beta3$ | $\xi5$ |
| 786 | A | $\chi^1$ | $\psi1$ |
| 787 | A | $\chi^1$ | $\xi5$ |
| 788 | A | $\gamma^{10}$ | $\psi1$ |
| 789 | A | $\gamma^{10}$ | $\xi5$ |
| 790 | A | $\xi5$ | $\psi1$ |
| 791 | A | $\xi5$ | $\xi5$ |
| 792 | A | $\sigma1$ | $\psi1$ |
| 793 | A | $\sigma1$ | $\xi5$ |
| 794 | A | $\chi^{4-1}$ | $\psi1$ |
| 795 | A | $\mu10$ | $\psi1$ |
| 796 | A | $\mu10$ | $\xi5$ |
| 797 | A | $\phi2$ | $\psi1$ |
| 798 | A | $\phi2$ | $\xi5$ |
| 799 | A | $\alpha8$ | $\xi5$ |
| 800 | A | $\alpha8$ | $\xi5$ |
| 801 | A | $\beta2$ | $\omega1$ |
| 802 | A | $\epsilon5$ | $\omega1$ |
| 803 | A | $\beta3$ | $\omega1$ |
| 804 | A | $\chi^{19}$ | $\omega1$ |
| 805 | A | $\chi^1$ | $\omega1$ |
| 806 | A | $\chi^{19}$ | $\psi1$ |
| 807 | A | $\chi^{19}$ | $\xi5$ |
| 808 | A | $\phi2$ | $\omega1$ |
| 809 | A | $\mu10$ | $\gamma^1$ |
| 810 | A | $\phi2$ | $\gamma^1$ |
| 811 | A | $\alpha4$ | $\gamma^1$ |
| 812 | A | $\alpha8$ | $\gamma1$ |
| 813 | A | $\beta2$ | $\kappa2$ |
| 814 | A | $\epsilon5$ | $\kappa2$ |
| 815 | A | $\beta3$ | $\kappa2$ |
| 816 | A | $\chi^{19}$ | $\kappa2$ |
| 817 | A | $\chi^1$ | $\kappa2$ |
| 818 | A | $\gamma^{10}$ | $\kappa2$ |
| 819 | A | $\chi^5$ | $\kappa2$ |
| 820 | A | $\sigma1$ | $\kappa2$ |
| 821 | A | $\chi^{4-1}$ | $\kappa2$ |
| 822 | A | $\mu10$ | $\kappa2$ |
| 823 | A | $\phi2$ | $\kappa2$ |
| 824 | A | $\alpha4$ | $\kappa2$ |
| 825 | A | $\alpha8$ | $\kappa2$ |
| 826 | A | $\beta2$ | $\tau2$ |
| 827 | A | $\epsilon5$ | $\tau2$ |
| 828 | A | $\beta3$ | $\tau2$ |
| 829 | A | $\chi^{19}$ | $\tau2$ |
| 830 | A | $\chi^1$ | $\tau2$ |
| 831 | A | $\gamma^{10}$ | $\tau2$ |
| 832 | A | $\chi^5$ | $\tau2$ |

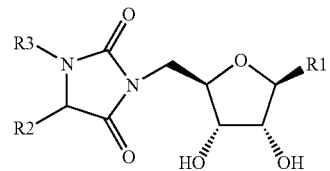

| Compound No | R1 | R2 | R3 |
|---|---|---|---|
| 833 | A | σ1 | τ2 |
| 834 | A | χ$^{4-1}$ | τ2 |
| 835 | A | μ10 | τ2 |
| 836 | A | φ2 | τ2 |
| 837 | A | α4 | τ2 |
| 838 | A | α8 | τ2 |
| 839 | A | β2 | τ2 |
| 840 | A | ε5 | μ2 |
| 841 | A | β3 | μ2 |
| 842 | A | χ$^{19}$ | μ2 |
| 843 | A | χ$^1$ | μ2 |
| 844 | A | γ$^{10}$ | μ2 |
| 845 | A | χ$^5$ | μ2 |
| 846 | A | μ2 | μ2 |
| 847 | A | χ$^{4-1}$ | μ2 |
| 848 | A | μ10 | μ2 |
| 849 | A | φ2 | μ2 |
| 850 | A | α4 | μ2 |
| 851 | A | α8 | μ2 |
| 852 | A | β2 | χ$^1$ |
| 853 | A | ε5 | χ$^1$ |
| 854 | A | β3 | χ$^1$ |
| 855 | A | χ$^{19}$ | χ$^1$ |
| 856 | A | χ$^1$ | χ$^1$ |
| 857 | A | γ$^{10}$ | χ$^1$ |
| 858 | A | χ$^5$ | χ$^1$ |
| 859 | A | σ1 | χ$^1$ |
| 860 | A | ξ4-1 | χ$^1$ |
| 861 | A | φ2 | χ$^1$ |
| 862 | A | α4 | χ$^1$ |
| 863 | A | α8 | χ$^1$ |
| 864 | A | β2 | Σ4 |
| 865 | A | ε5 | Σ4 |
| 866 | A | β3 | Σ4 |
| 867 | A | χ$^{19}$ | Σ4 |
| 868 | A | χ$^1$ | Σ4 |
| 869 | A | γ$^{10}$ | Σ4 |
| 870 | A | χ$^5$ | Σ4 |
| 871 | A | σ1 | Σ4 |
| 872 | A | χ$^{4-1}$ | Σ4 |
| 873 | A | μ10 | Σ4 |
| 874 | A | φ2 | Σ4 |
| 875 | A | α4 | Σ4 |
| 876 | A | α8 | Σ4 |
| 877 | A | α1 | ν1 |
| 878 | A | α1 | ν2 |
| 879 | A | α1 | ν9 |
| 880 | A | ν4 | α1 |
| 881 | A | ν4 | γ$^2$ |
| 882 | A | ν4 | τ2 |
| 883 | A | ν4 | τ1 |
| 884 | A | χ$^1$ | ν4 |
| 885 | A | μ7-1 | α1 |
| 886 | A | μ7-1 | γ$^2$ |
| 887 | A | μ7-1 | τ2 |
| 888 | A | μ7-1 | τ1 |
| 889 | A | μ7-1 | χ$^1$ |
| 890 | A | γ$^{10}$ | ε1 |
| 891 | A | χ$^5$ | ω1 |
| 892 | A | σ1 | ω1 |

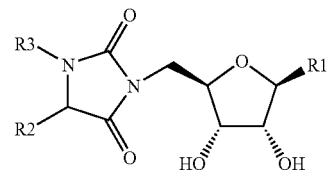

| Compound No | R1 | R2 | R3 |
|---|---|---|---|
| 893 | A | χ$^{4-1}$ | ω1 |
| 894 | A | μ10 | ω1 |
| 895 | A | α4 | ω1 |
| 896 | A | α8 | ω1 |
| 897 | A | β2 | γ$^1$ |
| 898 | A | ε5 | γ$^1$ |
| 899 | A | β3 | γ$^1$ |
| 900 | A | χ$^{19}$ | γ$^1$ |
| 901 | A | χ$^1$ | γ$^1$ |
| 902 | A | γ$^{10}$ | γ$^1$ |
| 903 | A | ξ5 | γ$^1$ |
| 904 | A | σ1 | γ1 |
| 905 | A | χ$^{4-1}$ | γ$^1$ |
| 906 | A | μ11 | χ$^1$ |
| 907 | A | μ11 | τ2 |
| 908 | A | ν4 | μ3 |
| 909 | A | α1 | σ1 |
| 910 | A | σ1 | β2 |
| 911 | A | σ1 | ε5 |

EXAMPLE 43

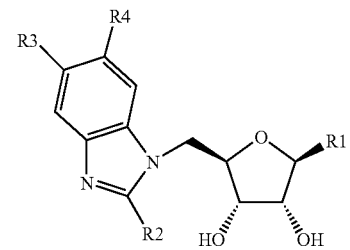

| Compound No | R1 | R2 | R3 | R4 |
|---|---|---|---|---|
| 912 | A | χ$^4$ | ψ1 | ψ1 |
| 913 | A | χ$^5$ | ψ1 | ψ1 |
| 914 | A | χ18 | ψ1 | ψ1 |
| 915 | A | χ$^5$ | ψ1 | ν5 |
| 916 | A | χ18 | ψ1 | ν5 |
| 917 | A | χ$^5$ | κ5 | ψ1 |
| 918 | A | χ$^4$ | κ5 | ψ1 |
| 919 | A | χ18 | κ5 | ψ1 |
| 920 | A | χ$^5$ | β12 | β12 |
| 921 | A | χ$^4$ | β12 | β12 |
| 922 | A | χ18 | β12 | β12 |

EXAMPLE 44
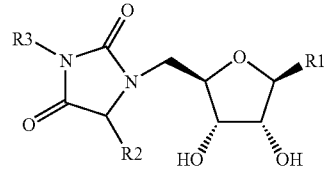
| Compound No | R1 | R2 | R3 |
|---|---|---|---|
| 923 | A | α1 | α4 |
| 924 | A | α1 | β6 |
| 925 | A | α1 | ε9 |
| 926 | A | α1 | κ6 |
| 927 | A | α1 | σ3 |
| 928 | A | α1 | χ8 |
| 929 | A | ψ1 | α4 |
| 930 | A | ψ1 | β6 |
| 931 | A | ψ1 | ε9 |
| 932 | A | ψ1 | κ6 |
| 933 | A | ψ1 | σ3 |
| 934 | A | ψ1 | χ8 |
| 935 | A | μ7-1 | α4 |
| 936 | A | μ7-1 | β6 |
| 937 | A | μ7-1 | ε9 |
| 938 | A | μ7-1 | κ6 |
| 939 | A | μ7-1 | σ3 |
| 940 | A | μ7-1 | χ8 |
| 941 | A | μ13 | α4 |
| 942 | A | μ13 | β6 |
| 943 | A | μ13 | ε9 |
| 944 | A | μ13 | κ6 |
| 945 | A | μ13 | σ3 |
| 946 | A | μ13 | χ8 |
| 947 | A | α1 | α4 |
| 948 | A | α1 | β6 |
| 949 | A | μ7-1 | α4 |
| 950 | A | μ7-1 | β6 |
| 951 | A | μ7-1 | σ3 |
| 952 | A | μ13 | σ3 |
| 953 | A | μ13 | χ8 |
EXAMPLE 45
| Compound No | R1 | R2 | R3 |
|---|---|---|---|
| 954 | A | β4 | α1 |
| 955 | A | β2 | α1 |
-continued
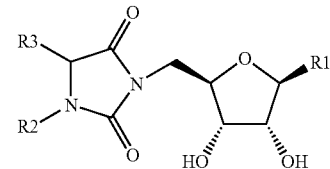
| Compound No | R1 | R2 | R3 |
|---|---|---|---|
| 956 | A | ε3 | α1 |
| 957 | A | γ2 | α1 |
| 958 | A | γ1 | α1 |
| 959 | A | β3 | α1 |
| 960 | A | β4 | α1 |
| 961 | A | β2 | α1 |
| 962 | A | ε3 | α1 |
| 963 | A | γ2 | α1 |
| 964 | A | γ1 | α1 |
| 965 | A | β3 | α1 |
EXAMPLE 46
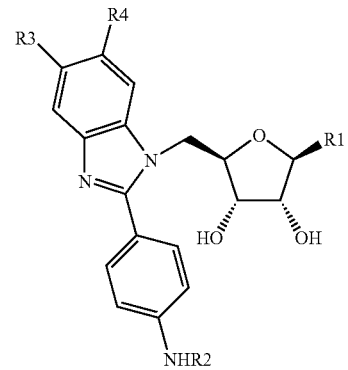
| Compound No | R1 | R2 | R3 | R4 |
|---|---|---|---|---|
| 966 | C | α1 | ψ1 | ψ1 |
| 967 | G | α1 | ψ1 | ψ1 |
| 968 | H | α1 | ψ1 | ψ1 |
| 969 | C | α1 | κ5 | ψ1 |
| 970 | G | α1 | κ5 | ψ1 |
| 971 | H | α1 | κ5 | ψ1 |
| 972 | C | α1 | ψ1 | ν5 |
| 973 | G | α1 | ψ1 | ν5 |
| 974 | H | α1 | ψ1 | ν5 |
| 975 | C | α1 | β12 | β12 |
| 976 | G | α1 | β12 | β12 |
| 977 | h | α1 | β12 | β12 |

EXAMPLE 47
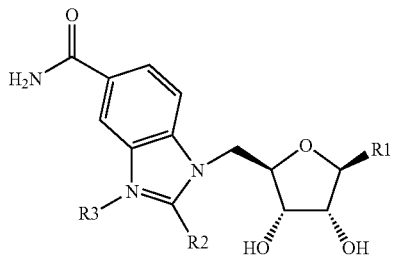
| Compound No | R1 | R2 | R3 |
|---|---|---|---|
| 978 | A | σ2 | σ2-1 |
| 979 | A | ξ2 | ξ2-1 |
| 980 | A | β6 | β2 |
| 981 | A | θ1 | θ3 |
| 982 | A | ε8 | ε1 |
| 983 | A | β8 | β3 |
| 984 | A | π5 | π1 |
| 985 | A | τ3 | τ1 |
| 986 | A | α3 | α3-1 |
| 987 | A | τ4 | τ2 |
| 988 | A | σ3 | σ1 |
| 989 | C | χ2 | χ2-1 |
| 990 | C | χ3 | ξ3-1 |
| 991 | C | χ4 | χ4-1 |
| 992 | C | ν8 | ν1 |
| 993 | C | μ5 | μ5-1 |
| 994 | C | τ3 | τ1 |
| 995 | C | τ4 | τ2 |
| 996 | C | μ6 | μ6-1 |
| 997 | D | σ2 | σ2-1 |
| 998 | D | ξ2 | ξ2-1 |
| 999 | D | β6 | β2 |
| 1000 | D | φ1 | φ1-1 |
| 1001 | D | χ4 | χ4-1 (χ24) |
| 1002 | D | ν8 | ν1 |
| 1003 | D | τ4 | τ2 |
| 1004 | D | σ3 | σ1 |
| 1005 | D | β9 | β9-1 |
| 1006 | D | μ6 | μ6-1 |
| 1007 | A | χ2 | χ2-1 |
EXAMPLE 48
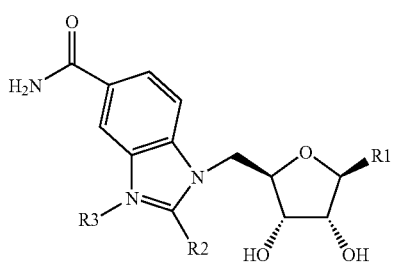
| Compound No | R1 | R2 | R3 |
|---|---|---|---|
| 1008 | A | α4 | α1 |
| 1009 | A | ε11 | ε3 |
| 1010 | A | χ8 | χ8-1 |
| 1011 | A | ε9 | ε5 |
| 1012 | A | ε2 | ε1 |
-continued
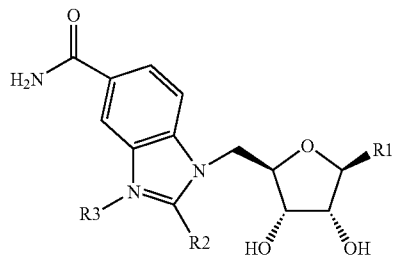
| Compound No | R1 | R2 | R3 |
|---|---|---|---|
| 1013 | A | α6 | α6-1 |
| 1014 | A | φ3 | φ2 |
| 1015 | A | τ4 | τ5 |
| 1016 | A | α7 | α7-1 |
| 1017 | A | α1 | α5 |
| 1018 | A | ε10 | ε2 |
| 1019 | A | κ3 | κ7 |
| 1020 | A | ε12 | ε7 |
| 1021 | A | γ7 | γ4 |
| 1022 | A | γ8 | γ8-1 |
| 1023 | A | γ9 | γ5 |
| 1024 | C | α4 | α1 |
| 1025 | C | θ1 | θ3 |
| 1026 | C | ε11 | ε3 |
| 1027 | C | χ8 | χ8-1 |
| 1028 | C | ε9 | ε5 |
| 1029 | C | ε3 | ε1 |
| 1030 | C | α6 | α6-1 |
| 1031 | C | φ3 | φ2 |
| 1032 | C | τ4 | τ5 |
| 1033 | C | α7 | α7-1 |
| 1034 | C | α1 | α5 |
| 1035 | C | ε10 | ε2 |
| 1036 | C | κ3 | κ7 |
| 1037 | C | ε12 | ε7 |
| 1038 | C | γ7 | γ4 |
| 1039 | C | γ8 | γ8-1 |
| 1040 | C | γ9 | γ5 |
| 1041 | D | α4 | α1 |
| 1042 | D | θ1 | θ3 |
| 1043 | D | ε11 | ε3 |
| 1044 | D | χ8 | χ8-1 |
| 1045 | D | ε9 | ε5 |
| 1046 | D | ε2 | ε1 |
| 1047 | D | α6 | α6-1 |
| 1048 | D | φ3 | φ2 |
| 1049 | D | α7 | α7-1 |
| 1050 | D | ε10 | ε2 |
| 1051 | D | κ3 | κ7 |
| 1052 | D | ε12 | ε7 |
| 1053 | D | γ7 | γ4 |
| 1054 | D | γ8 | γ8-1 |
| 1055 | D | γ9 | γ5 |

EXAMPLE 49

Selected Activity Data Tested at 25 Micromolar except ! Tested at 2.5 Micromolar.

| compound number | EGF-R | c-Kit | VEGF | ABL | MET | PDGFalpha | CDK2 | Tie2 | PKC | P38 |
|---|---|---|---|---|---|---|---|---|---|---|
| 100 | 69 | 52 | 58 | 109 | 88 | 106 | 70 | 42 | 80 | |
| 146 | 94 | 53 | 101 | 115 | 78 | 127 | 270 | 71 | 142 | |
| 212 | 23 | 12 | 10 | 41 | 46 | 38 | 25 | 1 | 26 | |
| 223 | 22 | 109 | 11 | 24 | 31 | 17 | 40 | 0 | 10 | |
| 246 | 15 | 6 | 8 | 30 | 27 | 28 | 26 | −1 | 13 | |
| 279 | 66 | 17 | 31 | 6 | 72 | 85 | 20 | 12 | 80 | |
| 345 | 58 | 40 | 54 | 74 | 87 | 82 | 67 | 41 | 65 | |
| 456 | 96 | 92 | 96 | 107 | 103 | 113 | 28 | 91 | 104 | |
| 466 | 84 | 55 | 72 | 110 | 102 | 104 | 114 | 88 | 87 | |
| 486! | | 24 | 45 | | | | | 96 | | 100 |
| 488! | | 34 | 136 | | | | | 82 | | 100 |
| 508! | | 12 | 17 | | | | | 16 | | 100 |
| 528! | | 12 | 44 | | | | | 26 | | 101 |
| 604 | 27 | 13 | 18 | 49 | 46 | 46 | 30 | 3 | 50 | 100 |
| 605 | 20 | 18 | 14 | 55 | 54 | 56 | 26 | 5 | 27 | 100 |
| 658! | | 20 | 55 | | | | | 5 | | 99 |
| 659! | | 17 | 63 | | | | | 8 | | 94 |
| 668! | | 16 | | | | | | 1 | | |
| 669! | | 11 | 34 | | | | | 1 | | 97 |
| 670! | | 9 | 23 | | | | | 1 | | |
| 718! | | 7 | 8 | | | | | 1 | | |
| 725! | | 6 | | | | | | 10 | | |
| 912 | 88 | 38 | 44 | 96 | 88 | 96 | 119 | 72 | 96 | 70 |

Blank = not determined.

The following lists examples of compound numbers that demonstrate activity

EGF-R inhibitors at 25 micromolar: 470, 471, 472, 478, 480, 604, 605, 611, 100, 198, 205, 207, 209, 212, 213, 214, 215, 216, 218, 211, 220, 221, 222, 223, 224, 225, 227, 233, 235, 238, 240, 241, 246, 248, 254, 273, 279, 291, 334, 345, 350, 386, 391, 392, 393:

c-Kit inhibitors at 25 micromolar: 470, 471, 472, 473, 474, 480, 482, 483, 484, 604, 605, 611, 912, 486, 488, 501, 504, 508, 528, 606, 607, 608, 609, 610, 654, 657, 658, 659, 660, 663, 664, 665, 656, 667, 668, 669, 670, 99, 100, 103, 104, 108, 109, 110, 122, 125, 127, 130, 131, 132, 133, 135, 136, 137, 138, 139, 140, 143, 144, 145, 146, 148, 154, 155, 163, 168, 169, 170, 173, 174, 175, 177, 178, 180, 181, 183, 184, 186, 192, 193, 198, 204, 205, 207, 209, 212, 213, 214, 217, 218, 211, 220, 221, 222, 225, 227, 233, 235, 238, 240, 241, 246, 248, 254, 228, 242, 244, 245, 247, 250, 252, 253, 260, 261, 262, 271, 264, 273, 279, 282, 286, 289, 291, 299, 309, 321, 322, 332, 333, 334, 345, 346, 362, 370, 377, 378, 379, 386, 398, 403, 404, 408, 427, 458, 459, 460, 462, 463, 464, 465, 466:

VEGF-R2 inhibitors at 25 micromolar: 472, 478, 480, 482, 483, 484, 604, 605, 611, 912, 486, 505, 508, 528, 604, 605, 606, 608, 658, 659, 660, 667, 668, 669, 670, 100, 198, 205, 207, 209, 211, 212, 214, 215, 216, 218, 220, 221, 222, 223, 224, 225, 227, 233, 235, 238, 244, 246, 252, 254, 256, 271, 273, 279, 291, 345, 370, 371, 379, 403, 466:

ABL inhibitors at 25 micromolar: 470, 478, 480, 604, 605, 611, 107, 127, 135, 152, 156, 157, 158, 159, 191, 207, 212, 214, 215, 220, 221, 223, 224, 225, 233, 246, 273, 279, 291, 299, 330, 334, 345, 397:

MET inhibitors at 25 micromolar: 470, 480, 604, 605, 207, 212, 214, 217, 220, 221, 223, 224, 225, 233, 238, 246, 279, 291:

PDGF-Ralpha inhibitors at 25 micromolar: 470, 604, 605, 207, 212, 214, 215, 220, 221, 223, 224, 225, 233, 246, 202, 271, 321, 334, 370:

CDK2 inhibitors at 25 micromolar: 470, 472, 478, 604, 605, 611, 32, 100, 205, 207, 209, 212, 213, 214, 215, 216, 218, 219, 220, 221, 222, 223, 224, 225, 233, 246, 273, 279, 291, 334, 345, 456:

Tie2 inhibitors at 25 micromolar: 470, 471, 472, 474, 478, 480, 604, 605, 611, 912, 508, 528, 534, 535, 604, 605, 606, 607, 608, 609, 610, 654, 657, 658, 659, 660, 667, 668, 669, 670, 71, 91, 92, 99, 100, 101, 103, 104, 106, 107, 108, 109, 113, 114, 127, 131, 135, 136, 138, 139, 143, 144, 145, 146, 151, 152, 153, 154, 155, 160, 168, 177, 178, 183, 192, 198, 205, 207, 209, 211, 212, 217, 214, 215, 216, 218, 220, 221, 222, 223, 224, 225, 227, 231, 233, 235, 238, 240, 241, 244, 246, 248, 250, 252, 254, 256, 271, 273, 279, 291, 333, 334, 345, 376, 379, 446, 457, 459:

PK-C inhibitors at 25 micromolar: 470, 471, 472, 474, 478, 480, 604, 605, 611, 2, 205, 207, 209, 212, 213, 214, 215, 216, 218, 219, 220, 221, 222, 223, 224, 225, 233, 246, 299, 321, 333, 334, 345, 379:

FGF-R1 inhibitors at 25 micromolar: 604, 605, 611, 100, 104, 198, 205, 207, 211, 212, 214, 215, 216, 217, 218, 220, 221, 222, 223, 224, 225, 227, 233, 238, 246, 248, 254, 273, 279, 291, 345:

Tables of Substituents:
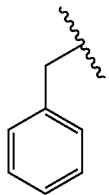
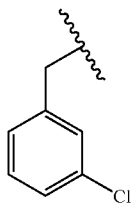
Cl
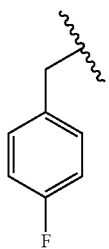
F
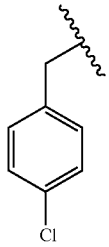
Cl
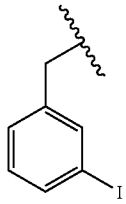
I
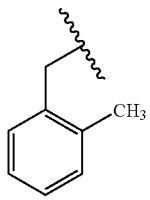
CH₃
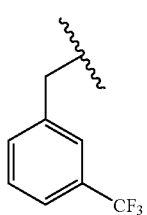
CF₃
α1
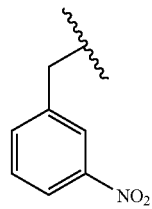
NO₂
β1
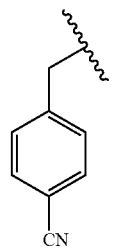
CN
γ1
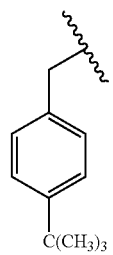
C(CH₃)₃
β2
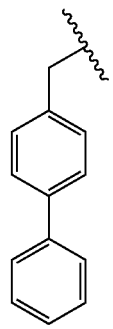
δ1
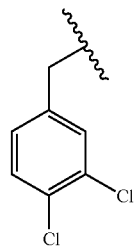
Cl
Cl
κ1
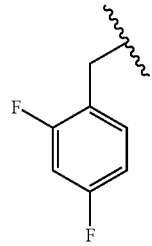
F
F -continued
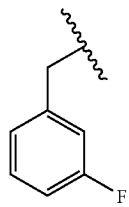
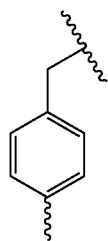
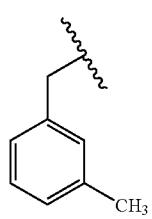
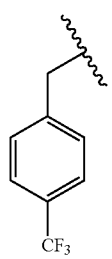
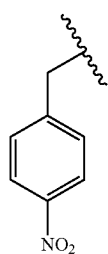
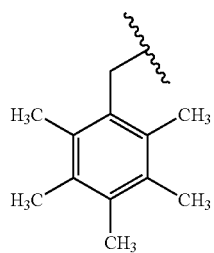
-continued
γ3
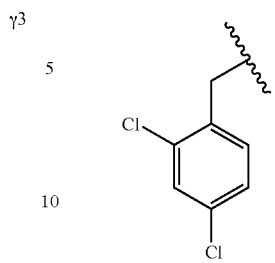
δ2
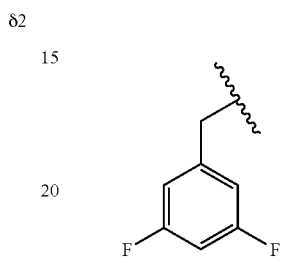
ε3
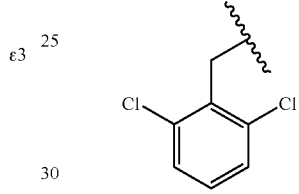
κ2
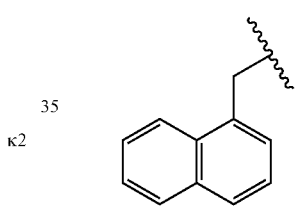
π2
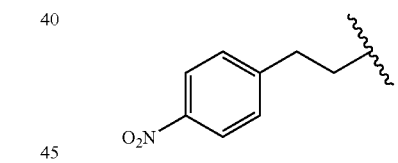
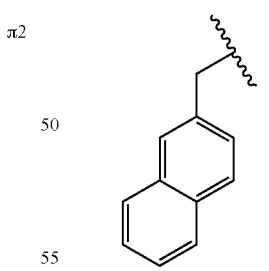
ε4
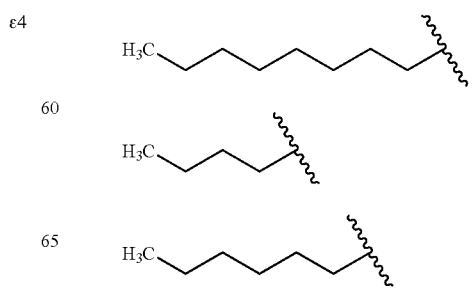
β4
γ4
β5
φ1
π3
φ2
ν1
ν2
ν3

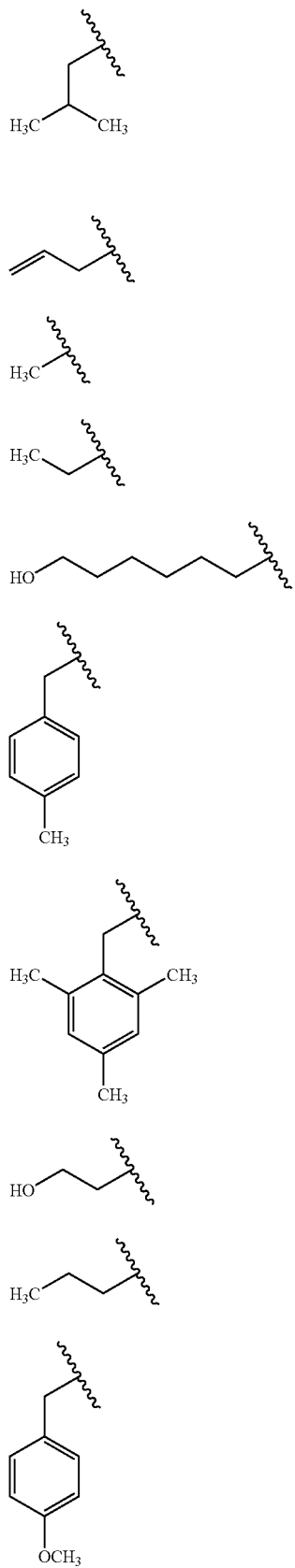
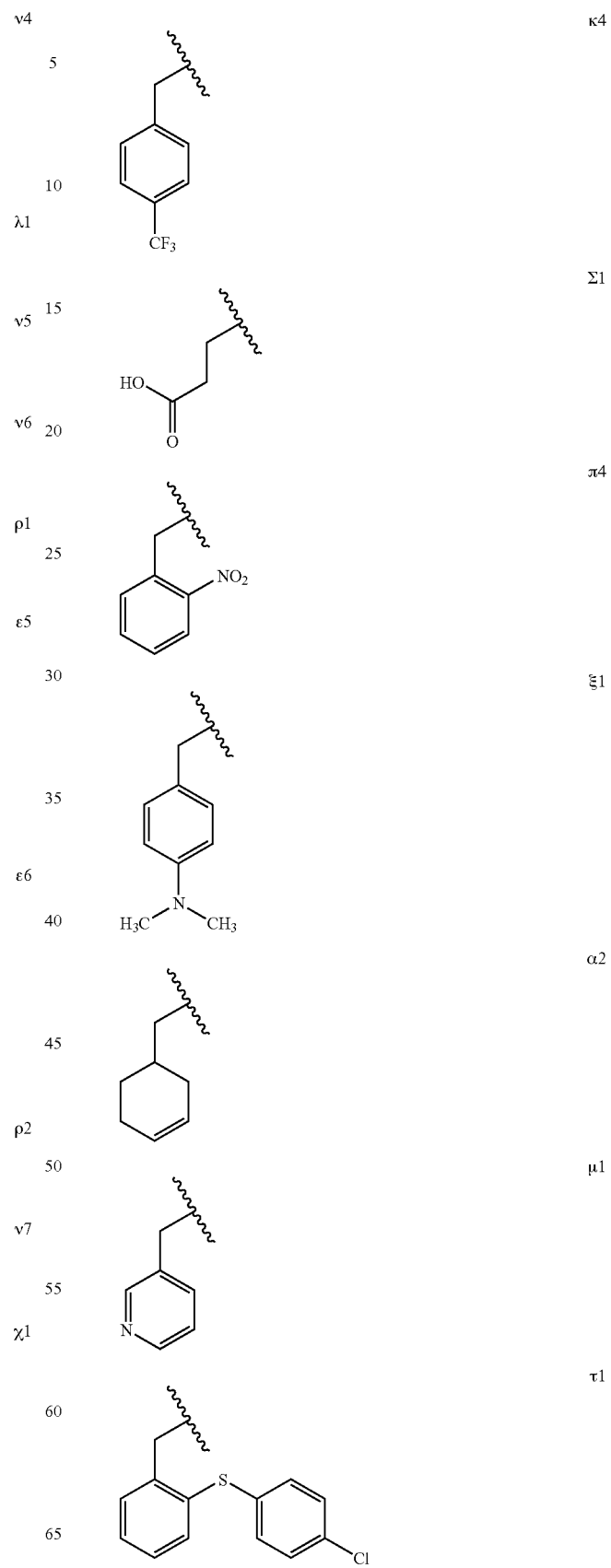

-continued
τ2 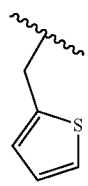
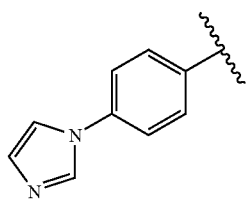 ξ2
μ2 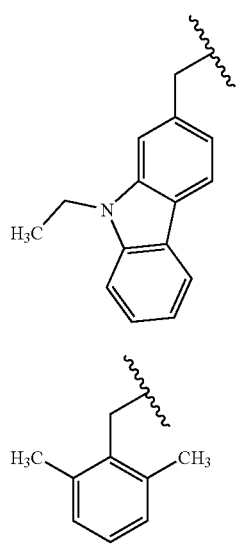
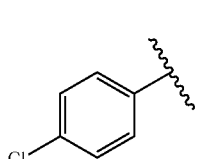 β6
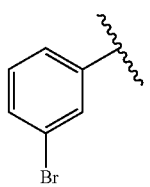 θ1
ε7 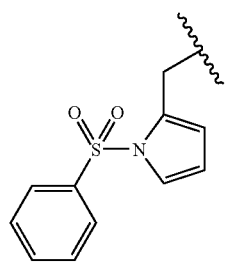
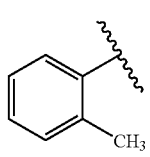 ε8
μ3 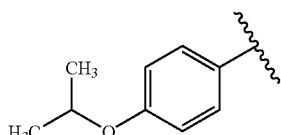 χ2
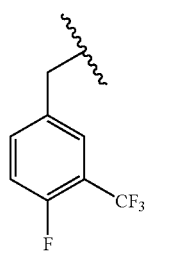
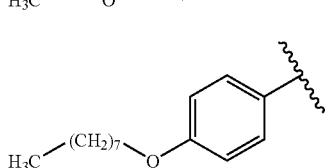 χ3
ψ1 
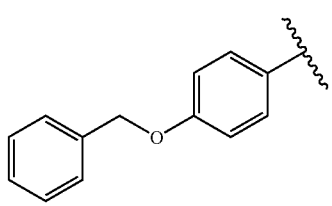 χ4
γ5
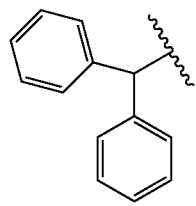
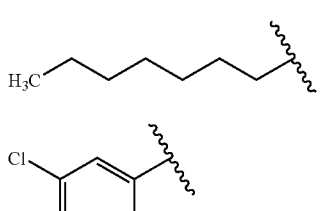 ν8
σ2 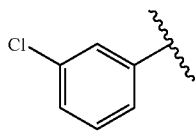 β7
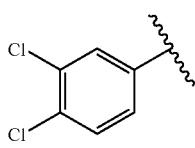 β8

-continued
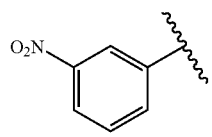 π5
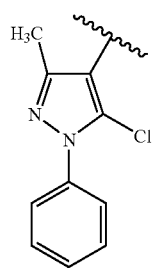 μ4
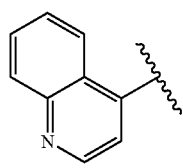 μ5
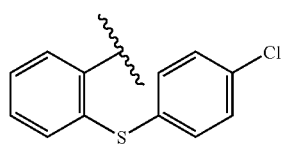 τ3
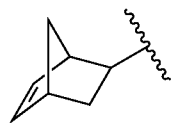 α3
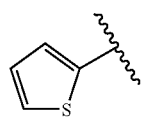 τ4
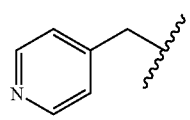 μ10
 κ6
 β12
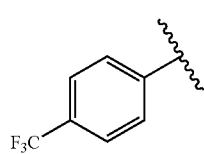 κ6
-continued
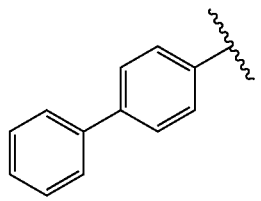 σ3
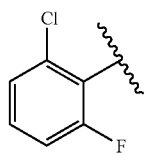 β9
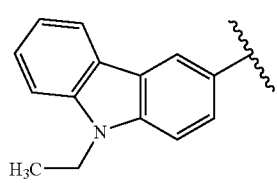 μ6
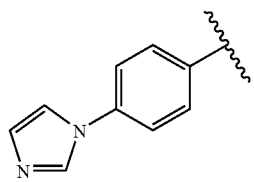 ξ2
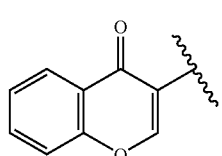 φ1
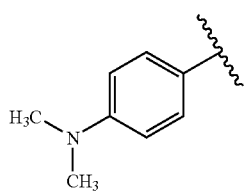 ξ3
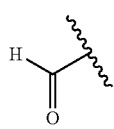 Σ2
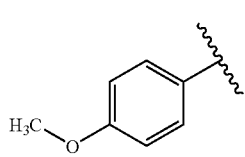 χ5
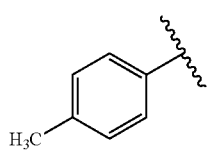 ε9

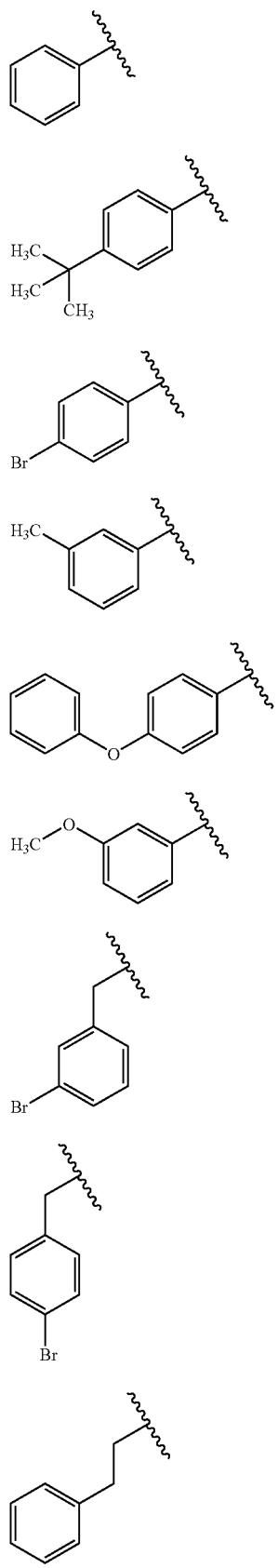
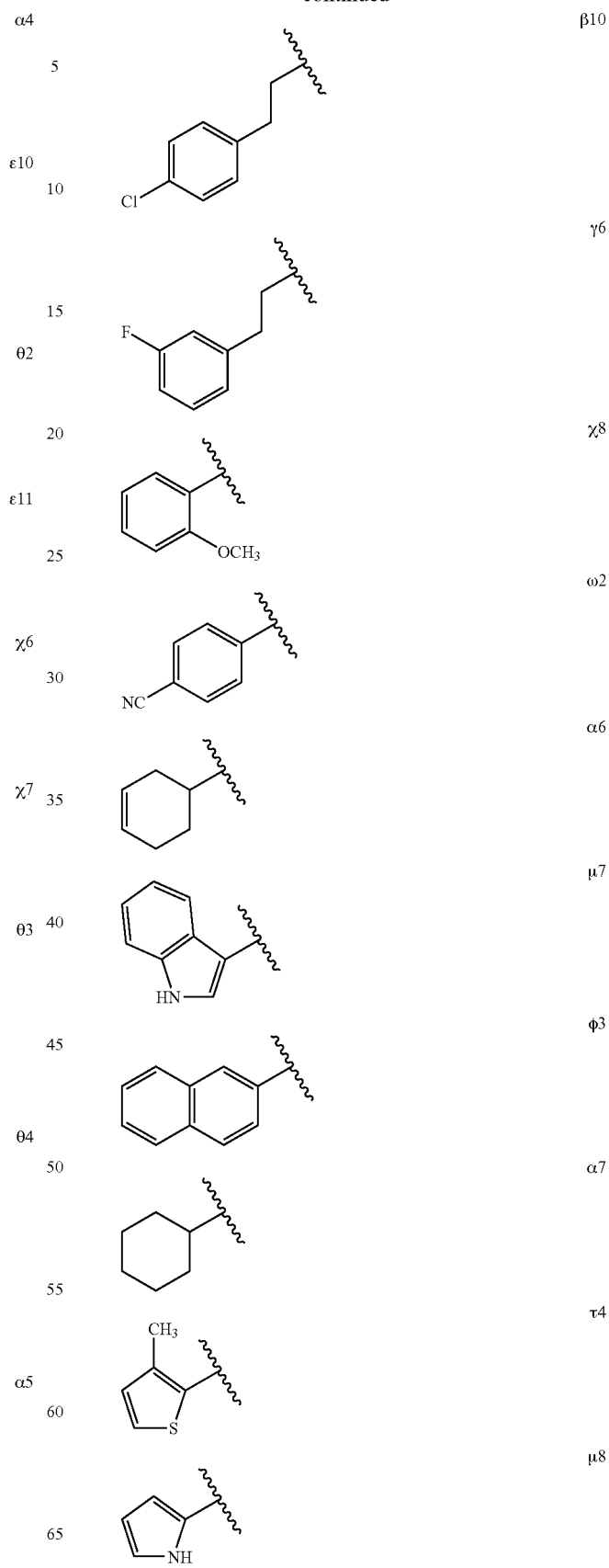

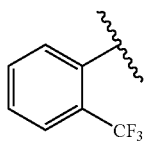 κ3
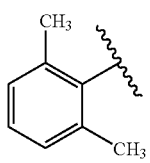 ε12
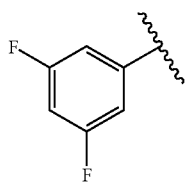 γ7
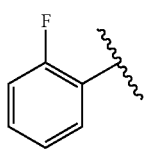 γ8
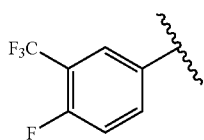 γ9
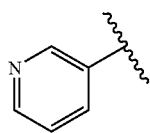 μ9
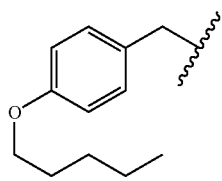 χ9-1
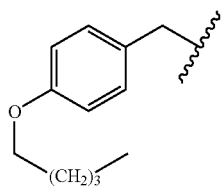 χ10-1
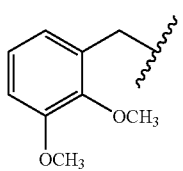 χ11-1
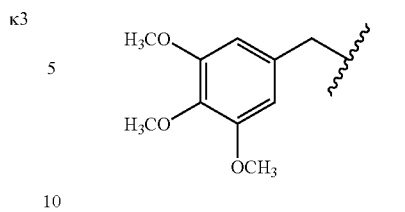 χ12-1
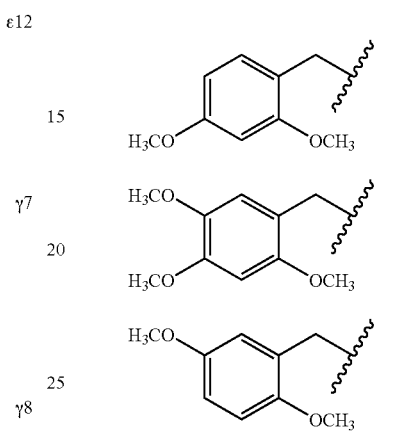 χ13-1
χ14-1
χ15-1
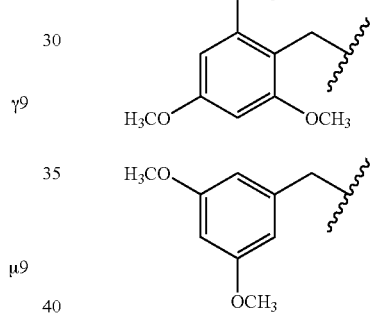 χ16-1
χ17-1
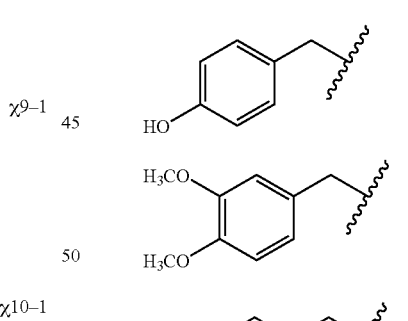 χ18-1
χ19-1
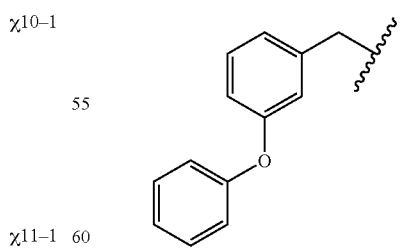 χ20-1
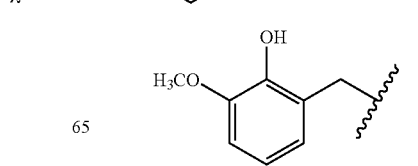 χ21-1

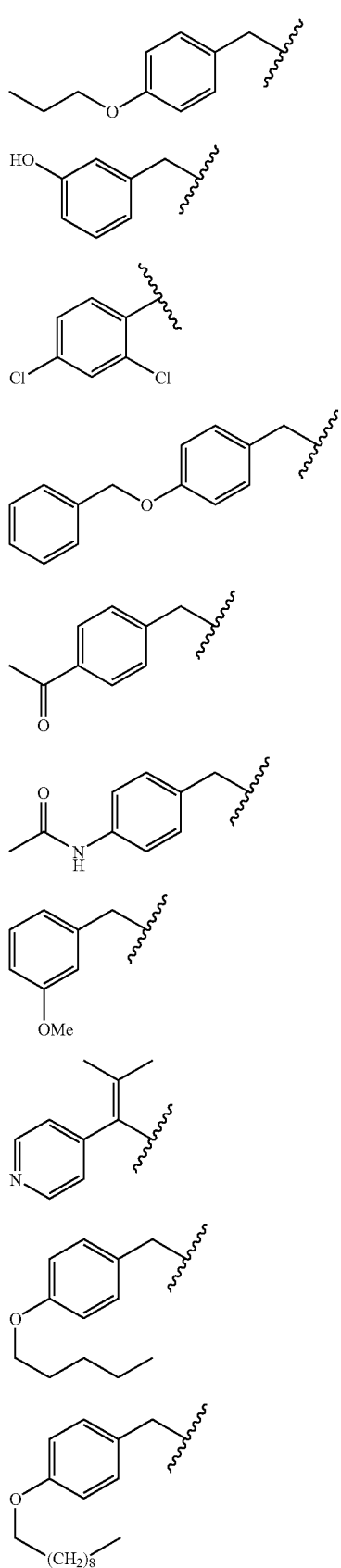
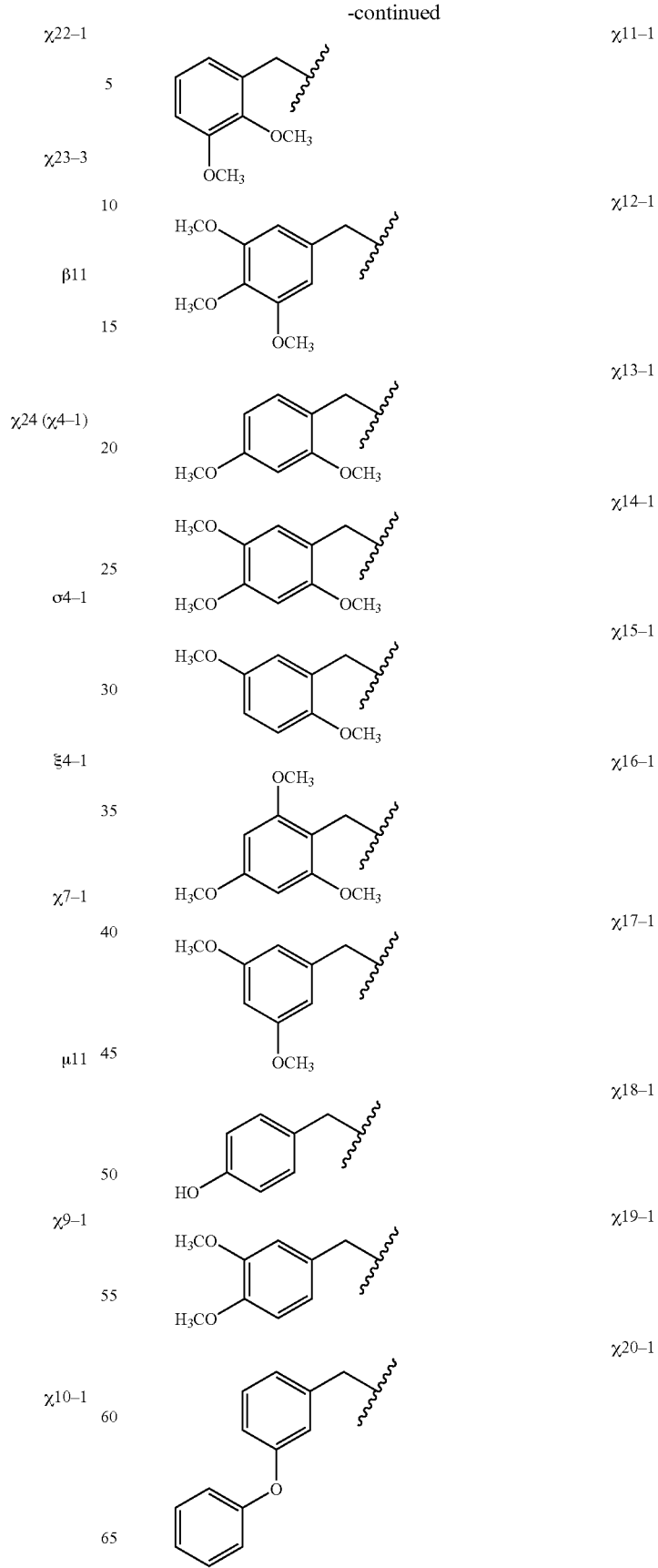

123
-continued
χ21-1
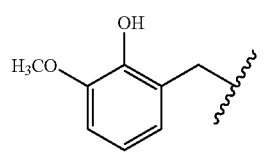
χ22-1
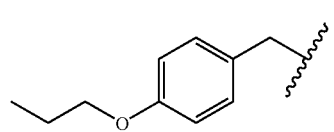
χ23-1
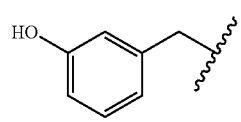
β11
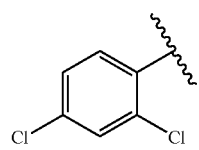
χ24 (χ4-1)
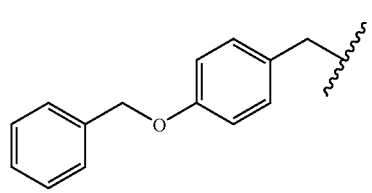
σ4-1
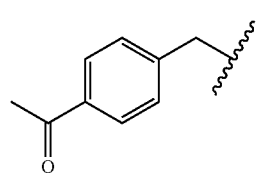
ξ4-1
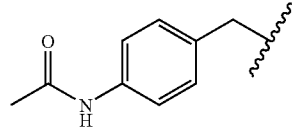
χ7-1
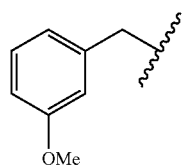
μ11
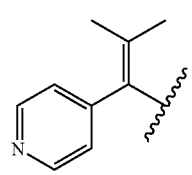
124
-continued
σ2-1
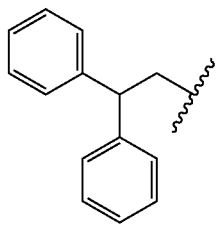
ξ2-1
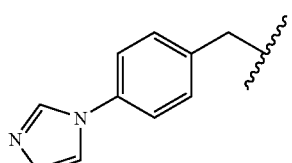
α3-1
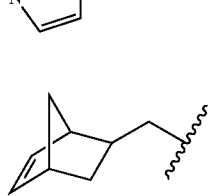
χ2-1
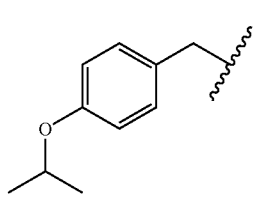
χ3-1
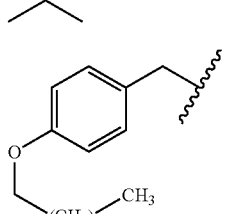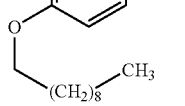
μ5-1
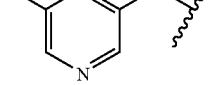
μ6-1
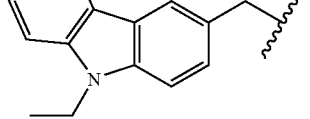
χ8-1
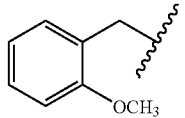
φ1-1
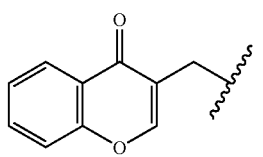

-continued

β9-1
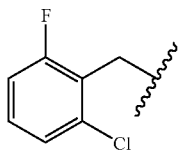

α6-1
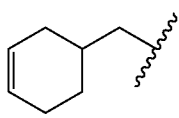

τ5
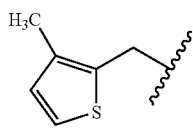

α7-1
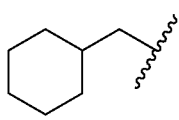

κ7
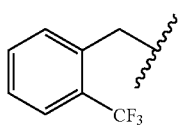

γ8-1,γ10
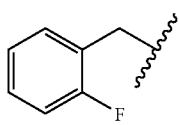

μ13
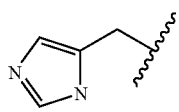

μ12
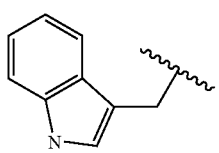

Throughout the specification and the claims (if present), unless the context requires otherwise, the term "comprise", or variations such as "comprises" or "comprising", will be understood to apply the inclusion of the stated integer or group of integers but not the exclusion of any other integer or group of integers.

It should be appreciated that various other changes and modifications can be made to any embodiment described without departing from the spirit and scope of the invention.

The invention claimed is:

1. A compound of formula I

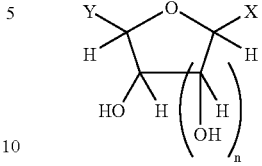

formula I

Wherein;
n is 1,
X is selected from: OR1,

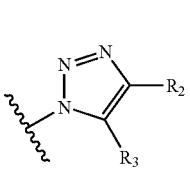 or 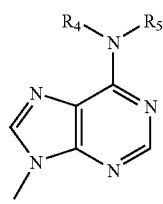

R1 and R3 are independently selected from the group consisting of: C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, R4 is selected from the group consisting of: H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, R5 is selected from the group consisting of: H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl or C3 to C14 heteroarylalkyl, C1 to C7 acyl, C6 to C14 arylacyl, and C3 to C14 heteroarylacyl, R2 is selected from —(C=O)—R3, —(C=O)—OR4, —(C=O)—NH—R4, Y is selected from the group consisting of:

A
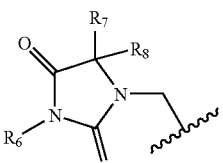

B
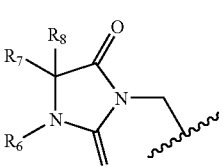

C
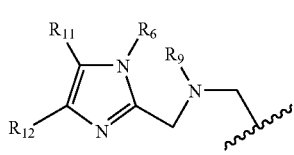

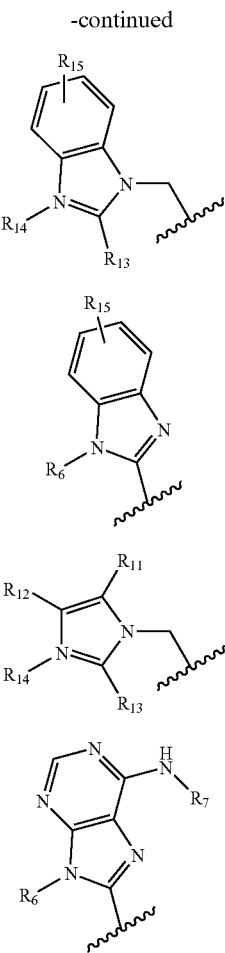

R6 is selected from the group consisting of H, C1 to C7 alkyl, C1 to C7 alkenyl, C1 to C7 alkynyl, C1 to C7 heteroalkyl, C6 to C14 aryl, C3 to C14 heteroaryl, C6 to C14 arylalkyl and C3 to C14 heteroarylalkyl, with the proviso that R6, R7 and R8 are not all H, R9 is selected from H, or —(CO)—R6, R7, R8, R11, R12, R14, are independently selected from the group consisting of: H, C1 to C7 alkyl, C1 to C7 alkenyl, C1 to C7 alkynyl, C1 to C7 acyl, C1 to C7 heteroalkyl, C6 to C14 aryl, C6 to C14 arylacyl, C6 to C14 heteroaryl, C6 to C14 heteroarylacyl, C6 to C14 arylalkyl or C6 to C14 heteroarylalkyl, R13 is selected from the group consisting of: unsubstituted phenyl, unsubstituted benzyl, substituted phenyl, substituted benzyl, H, C1 to C7 alkyl, C1 to C7 alkenyl, C1 to C7 alkynyl, C1 to C7 acyl, C1 to C7 heteroalkyl, C6 to C14 aryl, C6 to C14 arylacyl, C6 to C14 heteroaryl, C6 to C14 heteroarylacyl, C6 to C14 arylalkyl or C6 to C14 heteroarylalkyl, —S—R6 or —O—R6, R15 is absent or is at least one substituent on the aromatic ring which is independently selected from the group consisting of: OH, NO, NO2, NH2, N3, halogen, CF3, CHF2, CH2F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, alkyl, aminoaryl, aminoheteroaryl, thioalkyl, thioaryl or thioheteroaryl.

2. The compound of claim 1, wherein R7 and R8 combine to form a cyclic structure.

3. The compound of claim 1, wherein R6 and one of R7 or R8 combine to form a cyclic structure.

4. The compound of claim 1, wherein R11 and R12 combine to form a cyclic structure.

5. The compound of claim 1, wherein the groups R1, R2, R3, R4 and R5 are cycle, acyclic branched, or linear.

6. The compound of claim 1, wherein R2 and R3 combine to form a ring structure.

7. The compound of claim 1, wherein the groups R4 and R5 combine to form a ring structure.

8. A compound of claim 1 in which at least one of R1 to R14 is substituted with a substituent selected from the group, OH, NO, NO2, NH2, N3, halogen, CF3, CHF2, CH2F, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, alkyl, aminoheteroaryl, thioalkyl, thioaryl or thioheteroaryl.

9. The compound of claim 1 in which the group X is

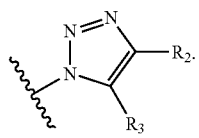

10. The compound of claim 1 in which the group X is

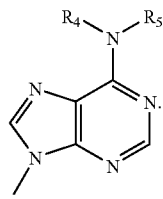

11. The compound of claim 1 in which the group X is —OR1.

12. The compound of claim 9 wherein Y is

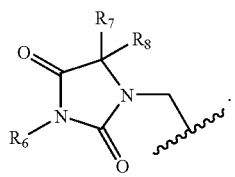

13. The compound of claim 10 wherein Y is

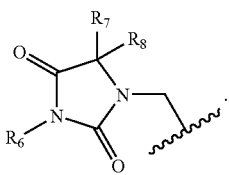

14. The compound of claim 9, wherein Y is

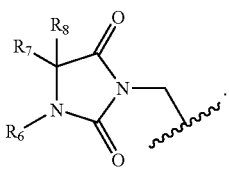

15. The compound of claim 10, wherein Y is

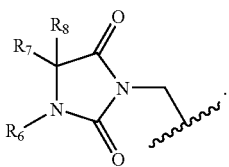

16. The compound of claim 9, wherein Y is

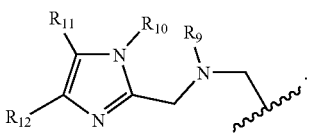

17. The compound of claim 10, wherein Y is

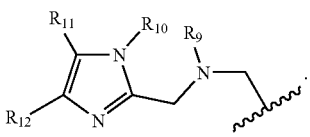

18. The compound claim 9, wherein Y is

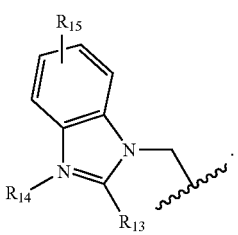

19. The compound claim 10, wherein Y is

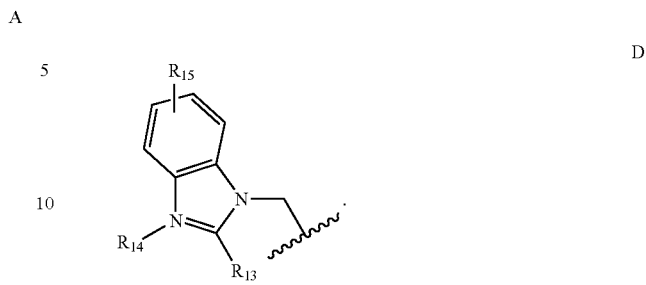

20. The compound of claim 9, wherein Y is

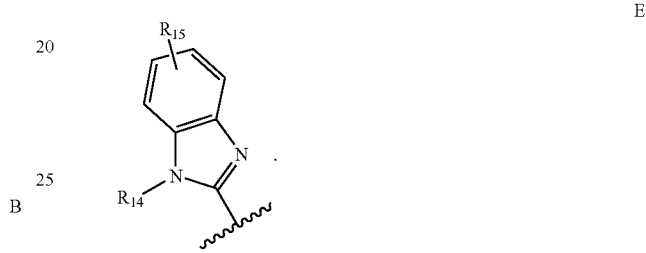

21. The compound of claim 10, wherein Y is

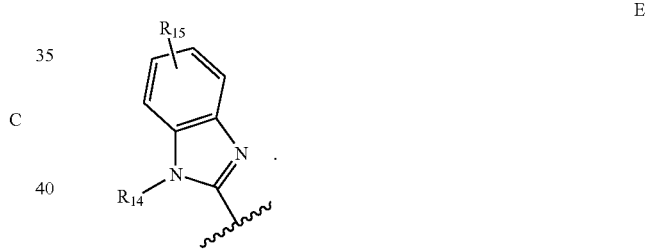

22. The compound of claim 9, wherein Y is

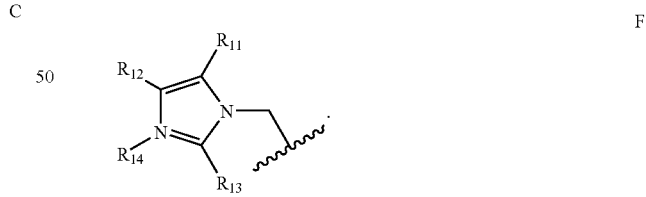

23. The compound of claim 10, wherein Y is

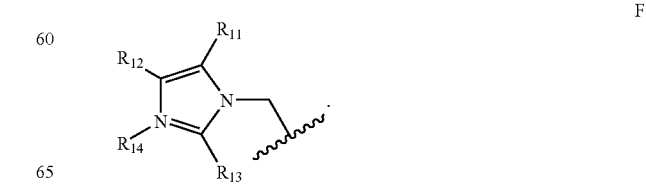

24. The compound claim 9, wherein Y is
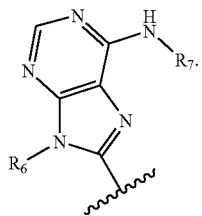
25. The compound claim 10, wherein Y is
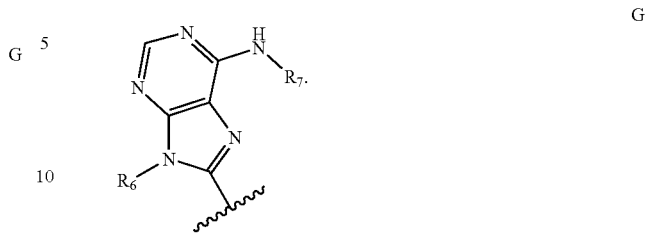
* * * * *